(12) United States Patent
Nicaud et al.

(10) Patent No.: US 12,203,078 B2
(45) Date of Patent: Jan. 21, 2025

(54) INDUCIBLE PROMOTER FOR GENE EXPRESSION AND SYNTHETIC BIOLOGY

(71) Applicants: INSTITUT NATIONAL DE RECHERCHE POUR L'AGRICULTURE, L'ALIMENTATION ET L'ENVIRONNEMENT, Paris (FR); UNIVERSITE LIBRE DE BRUXELLES, Brussels (BE); UNIVERSITE DE LIEGE, Liege (BE)

(72) Inventors: Jean-Marc Nicaud, Trappes (FR); Marion Trassaert, Hazebrouck (FR); Stephane Thomas, Bois d'Arcy (FR); Patrick Fickers, Liege (BE); Marie Vandermies, Ottignies (BE); Frederic Carly, Brussels (BE)

(73) Assignees: INSTITUT NATIONAL DE RECHERCHE POUR L'AGRICULTURE, L'ALIMENTATION ET L'ENVIRONNEMENT, Paris (FR); UNIVERSITE LIBRE DE BRUXELLES, Brussels (BE); UNIVERSITE DE LIEGE, Liege (BE)

( * ) Notice: Subject to any disclaimer, the term of this patent is extended or adjusted under 35 U.S.C. 154(b) by 1122 days.

(21) Appl. No.: 16/612,042

(22) PCT Filed: May 15, 2018

(86) PCT No.: PCT/EP2018/062600
§ 371 (c)(1),
(2) Date: Nov. 8, 2019

(87) PCT Pub. No.: WO2018/210867
PCT Pub. Date: Nov. 22, 2018

(65) Prior Publication Data
US 2020/0149055 A1    May 14, 2020

(30) Foreign Application Priority Data
May 18, 2017   (EP) .................................... 17305575

(51) Int. Cl.
*C12N 15/81* (2006.01)
*C07K 14/39* (2006.01)
*C12N 9/12* (2006.01)

(52) U.S. Cl.
CPC ............ *C12N 15/815* (2013.01); *C07K 14/39* (2013.01); *C12N 9/1205* (2013.01); *C12N 2310/51* (2013.01); *C12N 2830/34* (2013.01); *C12Y 101/01009* (2013.01); *C12Y 207/01027* (2013.01)

(58) Field of Classification Search
CPC ......................... C12N 15/815; C12N 2830/34
See application file for complete search history.

(56) References Cited

U.S. PATENT DOCUMENTS

| 6,265,185 B1 | 7/2001 | Muller et al. |
| 6,582,951 B1 | 6/2003 | Nicaud et al. |
| 8,748,129 B2 | 6/2014 | Nicaud et al. |
| 2013/0089911 A1* | 4/2013 | Zhu ........................ C12P 21/02 435/207 |

FOREIGN PATENT DOCUMENTS

| CN | 101235417 A | 8/2008 |
| WO | 96/41889 A1 | 12/1996 |
| WO | 97/44470 A1 | 11/1997 |
| WO | 00/012729 A1 | 3/2000 |
| WO | 2009/098263 A1 | 8/2009 |

OTHER PUBLICATIONS

Blazeck, John, et al. "Tuning gene expression in *Yarrowia lipolytica* by a hybrid promoter approach." Applied and environmental microbiology 77.22 (2011): 7905-7914. (Year: 2011).*
Roy et al. Core promoters in transcription: old problem, new insights. Trends Biochem Sci. Mar. 2015;40(3):165-71. doi: 10.1016/j.tibs.2015.01.007. Epub Feb. 10, 2015. PMID: 25680757; PMCID: PMC4340783 (Year: 2015).*
Wang et al. Fatty alcohol production in *Lipomyces starkeyi* and *Yarrowia lipolytica*. Biotechnol Biofuels 9, 227 (2016). (Year: 2016).*
Blazeck, John, et al. "Tuning gene expression in *Yarrowia lipolytica* by a hybrid promoter approach." Applied and environmental microbiology 77.22 (2011): 7905-7914. (Year: 2011) (Year: 2011).*
Nishimura et al., Identification of enzyme responsible for erythritol utilization and reaction product in yeast *Lipomyces starkeyi*.J Biosci Bioeng. Apr. 2006;101(4):303-8. doi: 10.1263/jbb.101.303. PMID: 16716937 (Year: 2006).*
GenBank Accession No. CR382132, pp. 1-492 (Year: 2015).*
Blazeck, John, et al. "Tuning gene expression in *Yarrowia lipolytica* by a hybrid promoter approach." Applied and environmental microbiology 77.22 (2011): 7905-7914; cited as Non-Patent Literature Documents #5, on IDS filed Nov. 13, 2020 (Year: 2011).*
Database WPI Week 200870, Thomson Scientific, London, GB, an 2008-L87506, 2017, XP002774572.
Database EMBL [Online], Jan. 5, 2004, "*Oryza sativa* Indica Group cry 2 gene for cryptochrome 2, exons 1-6," XP002774594, retrieved from EBI accession No. EM_STG:AJ490523, Database accession No. AJ490523.
Remi Dulermo et al: "Using a vector pool containing variablestrength promoters to optimize protein production in Yarrowia lipolytica", Microbial Cell Factories, vol. 16, No. 1, Feb. 17, 2017 (Feb. 17, 2017).

(Continued)

*Primary Examiner* — Aaron A Priest
*Assistant Examiner* — Tian Yu
(74) *Attorney, Agent, or Firm* — Arrigo, Lee, Guttman & Mouta-Bellum LLP

(57) ABSTRACT

The invention is related to an inducible promoter for improved and regulated gene expression, useful in synthetic biology and metabolic engineering. In particular, the present invention relates to a nucleotide sequence comprising the regulatory regions of an erythritol- and erythrulose-inducible promoter in yeast and uses thereof in an expression system thus allowing an improved and regulated gene expression and production of gene product.

17 Claims, 19 Drawing Sheets

Specification includes a Sequence Listing.

(56) References Cited

OTHER PUBLICATIONS

Hosni Sassi et al: "Deciphering how LIP2 and POX2 promoters can optimally regulate recombinant protein production in the yeast *Yarrowia lipolytica*", Microbial Cell Factories, vol. 15, No. 1, Sep. 20, 2016 (Sep. 20, 2016).
Marion Trassaert et al: "New inducible promoter for gene expression and synthetic biology in Yarrowia lipolytica", Microbial Cell Factories, vol. 16, No. 1, Aug. 15, 2017 (Aug. 15, 2017), p. 141.
European Search Report, Application No. 17305575.7-1404, Nov. 11, 2017.
International Search Report, Application No. PCT/EP2018/062600, Jun. 27, 2018.
Thomas Juretzek, et al., "Vectors for gene expression and ampli®cation in the yeast *Yarrowia lipolytica*," Yeast 2001; 18:97±113.
Jean-Mare Nieaud, et al., "Expression of invertase activity in Yarrowia lipolytica and its use as a selective marker," Curr Genet (1989) 16:253-260.
Jean-Marc Nicaud, "Yeast Primer; *Yarrowia lipolytica*," Yeast 2012; 29: 409-418.
Barbier, T., Collard, F., Zúñiga-Ripa, A., Moriyón, I., Godard, T., Becker, J., Wittmann, C., Van Schaftingen, E., Letesson, J.-J., 2014. Erythritol feeds the pentose phosphate pathway via three new isomerases leading to Derythrose-4-phosphate in *Brucella*. Proc Natl Acad Sci USA 111, 17815-17820. doi:10.1073/pnas. 1414622111.
Barth, G., Gaillardin, C., 1996. Yarrowia lipolytica, in: Nonconventional Yeasts in Biotechnology. Springer Berlin Heidelberg, pp. 313-388.
Beopoulos, A., Cescut, J., Haddouche, R., Uribelarrea, J.-L., Molina-Jouve, C., Nicaud, J.-M., 2009. Yarrowia lipolytica as a model for bio-oil production. Progress in Lipid Research 48, 375-387. doi:10.1016/j.plipres.2009.08.005.
Beopoulos, A., Nicaud, J.-M., Gaillardin, C., 2011. An overview of lipid metabolism in yeasts and its impact on biotechnological processes. Appl Microbiol Biotechnol 90, 1193-1206. doi:10.1007/s00253-011-3212-8.
Blazeck, J., Liu, L., Redden, H., Alper, H., 2011. Tuning Gene Expression in *Yarrowia lipolytica* by a Hybrid Promoter Approach. Appl Environ Microbiol 77, 7905-7914. doi:10.1128/AEM.05763-11.
Blazeck, J., Reed, B., Garg, R., Gerstner, R., Pan, A., Agarwala, V., Alper, H.S., 2013. Generalizing a hybrid synthetic promoter approach in Yarrowia lipolytica. Appl Microbiol Biotechnol 97, 3037-3052. doi:10.1007/s00253-012-4421-5.
Blazeck, J., Hill, A., Liu, L., Knight, R., Miller, J., Pan, A., Otoupal, P., Alper, H.S., 2014. Harnessing Yarrowia lipolytica lipogenesis to create a platform for lipid and biofuel production. Nature Communications 5, 3131. doi:10.1038/ncomms4131.
Bordes, F., Fudalej F., Dossat V., Nicaud J. M., and Marty. A., 2007. A new recombinant protein expression system for high-throughput screening in the yeast *Yarrowia lipolytica*. J Microbiol Methods 70:493-502.
Carly, F., Gamboa-Melendez, H., Vandermies M., Damblon C., Nicaud J. M., Fickers, P., 2017. Identification and characterization of EYK1, a key gene for erythritol catabolismin Yarrowia lipolytica. Applied Appl Microbiol Biotechnol. Sep.;101(17):6587-6596. doi: 10.1007/s00253-017-8361-y. Epub Jun. 12, 2017.
Carly, F., Steels, S., Telek, S., Vandermies, M., Nicaud, J. M., Fickers, P. 2018. Identification and characterization of EYD1, encoding an erythritol dehydrogenase in Yarrowia lipolytica and its application to bioconvert erythritol into erythrulose. Bioresource technology, 247: 963-969. doi/10.1016/j.biortech.2017.09.168.
Celińska, E., Ledesma Amaro, R., Larroudé, M., Rossignol, T., Pauthenier, C., Nicaud, J.-M., 2017. Golden Gate Assembly system dedicated to complex pathway manipulation in Yarrowia lipolytica. Microbial Biotechnology, 10 (2), 450-455. DOI : 10.1111/1751-7915.12605.
Dulermo, R., Brunel, F., Dulermo, T., Ledesma-Amaro, R., Vion, J., Trassaert, M., Thomas, S., Nicaud, J.-M., Leplat, C., 2017. Using a vector pool containing variable-strength promoters to optimize protein production in Yarrowia lipolytica. Microb Cell Fact 16. doi:10.1186/s12934-017-0647-3.
Emond, S., Montanier, C., Nicaud, J. M., Marty, A., Monsan, P., Andre, I., Remaud-Simeon, M., 2010. New efficient recombinant expression system to engineer Candida antarctica lipase B. Appl Environ Microbiol 76:2684-2687.
Fickers, P., Le Dall, M.., Gaillardin, C., Thonart, P., Nicaud, J.., 2003. New disruption cassettes for rapid gene disruption and marker rescue in the yeast ~*Yarrowia lipolytica*. Journal of Microbiological Methods 55, 727-737. doi:10.1016/j.mimet.2003.07.003.
Fickers, P., Benetti, P., Wache, Y., Marty, A., Mauersberger, S., Smit, M., Nicaud, J., 2005. Hydrophobic substrate utilisation by the yeast *Yarrowia lipolytica*, and its potential applications. FEMS Yeast Research 5, 527-543. doi:10.1016/j.femsyr.2004.09.004.
Friedlander, J., Tsakraklides, V., Kamineni, A., Greenhagen, E.H., Consiglio, A.L., MacEwen, K., Crabtree, D.V., Afshar, J., Nugent, R.L., Hamilton, M.A., Joe Shaw, A., South, C.R., Stephanopoulos, G., Brevnova, E.E., 2016. Engineering of a high lipid producing Yarrowia lipolytica strain. Biotechnology for Biofuels 9, 77. doi:10.1186/s13068-016-0492-3.
Gajdoš, P., Ledesma-Amaro, R., Nicaud, J. M., Čertik, M., Rossignol, T., 2016. Overexpression of DGAT in Yarrowia lipolytica affects lipid body size, number, and distribution. FEMS Yeast Res. Aug. 8, 2016. pii: fow062. [Epub ahead of print], DOI: 10.1093/femsyr/fow062.
Groenewald, M., Boekhout, T., Neuvéglise, C., Gaillardin, C., van Dijck, P.W.M., Wyss, M., 2014. Yarrowia lipolytica: Safety assessment of an oleaginous yeast with a great industrial potential. Critical Reviews in Microbiology 40, 187-206. doi:10.3109/1040841X.2013. 770386.
Haddouche R., Delessert S., Sabirova J., Neuvéglise C., Poirier Y., Nicaud J.M. 2010. Roles of multiple acyl-CoA oxidases in the routing of carbon flow towards ß-oxidation and polyhydroxyalkanoate biosynthesis in Yarrowia lipolytica. FEMS Yeast Res 10: 917-927.
Hong, S.-P., Seip, J., Walters-Pollak, D., Rupert, R., Jackson, R., Xue, Z., Zhu, Q., 2012. Engineering Yarrowia lipolytica to express secretory invertase with strong FBA1IN promoter. Yeast 29, 59-72. doi:10.1002/yea.1917.
Hussain, M.S., Gambill, L., Smith, S., Blenner, M.A., 2016. Engineering promoter architecture in oleaginous yeast *Yarrowia lipolytica*. ACS Synth Biol 5, 213-223. doi:10.1021/acssynbio.5b00100.
Juretzek, T., Wang, H.-J., Nicaud, J.-M., Mauersberger, S., Barth, G., 2000. Comparison of promoters suitable for regulated overexpression of β-galactosidase in the alkane-utilizing yeast *Yarrowia lipolytica*. Biotechnol. Bioprocess Eng. 5, 320-326. doi:10.1007/BF02942206.
Trassaert, M., Vandermies, M., Carly, F., Denies, O., Thomas, S., Fickers, P., Nicaud, J.-M. 2017. New inducible promoter for gene expression and synthetic biology in Yarrowia lipolytica. Microbial Cell Factories, 16. , DOI : 10.1186/s12934-017-0755-0.
Le Dall, M.T., Nicaud, J.M., Gaillardin, C., 1994. Multiple-copy integration in the yeast *Yarrowia lipolytica*. Curr. Genet. 26, 38-44.
Ledesma-Amaro, R., Nicaud, J.-M., 2016. Yarrowia lipolytica as a biotechnological chassis to produce usual and unusual fatty acids. Progress in Lipid Research 61, 40-50. doi:10.1016/j.plipres.2015. 12.001.
Madzak, C., Treton, B., Blanchin-Roland, S., 2000. Strong hybrid promoters and integrative expression/secretion vectors for quasi-constitutive expression of heterologous proteins in the yeast *Yarrowia lipolytica*. J. Mol. Microbiol. Biotechnol. 2, 207-216.
Livak, K.J., Schmittgen, T.D., 2001. Analysis of relative gene expression data using realtimequantitative PCR and the 2-ΔΔCT method. Methods 25, 402-408.
Madzak, C., Beckerich, J.-M., 2013. Heterologous Protein Expression and Secretion in Yarrowia lipolytica, in: Barth, G. (Ed.), Yarrowia Lipolytica, Microbiology Monographs. Springer Berlin Heidelberg, pp. 1-76.
Madzak, C., 2015. Yarrowia lipolytica: recent achievements in heterologous protein expression and pathway engineering. Appl. Microbiol. Biotechnol. 99, 4559-4577. doi:10.1007/s00253-015-6624-z.

(56) References Cited

OTHER PUBLICATIONS

Müller, S., Sandal, T., Kamp-Hansen, P., Dalbøge, H., 1998. Comparison of expression systems in the yeasts *Saccharomyces cerevisiae, Hansenula polymorpha, Klyveromyces lactis, Schizosaccharomyces pombe* and *Yarrowia lipolytica*. Cloning of two novel promoters from Yarrowia lipolytica. Yeast 14, 1267-1283. doi:10.1002/(SICI)1097-0061(1998100)14:14<1267::AIDYEA327> 3.0.CO;2-2.

Vandermies, M., Denies, O., Nicaud, J.-M., Fickers, P., 2017. EYK1 encoding erythrulose kinase as a catabolic selectable marker for genome editing in the non-conventional yeast *Yarrowia lipolytica*. Journal of Microbiological Methods, 139, 161-164. , DOI : 10.1016/j.mimet.2017.05.012.

Nicaud, J-M, Madzak, C., van den Broek, P., Gysler, C., Duboc, P., Niederberger, P. Gaillardin, C., 2002. Protein expression and secretion in the yeast *Yarrowia lipolytica*. FEMS Yeast Research 2/3:371-379.

Wang, X., Sun, Y., Ke, F., Zhao, H., Liu, T., Xu, L., Liu, Y., Yan, Y., 2012. Constitutive expression of Yarrowia lipolytica lipase LIP2 in Pichia pastoris using GAP as promoter. Appl Biochem Biotechnol 166, 1355-1367. doi:10.1007/s12010-011-9524-4.

Ogrydziak, D.M., Scharf, S.J., 1982. Alkaline extracellular protease produced by Saccharomycopsis lipolytica CX161-1B. J. Gen. Microbiol. 128, 1225-1234. doi:10.1099/00221287-128-6-1225.

Xuan JW, Fournier P, Declerck N, Chasles M, Gaillardin C. 1990. Overlapping reading frames at the LYS5 locus in the yeast *Yarrowia lipolytica*. Mol Cell Biol. 10:4795-806.

Pignède, G., Wang, H., Fudalej, F., Gaillardin, C., Seman, M., Nicaud, J.-M., 2000. Characterization of an Extracellular Lipase Encoded by LIP2 in Yarrowia lipolytica. J Bacteriol 182, 2802-2810.

Querol, A., Barrio, E., Huerta, T., Ramón, D., 1992. Molecular Monitoring of Wine Fermentations Conducted by Active Dry Yeast Strains. Appl Environ Microbiol 58, 2948-2953.

Richard, M., Quijano, R.R., Bezzate, S., Bordon-Pallier, F., Gaillardin, C., 2001. Tagging morphogenetic genes by insertional mutagenesis in the yeast Yarrowia lipolytica. J. Bacteriol. 183,3098-3107.

Zinjarde, S.S., 2014. Food-related applications of Yarrowia lipolytica. Food Chemistry 152, 1-10. doi:10.1016/j.foodchem.2013.11.117.

Sassi, H., Delvigne, F., Kar, T., Nicaud, J.-M., Coq, A.-M.C.-L., Steels, S., Fickers, P., 2016. Deciphering how LIP2 and POX2 promoters can optimally regulate recombinant protein production in the yeast *Yarrowia lipolytica*. Microb Cell Fact 15, 159. doi:10.1186/s12934-016-0558-8.

Schmid-Berger N., Schmid B., Barth G.. 1994. Ylt1, a highly repetitive retrotransposon in the genome of the dimorphic fungus *Yarrowia lipolytica*. J Bacteriol 176: 2477-2482.

Sibirny, A.A., Madzak, C., Fickers, P., 2014. Genetic engineering of nonconventional yeast for the production of valuable compounds, in: Microbial Biotechnology Progress and Trends. CRC Press, USA, pp. 63-112.

Sievers, F., Wilm, A., Dineen, D., Gibson, T. J., Karplus, K., Li, W., Lopez, R., McWilliam, H., Remmert, M., Söding, J., Thompson, J. D., Higgins, D. G., 2011. Fast, scalable generation of high-quality protein multiple sequence alignments using Clustal Omega. Mol Syst Biol. Oct. 11;7:539. doi:10.1038/msb.2011.75.

Tai, M., Stephanopoulos, G., 2013. Engineering the push and pull of lipid biosynthesis in oleaginous yeast *Yarrowia lipolytica* for biofuel production. Metabolic Engineering 15, 1-9. doi:10.1016/j.ymben.2012.08.007.

Thevenieau, F., Nicaud, J.-M., 2013. Microorganisms as sources of oils. OCL 20, D603. doi:10.1051/ocl/2013034.

\* cited by examiner

INDUCIBLE PROMOTER FOR GENE EXPRESSION AND SYNTHETIC BIOLOGY

SEQUENCE LISTING

The sequence listing submitted herewith as an ASCII text file is named 16612042, was created on Sep. 29, 2020, is 32,493 byes in size, and is hereby incorporated herein by reference.

INTRODUCTION

The present invention is related to an inducible promoter for improved and regulated gene expression, useful in synthetic biology and metabolic engineering. In particular, the present invention relates to a nucleotide sequence comprising the regulatory regions of an erythritol- and erythrulose-inducible promoter in yeast and uses thereof in an expression system thus allowing an improved and regulated gene expression and production of gene products.

Interest in non-conventional yeasts such as *Pichia pastoris, Hansenula polymorpha* (*Pichia angusta*), and *Yarrowia lipolytica* as cell factories for the production of recombinant proteins or biomolecules with biotechnological or pharmaceutical applications has increased over the years (Sibirny et al 2014). In *Y. lipolytica* more than one hundred heterologous proteins have been successfully produced at high yield, underscoring its production potential (Madzak, 2015). *Y. lipolytica* is a model yeast species that is well-known for its unusual metabolic properties such as the ability to grow on fatty acids or alkanes as sole carbon source and to accumulate intracellular lipids at high yield (Fickers et al., 2005; Nicaud 2012). This feature has enable the development of metabolic engineering strategies to construct mutant strains to produce lipid for biodiesel and biojetfuel (Beopoulos et al 2009, 2011, Thevenieau and Nicaud 2013, Blazeck et al 2014, Friedlander et al 2016, Tai and Stephanopoulos 2013), or to synthetize unusual fatty acid, such as ω-3, ricinoleic acid, conjugated fatty acid, and fatty acid derivatives such as fatty alcohol or dicarboxilic acid (Ledesma et al 2016). Due to its ability to secrete large amounts of proteins and metabolites, *Y. lipolytica* has several industrial applications, including heterologous protein synthesis, citric acid and erythritol production (Fickers et al., 2005). *Y. lipolytica* has been accorded GRAS (Generally Recognized As Safe) status (Groenewald et al 2014, Zinjarde 2014).

When developing an efficient cell factory, the choice of the promoter driving recombinant gene expression is crucial, and therefore represents one of the key parameters to be optimized. At present, few promoters have been identified and their regulation is not fully understood yet. Historically, the promoter from the XPR2 gene, which encodes an alkaline extracellular protease, was the first to be characterized (Ogrydziak and Scharf, 1982). Although this promoter has been used successfully, its full induction requires high peptides concentrations and a pH above six, conditions that are often unfeasible at industrial scale.

Comparison of strength and regulation of promoters from the glycerol-3-phosphate dehydrogenase (G3P), the isocitrate lyase (ICL1) and of genes involved in beta-oxidation pathway such as the 3-oxo-acyl-CoA thiolase (POT1) and the acyl-CoA oxidases (POX2, POX1 and POX5) was reported (Juretzek et al. 2000). This provided the first strong promoter inducible by glycerol (G3P), ethanol (ICL) and oleic acid (POT1 and POX2). Other regulated promoters, such as the one from LIP2 and POX2 gene encoding an extracellular lipase and acyl-CoA oxidase 2, respectively, have been developed and characterized (Pignede et al 2000, Sassi et al 2016). Using expression vectors based on pLIP2, higher protein productivities such as for Lip2p lipase have been obtained in *Y. lipolytica* than in other cell factories such as *P. pastoris*. Using the GAP constitutive promoter, Wang and coll (2012) obtained lipase activity levels of 13,500 U/mL using a glucose fed-batch process in a 10-L bioreactor. In contrast, activity levels of 150,000 U/mL were obtained using a LIP2 promoter and a tryptone-olive oil fed-batch process (Fickers et al 2005). However, the utilization of pLIP2 and pPOX2 is difficult in practice, especially in large-scale bioreactor, due to the hydrophobic nature (water insoluble) of the inducer (i.e. fatty acids or triglycerides). Other inducible promoters available in *Y. lipolytica* are those from genes encoding isocitrate lyase (pICL1, Juretzeck et al, 2000), fructose-bisphosphate aldolase (pFBA1, Hong et al, 2012), phosphoglycerate mutase (pGPM) or glycerol-3-phosphate O-acyltransferase (pGPAT). They have been used for heterologous protein production with various successes (for a review see Madzak et al. 2015).

Constitutive promoters have also been considered. The functional dissection of pXPR2 allowed the identification of one of its upstream activating sequence (UAS1xpr2) that is poorly affected by cultivation conditions. Hybrid promoters, containing up to four direct repeats of UAS1xpr2 upstream of the minimal LEU2 promoter (mLEU2), were first constructed (Madzak, et al., 2000, WO 96/41889). Among these, hp4d was widely used for heterologous protein production (for review see Madzak & Beckerich, 2013). This latter has been at the basis of the *Y. lipolytica* YLEX expression kit commercialised by Yeastern Biotech Co. (Taiwan). More recently, an extended series of hybrid promoters, carrying various copy number (up to 32) of UAS1xpr2 upstream of mLEU2 were constructed (Blazeck et al 2011). Some of these hybrid promoters were shown to possess efficiency eight-fold higher that any know endogenous promoter from *Y. lipolytica* (Blazeck et al 2011). Promoter from the TEF1 gene encoding the translation elongation factor-1α (Muller et al 1998, U.S. Pat. No. 6,265,185) is also widely used to drive constitutive gene expression in *Y. lipolytica*. Hybrid promoters with variable strength derived from the latter were recently tested for the production of secreted production enzyme of industrial interest such as xylanase and glucoamylase (Dulermo et al 2017). This study highlighted that the higher protein productivity does not necessarily rely on the strength of the promoter used for the corresponding gene expression.

In synthetic biology, gene expression must be fine-tuned in order to ensure optimal fluxes in the corresponding pathway or to avoid metabolic burden. Hussain et al (2016) investigated promoter strength by shuffling promoter constitutive elements (UAS, proximal promoter, TATA box and core promoter) of various fungal gene promoters (TEF, POX2, LEU2, PAT1) in *Y. lipolytica*. They find out that engineering promoter architecture allows to modulate and to fine-tune gene expression level. However, to further expand the range of this regulation, a novel regulatory element (UAS) and thus novel regulated promoter remains to be discovered.

Therefore, there is a lack for versatile inducible promoter for gene expression in yeast, and especially in *Yarrowia lipolytica*.

SUMMARY OF THE INVENTION

The inventors have identified an inducible promoter of the EYK1 gene encoding the erythritol kinase and of the EYD1 gene encoding the erythritol dehydrogenase, identified its regulatory elements and developed new inducible derivative promoters showing different promoter strength and different regulatory pattern, in particular depending on the genetic background of the recipient strain, in particular wild-type or Δeyk1 or Δeyd1, useful for metabolic engineering, recombinant protein production and synthetic biology.

The present invention thus provides a major industrial advantage for the expression of gene products and the production of secreted synthesis of the corresponding proteins, since conventional culture medium may be used, at lower price.

The present invention is thus related to a nucleotide sequence comprising at least one sequence according to formula (I) and/or at least one sequence according to formula (II), wherein:

formula (I) is

CGGNNX$_1$CNNNANNX$_2$GNNAAGNCG (I)

with N being any nucleotide with X$_1$ and X$_2$ being any nucleotide or nothing, as set forth in anyone of SEQ ID NO: 1, SEQ ID NO: 2, SEQ ID NO: 3 and SEQ ID NO: 4;

formula (II) is

ANTTNNNTTTCCNNATNNGG (II)

with N being any nucleotide, as set forth in SEQ ID NO: 5.

Preferably, the nucleotide sequence of the invention comprises tandem repeats of at least one sequence according to formula (I) and/or at least one sequence according to formula (II) as defined above.

More preferably, the nucleotide sequence of the invention comprises at least one sequence according to formula (I) and further comprises at least one sequence according to formula (III) which is

CNTGCATNATCCGANGAC (III)

with N being any nucleotide.

In a preferred embodiment, the nucleotide sequence of the invention is comprising or consisting of the sequence as set forth in SEQ ID NO: 13, in SEQ ID NO: 101 or SEQ ID NO: 102.

Preferably, the at least one sequence according to formula (I) and/or the at least one sequence according to formula (II) of the nucleotide sequence of the present invention is/are upstream to an ATG.

The present invention is also related to an erythritol- and/or erythrulose-inducible promoter sequence functional in yeast, comprising the nucleotide sequence as defined above and a core promoter.

The present invention is also related to a construct comprising the erythritol- and/or erythrulose-inducible promoter sequence according to the invention, operably linked to polynucleotide sequence encoding a gene product to be transcribed from such inducible promoter.

A eukaryotic host cell comprising the erythritol- and/or erythrulose-inducible promoter sequence or a construct according to the invention, is also an object of the present invention.

The host cell may be a yeast host cell.

The host cell may also have the endogenous gene encoding the L-erythrulose kinase and/or the endogenous gene encoding the erythritol dehydrogenase inhibited.

The present invention also relates to a method for expressing a gene, producing the encoded protein, comprising the steps of growing a host cell comprising the construct according to the invention in an appropriate culture medium and adding at least erythritol and/or erythrulose to the culture medium.

DETAILED DESCRIPTION OF THE INVENTION

Promoters are generally constituted of different parts including Upstream Activating Sequence or Upstream Activation Sequence (UAS), proximal sequence, a TATA box and a core promoter. The strength and regulation of a promoter depends on these different elements.

An UAS is a cis-acting regulatory sequence, which is part from the promoter and increases the expression of a neighboring gene. The TATA box contains a consensus sequence characterized by repeating T and A base pairs. The core promoter is the first upstream sequence of a promoter not allowing expression alone.

In a first aspect, the present invention is related to a nucleotide sequence comprising at least one sequence according to formula (I) and/or at least one sequence according to formula (II), wherein:

formula (I) is

CGGNNX$_1$CNNNANNX$_2$GNNAAGNCG (I)

with N being any nucleotide with X$_1$ and X$_2$ being any nucleotide or nothing, as set forth in anyone of SEQ ID NO: 1, SEQ ID NO: 2, SEQ ID NO: 3 and SEQ ID NO: 4;

formula (II) is

ANTTNNNTTTCCNNATNNGG (II)

with N being any nucleotide, as set forth in SEQ ID NO: 5.

In one embodiment, the nucleotide sequence comprises at least one sequence according to formula (II) as set forth in SEQ ID NO: 5.

In a preferred embodiment of the invention, the present invention is related to a nucleotide sequence comprising at least one sequence according to formula (I) for anyone of SEQ ID NO: 1, SEQ ID NO: 2, SEQ ID NO: 3 and SEQ ID NO: 4.

When the nucleotide sequence comprises at least one sequence according to formula (I), this sequence is selected in the group consisting of:

CGGVVVYCYBVAWDGRRAAGSCG (SEQ ID NO: 6)

CGGVWCYBVAWDKGRRAAGSCG (SEQ ID NO: 7)

CGGVVVYCYBVAWDKGRRAAGSCG (SEQ ID NO: 8)

CGGVWCYBVAWDGRRAAGSCG (SEQ ID NO: 9)

In a more preferred embodiment, the sequence according to formula (I) is selected in the group consisting of SEQ ID NO: 1, SEQ ID NO: 2, SEQ ID NO: 4, SEQ ID NO: 6, SEQ ID NO: 7 and SEQ ID NO: 9.

In a preferred embodiment of the invention, when the nucleotide sequence comprises at least one sequence according to formula (II), this sequence is ABTTSYRTTTCCY-WATDHGG, as set forth in SEQ ID NO: 10.

In a preferred embodiment of the invention, the nucleotide sequence comprises at least one sequence according to formula (I) and at least one sequence according to formula (II). More preferably in this embodiment, said sequence according to formula (I) is selected in the group consisting of SEQ ID NO: 6, SEQ ID NO: 7, SEQ ID NO: 8 and SEQ ID NO: 9, and the sequence according to formula (II) is SEQ ID NO: 10.

In the nucleotide sequence according to the invention, the sequence as according to formula (I) and/or the sequence according to formula (II) may be present in several copies which can be either with an even or odd number, preferably an even number, also called a tandem repeat (all direct or all inverted) or any combination of both orientations.

Preferably, the nucleotide sequence of the invention may contain at least 2 copies of the sequence according to formula (I) and/or of the sequence according to formula (II), and more preferably from 2 to 32 copies of the sequence according to formula (I) and/or sequence according to formula (II), even more preferably from 2 to 16 sequences, and most preferably from 2 to 8. In a specific embodiment, the nucleotide sequence of the invention contains 2, 3, 4, 5, 6, 7 or 8 copies of the sequence according to formula (I) and/or of the sequence according to formula (II). The sequence according to formula (I) and/or according to formula (II) in all embodiments described here it can be either in the same orientation or not, preferably in the same orientation.

Preferably, the nucleotide sequence according to the invention comprises tandem repeats of the sequence according to formula (I)/or of the sequence according to formula (II), as defined above.

The nucleotide sequence of the invention may comprise, or consists of, two tandem copies of said sequences according to formula (I) and/or according to formula (II), or may comprises, or consists of, one or several four tandem copies of said sequences, viz. 4, 8, 16 and 32.

In one embodiment, the nucleotide sequence according to the invention comprises at least one sequence according to formula (I) and further comprises at least one sequence according to formula (III) which is

CNTGCATNATCCGANGAC (III)

with N being any nucleotide, as set forth in SEQ ID NO: 11.

In a preferred embodiment of the invention, when the nucleotide sequence comprises at least one sequence according to formula (I) and at least one sequence according to formula (III) as set forth in SEQ ID NO: 12, which is: CDTGCATWATCCGAYGAC.

As mentioned above, the sequence according to formula (I) and the sequence according to formula (III) as set forth in SEQ ID NO: 11 may be present in several copies which can be either tandem repeats (all direct or all inverted) or any combination of both orientations, and all the preferred embodiments defined above for the sequence according to formula (I) and according to formula (II) may applied to a nucleotide sequence containing the sequence according to formula (I) and the sequence as set forth in SEQ ID NO: 11.

In an advantageous embodiment of the present invention, the nucleotide sequence comprises or consists of the sequence as set forth in SEQ ID NO: 13.

In other advantageous embodiments of the present invention, the nucleotide sequence comprises or consists of the sequences as set forth in SEQ ID NO: 101 or comprises or consists of the sequences as set forth in SEQ ID NO: 102.

In also other advantageous embodiments of the present invention, the nucleotide sequence comprises or consists of at least one sequence as set forth in SEQ ID NO: 13, SEQ ID NO: 101 and SEQ ID NO: 102. According to this embodiment, and as described above, in the nucleotide sequence according to the invention, the at least one sequence as set forth in SEQ ID NO: 13, SEQ ID NO: 101 and SEQ ID NO: 102 may be present in several copies which can be either with an even or odd number, preferably an even number, also called a tandem repeat (all direct or all inverted) or any combination of both orientations.

Preferably, the nucleotide sequence of the invention may contain at least 2 copies of at least one of the sequences as set forth in SEQ ID NO: 13, SEQ ID NO: 101 and SEQ ID NO: 102, and more preferably from 2 to 32 copies of at least one of the sequence as set forth in SEQ ID NO: 13, SEQ ID NO: 101 and SEQ ID NO: 102, even more preferably from 2 to 16 sequences, and most preferably from 2 to 8. In a specific embodiment, the nucleotide sequence of the invention contains 2, 3, 4, 5, 6, 7 or 8 copies of at least one of the sequences as set forth in SEQ ID NO: 13, SEQ ID NO: 101 and SEQ ID NO: 102. Each of the sequence as set forth in SEQ ID NO: 13, SEQ ID NO: 101 and SEQ ID NO: 102 in all embodiments described here can be either in the same orientation or not, preferably in the same orientation.

The nucleotide sequence according to the present invention may comprise, or consists of, two tandem copies of each of the sequence as set forth in SEQ ID NO: 13, SEQ ID NO: 101 and SEQ ID NO: 102, or may comprises or consists of one or several four tandem copies of said sequences, viz. 4, 8, 16 and 32.

In a preferred embodiment, in the nucleotide sequence according to the invention, at least one sequence according to formula (I) and/or at least one sequence according to formula (II) is/are upstream to an ATG, and in particular from −800 to −50, preferably from −500 to −50 and more preferably from −300 to −50, of an ATG.

The sequence according to formula (I) and the sequence according to formula (II) as defined above are able to act or are upstream activating sequence of the EYK1 gene promoter and/or of the EYD1 gene promoter.

Therefore, in a second aspect, the present invention is related to an erythritol- and/or erythrulose-inducible promoter sequence functional in yeast, and preferably in *Yarrowia*, and more preferably in *Y. lipolytica* comprising the nucleotide sequence as defined above and a core promoter.

In the present invention, the term "yeast" means any family of yeasts such as *Saccharomyces cerevisiae*, *Saccharomyces* sp., *Schizzosaccharomyces pombe*, *Kluyveromyces lactis*, *Kluyveromyces* sp., *Pichia pastoris* (also named *Komagataella pastoris*), *Pichia finlandica*, *Pichia trehalophila*, *Pichia koclamae*, *Pichia membranaefaciens*, *Pichia minuta* (also named *Ogataea minuta*, *Pichia lindneri*), *Pichia opuntiae*, *Pichia thermotolerans*, *Pichia salictaria*, *Pichia guercuum*, *Pichia pijperi*, *Pichia stiptis*, *Pichia methanolica*, *Pichia angusta* (also named *Hansenula polymorpha*), *Pichia* sp., and *Yarrowia lipolytica*, *Yarrowia* sp., preferably "yeast" means a yeast belonging to the family of Dipodascaceae, and more preferably yeast from the group of the hemiascomycetes such as *Saccharomyces cerevisiae, Schizzosaccharomyces pombe, Kluyveromyces lactis, Pichia pastoris* (also named *Komagataella pastoris*), *Pichia angusta* (also named *Hansenula polymorpha*) and *Yarrowia lipolytica*.

The present invention is preferably related to yeasts of *Yarrowia* family, and especially the yeast *Yarrowia lipolytica*.

The core promoter of the erythritol- and/or erythrulose-inducible promoter sequence according to the invention is a core promoter which is functional in yeast preferably in *Yarrowia*, and more preferably in *Y. lipolytica*. For example, the erythritol- and/or erythrulose-inducible promoter sequence according to the invention may comprise a core promoter selected in the group consisting of TEF core promoter, LEU2 core promoter, EYK1 core promoter, EYD1 core promoter, POX2 core promoter and PAT1 core promoter or the like.

In a preferred embodiment, the erythritol- and/or erythrulose-inducible promoter sequence functional in yeast of the invention further comprising at least one known promoter regulatory sequence, in particular selected in the group consisting of: UAS, TATA box, URS, and preferably at least one of said promoter regulatory sequence from a promoter selected in the group consisting of XPR2, TEF, LEU2, POX2, PAT1 and LIP2 or the like.

In a third aspect, the present invention is related to a construct comprising the erythritol- and/or erythrulose-inducible promoter sequence defined above, operably linked to polynucleotide sequence encoding a gene product to be transcribed from said inducible promoter.

It is well known in the art how a polynucleotide sequence encoding a gene product may be operably linked to a promoter sequence.

A eukaryotic host cell comprising the erythritol- and/or erythrulose-inducible promoter or a construct sequence as defined above is also a fourth aspect of the invention.

Preferably, the eukaryotic host cell comprising said erythritol- and/or erythrulose-inducible promoter or said construct sequence is a yeast host cell, and more preferably a *Yarrowia* host cell and even more preferably *Yarrowia lipolytica* host cell.

In one embodiment, the gene product is a heterologous protein of the yeast. Homologous proteins of the yeast are also comprised in the constructs of the invention.

In one embodiment the construct of the invention comprises sequences allowing its insertion into the chromosome of the host cell. These sequences are particular sequences presenting homology with sequences of the chromosome of the yeast, thus allowing recombination and integration; such elements will be determined by the man skilled in the art. Several copies of the construct can therefore be inserted in the chromosome of the *Yarrowia* yeast.

In this embodiment the construct of the invention may comprises nucleotide sequences denominated zeta, which corresponds to the LTR (Long Terminal Repeats) of the retrotransposon yITy of *Y. lipolytica* allowing its insertion into the chromosome of the host cell. These yITY sequences were described by Schmid-Berger et al. (1994). Zeta sequence flanking expression cassette could be integrated into *Y. lipolytica* genome at random in strain devoid of yITy (Pignede et al, 2000), or at zeta locus in strains containing several copies of YITy and zeta solo (Juretzek et al., 2001), or at zeta docking platform thus allowing random integration in the chromosome of the *Yarrowia* yeast (Bordes et al., 2007; Juretzek et al., 2001; WO 00/012729; WO 2009/098263).

In another embodiment of the invention, the construct is of auto-replicating type, and may furthermore comprise replicating sequences, as well described in the art.

In an advantageous embodiment of the invention, in the host cell which is preferably a yeast host cell, more preferably a *Yarrowia* host cell and even more preferably *Yarrowia lipolytica* host cell, the endogenous gene encoding the L-erythrulose kinase is inhibited. Preferably, the endogenous gene encoding the L-erythrulose kinase is deleted.

In another advantageous embodiment of the invention, in the host cell which is preferably a yeast host cell, more preferably a *Yarrowia* host cell and even more preferably *Yarrowia lipolytica* host cell, the endogenous gene encoding the erythritol dehydrogenase is inhibited. Preferably, the endogenous gene encoding the erythritol dehydrogenase is deleted.

In a fifth aspect, the present invention is related to a method for expressing a gene or producing the encoded protein, comprising the steps of growing a host cell comprising the construct as defined above in an appropriate culture medium more preferably glucose or glycerol and adding at least erythritol and/or erythrulose to the culture medium.

In this aspect of the present invention as in the others concerning a gene product, the gene product can be a heterologous or a homologous protein of interest. The gene product is thus expressed, overexpressed, and the gene product is produced and optionally recovered.

In particular, the gene product may be a therapeutic or prophylactic, a vaccinal, an agronomic, a veterinary, a biotechnological protein. The gene product could be involved in metabolic pathways and preferably a homologous gene product involved in metabolic pathways.

Therapeutic gene product may be enzymes, blood derivatives, hormones, lymphokines, growth factors, neurotransmitters, their precursors of synthesis enzymes, trophic factors, apolipoproteins, tumor suppressor genes, coagulation factors, suicide genes such as thymidine kinase, cytosine deaminase and the like, immunoglobulins and fragments thereof such as Fab, ScFv and the like, RNA ligands, anti-sens, etc.

Vaccinal gene product may be any antigenic peptides, and in particular peptides specific for a virus, for a tumor etc.

As a biotechnological gene product, it may be mentioned enzymes or any protein of interest, for example protein conferring growth ability on starch such as alfa amylase and glucoamylase.

Any gene product useful in metabolic engineering may be used, in particular homologous gene product Involved in the synthesis pathway for the production of compounds such as erythritol or heterologous gene product involved in the synthesis pathway for the production of compounds such as beta carotene, etc.

The construct can further comprise elements allowing the secretion of the protein.

The expression level of the gene product may be regulated by the induction level depending on the media and the inducer concentration.

In a specific embodiment, erythritol or erythrulose are used as inducer and source of carbon for growth. In another embodiment, erythritol or erythrulose are used as inducer only where in the host cell the endogenous gene encoding L-erythrulose kinase is inhibited, preferably deleted, or the endogenous gene encoding the erythritol dehydrogenase is inhibited, preferably deleted.

The method for expressing a gene or producing the encoded protein of the invention may further comprise an additional step for recovering the gene product thus obtained. An additional step for purifying the gene product may also be carried out, in particular with relation to the gene product to be produced. For example, the gene product may be recovered by disrupting the host cell, and further purifying the extract. The person skilled in the art is able to adapt and select the most appropriate recovering and/or purifying method in view of the gene product to be produced.

In this aspect of the invention, all the preferred embodiments described above may be applied in the method for expressing a gene or producing a gene product, i.e. producing the encoded protein, and in particular in *Yarrowia*, and especially in *Yarrowia* in which the endogenous gene encoding the erythrulose kinase or the erythritol dehydrogenase is inhibited, preferably is deleted.

Another aspect of the invention which is described herein is related to the use of EYK1 encoding erythrulose kinase as a catabolic selectable marker for genome editing in any strain bearing a deletion in EYK1 gene and in particular in the non-conventional yeast *Yarrowia lipolytica* bearing a Δeyk1 deletion. Indeed, the inventors have shown that the gene EYK1 is such an efficient catabolic selectable marker, which increase the growth of transformants on selective medium and correctness of the edited genome compared to auxotrophic markers such as URA3 and LEU2 markers. Similarly, the EYD1 encoding erythritol dehydrogenase could be used as a catabolic selectable marker in strain bearing a Δeyd1 deletion.

DRAWINGS

Figure 3:
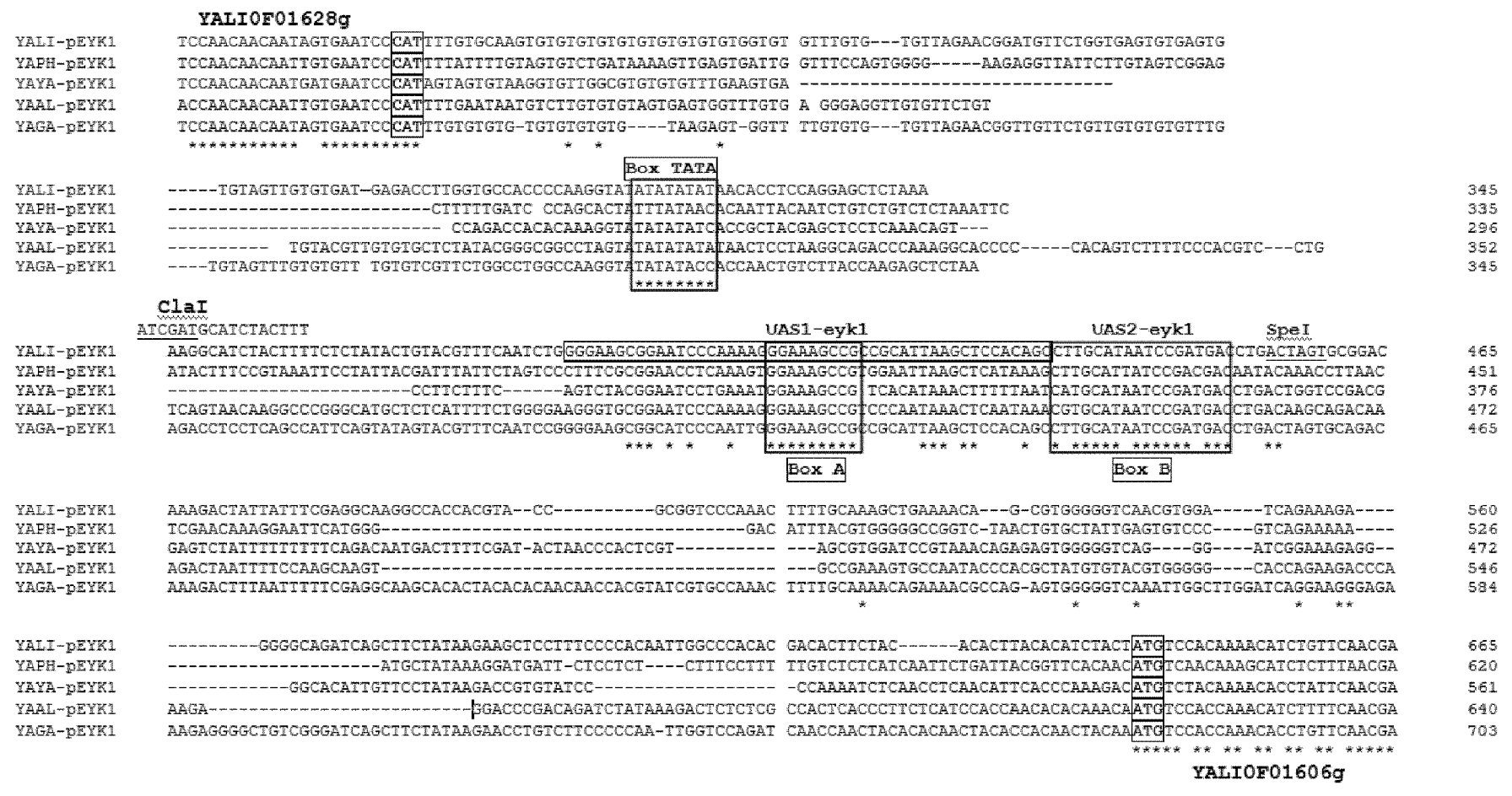

FIG. 3 is a multiple alignment of the intergenic region between YALI0F01628g and YALI0F01606g in *Yarrowia lipolytica* (analysis for the EYK1 promoter region). Conserved nucleic acid in the five species are indicated by a star (*Yarrowia lipolytica* (YALI pEYK1; SEQ ID NO: 78), *Yarrowia phangngensis* (YAPH pEYK1; SEQ ID NO: 79), *Yarrowia yakushimensis* (YAYA pEYK1; SEQ ID NO: 80), *Yarrowia alimentaria* (YAAL pEYK1; SEQ ID NO: 81) and *Yarrowia galli* (YAGA pEYK1; SEQ ID NO: 82)). Two putative regulatory elements for the expression and regulation of the EYK1 gene by erythritol and/or erythrulose are depicted as UAS1-eyk1 and UAS2-eyk1.

Figure 4:
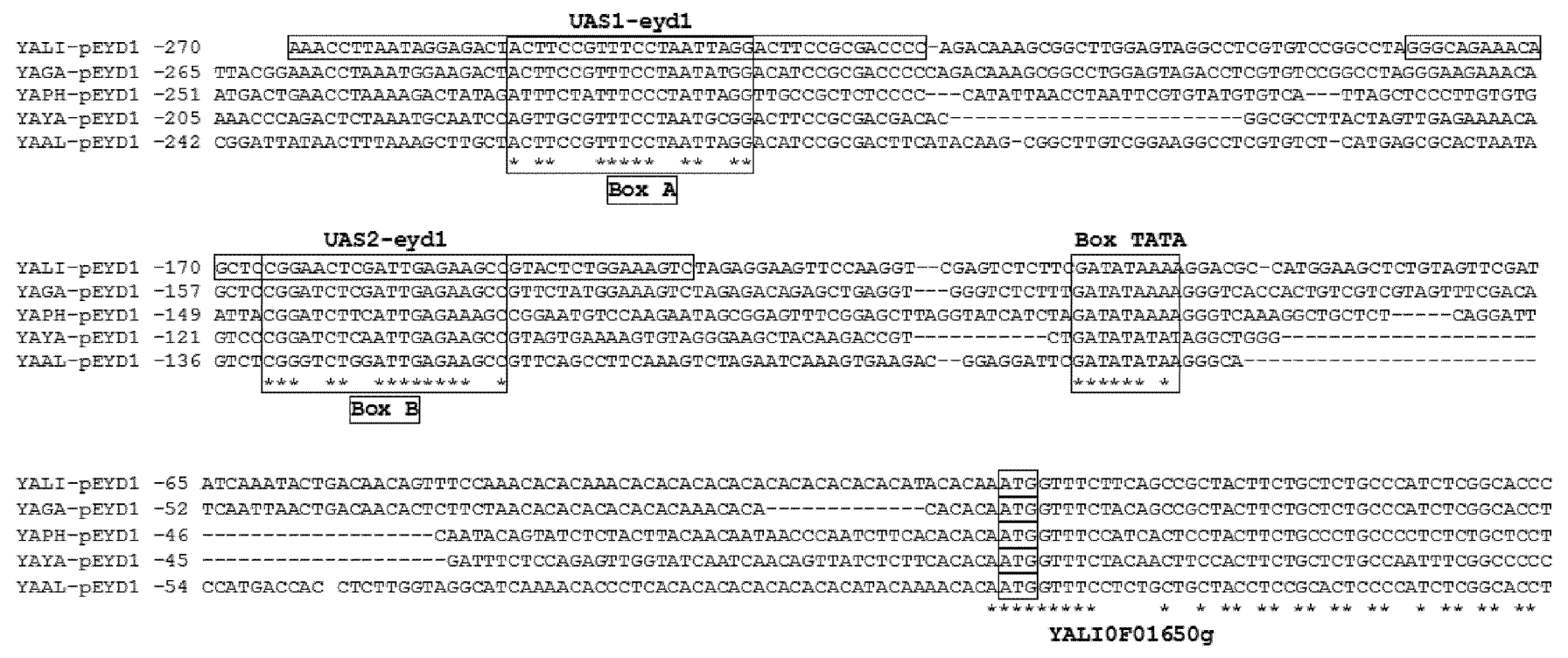

FIG. 4 is a multiple alignment of upstream region of YALI0F01650g in *Yarrowia lipolytica* (analysis of the EYD1 promoter region). Conserved nucleic acid in the five species are indicated by a star (*Yarrowia lipolytica* (YALI pEYD1; SEQ ID NO: 83), *Yarrowia galli* (YAGA pEYD1; SEQ ID NO: 84), *Yarrowia phangngensis* (YAPH pEYD1; SEQ ID NO: 85), *Yarrowia yakushimensis* (YAYA pEYD1; SEQ ID NO: 86) and *Yarrowia alimentaria* (YAAL-pEYD1 (SEQ ID NO: 87)). Two putative regulatory elements for the expression and regulation of the EYD1 gene by erythritol and/or erythrulose are depicted as UAS1-eyd1 and UAS2-eyd1.

Figure 5:
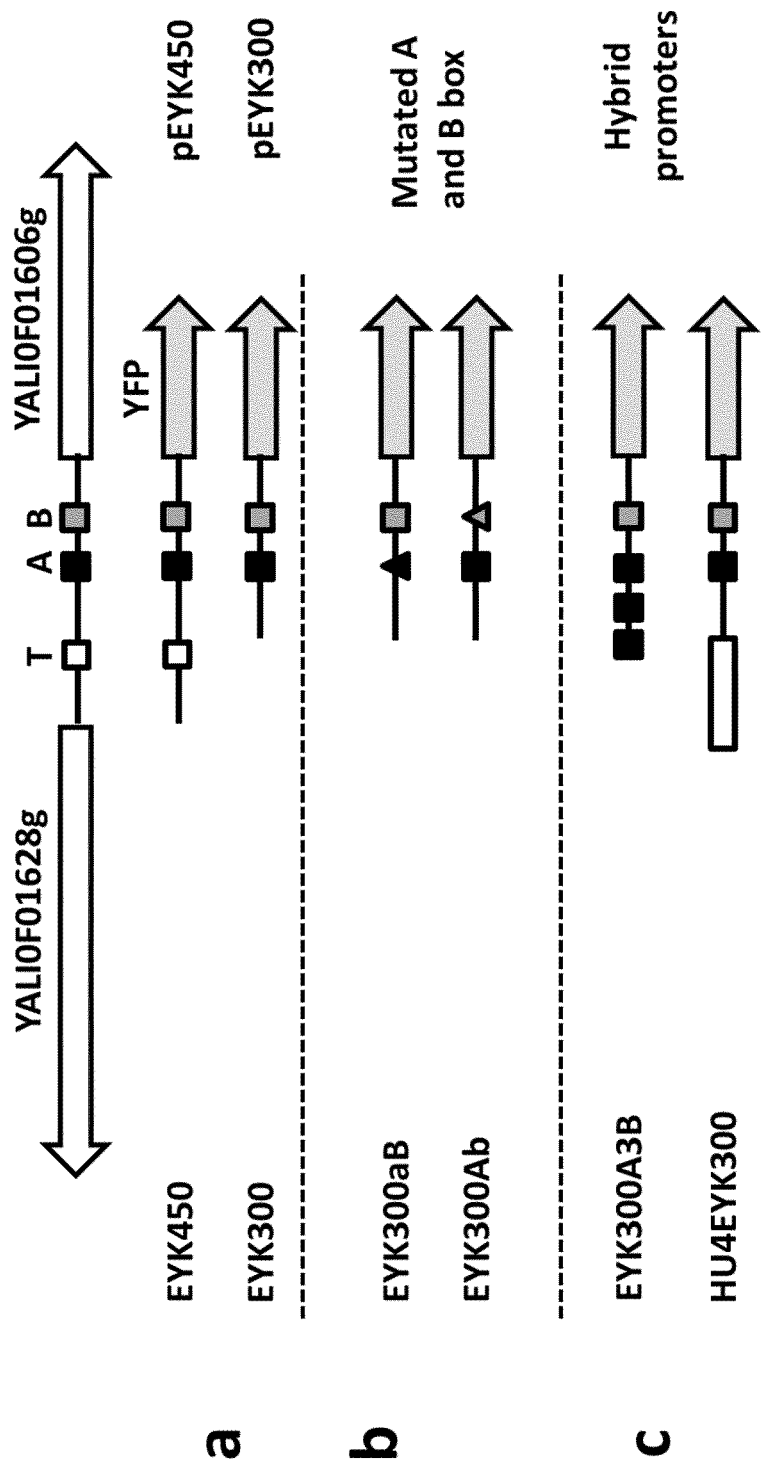

FIG. 5 is a schematic representation of the constructs for studying the promoter based on the genomic locus containing the upstream gene YALI0F01628g and the EYK1 gene, YALI0F01606g. a) the native promoters pEYK450 (including TATA box+native Box A+native Box B) and pEYK300 (including native Box A+native Box B) controlling the expression of YFP; b) the mutated promoters pEYK300aB (including mutated Box A+native Box B) and pEYK300Ab (including native Box A+mutated Box B) controlling the expression of YFP; c) the hybrid promoters pEYK300A3B (including three Box A+native B Box B) and pHU4EYK300 (including 4 tandem copies of $UAS1_{xpr2}$ upstream of pEYK300) controlling the expression of YFP. Symbols are ☐: TATA Box (T), ■: Box A (A), ▦: Box B (B), ▲: mutated Box A, ▴: mutated Box B, ➡: YFP gene, white rectangle: four tandem copies of $UAS1_{xpr2}$.

Figure 6:
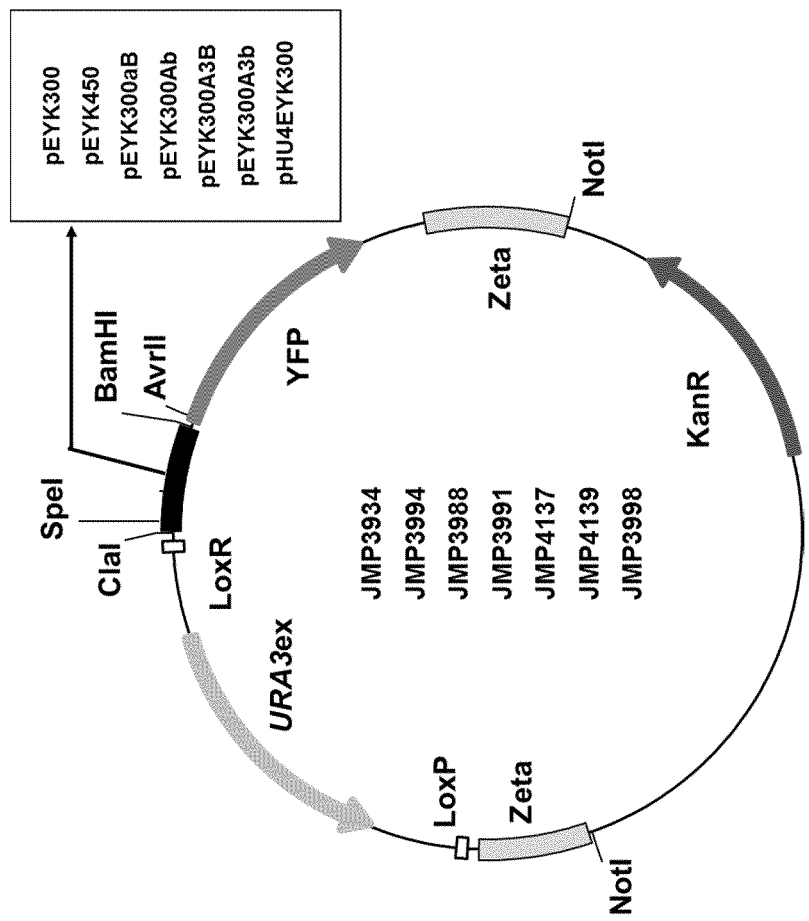

FIG. 6 is a schematic representation of plasmids constructed for studying the promoter. Plasmid pEYK300 contained the yellow fluorescent protein YFP, under the 285 bp promoter region of the EYK gene (erythritol kinase; YALI0F01606g). The vectors contain the zeta sequence for targeting the expression cassette obtained after NotI digestion. KanR and URA3 markers are for selection in *E. coli* and *Y. lipolytica*, respectively. The URA3 is flanked by LoxP/LoxR region for marker rescue (excisable marker URA3ex). JME3934 (pEYK300-YPF); JME3994 (pEYK450-YPF); JMP3988 (pEYK300aB-YPF); JMP3991 (pEYK300Ab-YPF); JMP4137 (pEYK300A3B-YPF)-YPF; JMP4139 (pEYK300A3b-YPF) and JMP3998 (pHU4EYK300-YPF).

Figure 7:
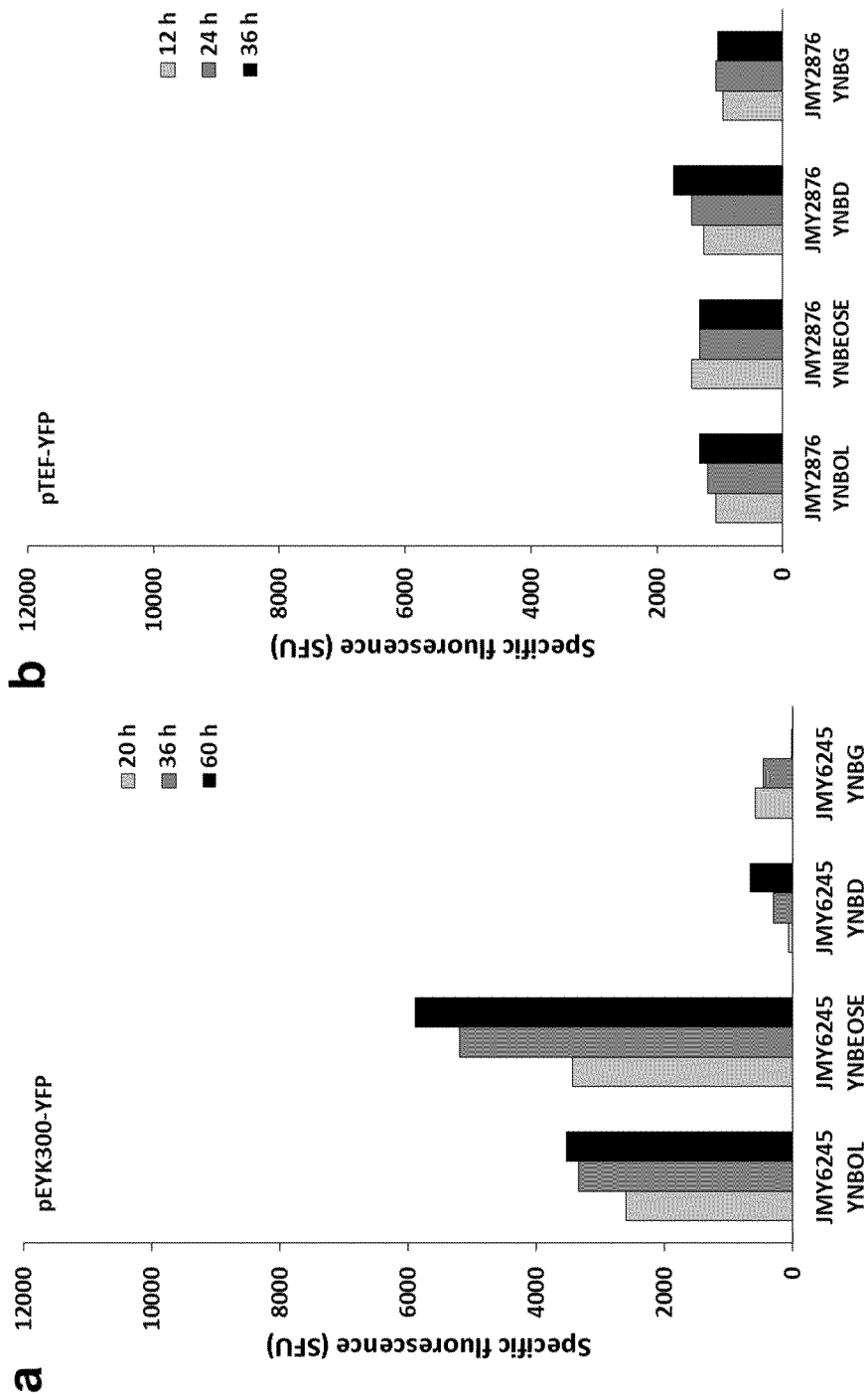

FIG. 7 represents the time course of YFP fluorescence during time depending on culture medium for native EYK1 and pTEF promoters. Specific fluorescence (SFU). a) YFP fluorescence under pEYK300 (JMY6245) and b) pTEF (JMY2878). Growth in minimum media YNB containing 1% of specified carbon source (OL: erythritol, EOSE: erythrulose, D: dextrose, G: glycerol).

Figure 8:
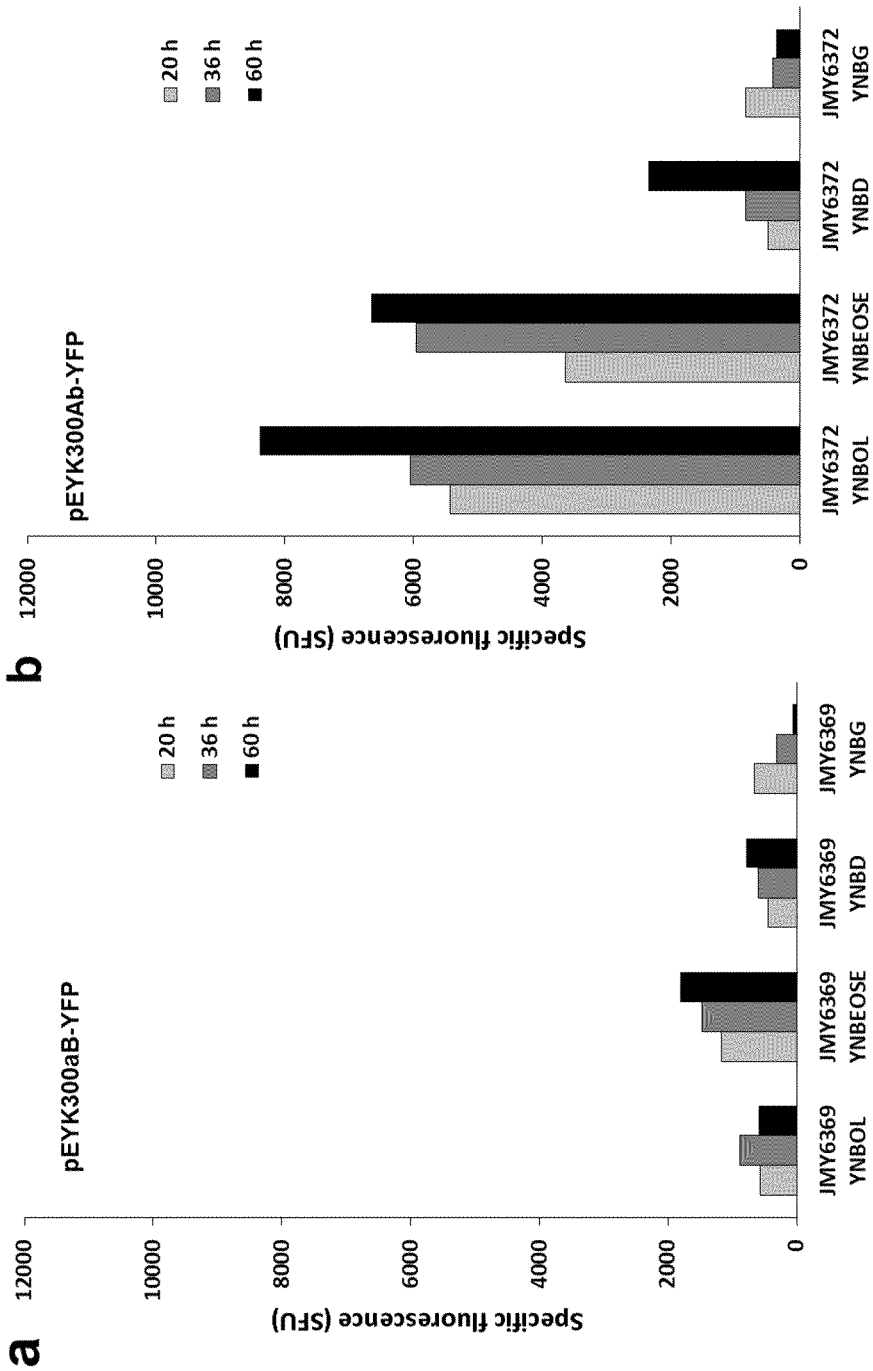

FIG. 8 represents the time course of YFP fluorescence during time depending on culture medium for mutated pEYK300 promoter. Specific fluorescence (SFU, arbitrary unit) corresponding to the expression of YFP under a) Promoter pEYK300 with a mutated Box A; pEYK300aB (JMY6369) and b) Promoter EYK300 with a mutated Box B; pEYK300Ab (JMY6372). Growth in minimum media YNB containing 1% of specified carbon source (OL: erythritol, EOSE: erythrulose, D: dextrose, G: glycerol).

Figure 9:
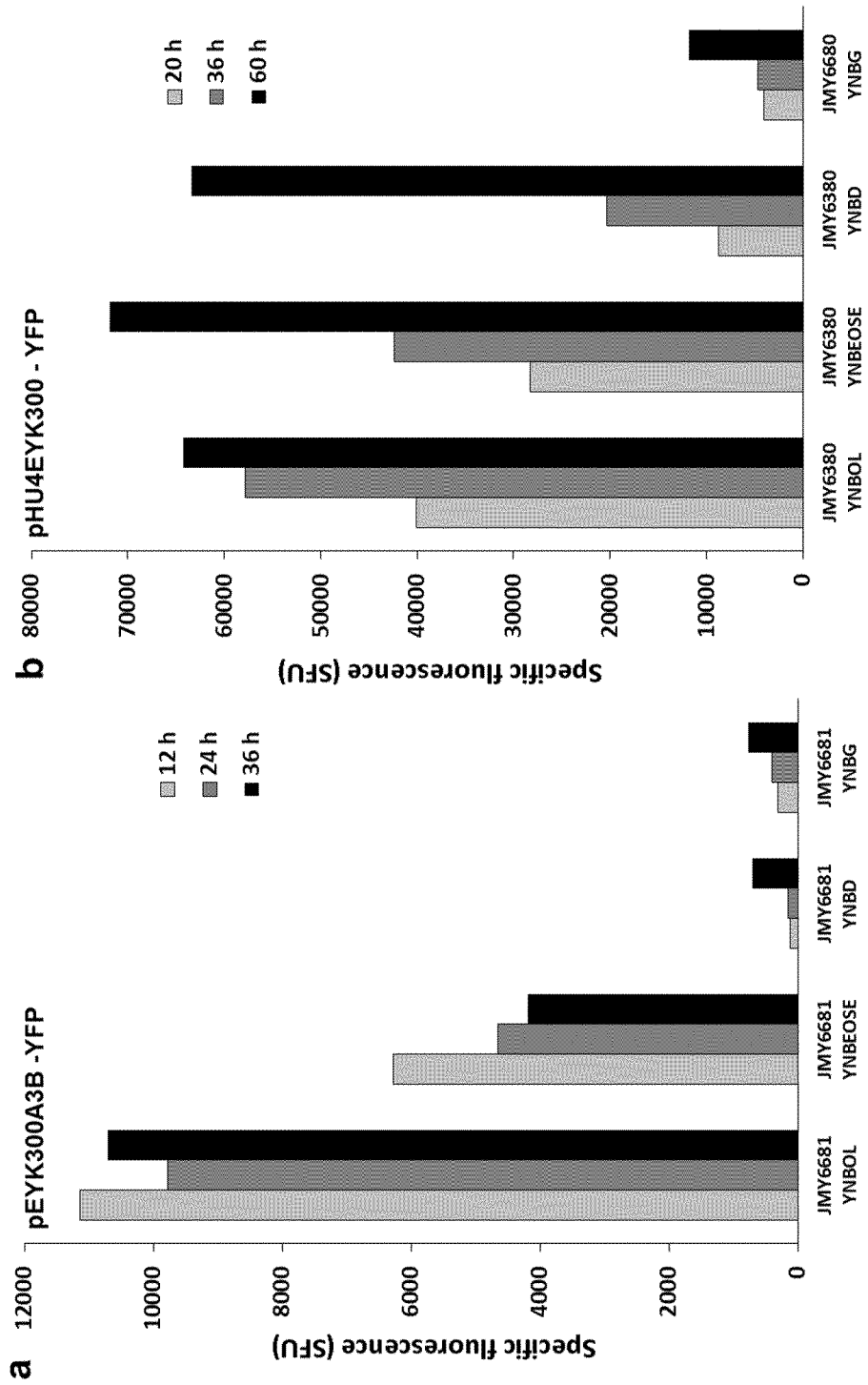

FIG. 9 represents the time course of YFP expression during time depending on media for EYK hybrid promoters. a) Expression of YFP under pEYK300A3B (JMY6681). b) Expression of YFP under pHU4EYK300 (JMY6380). Growth in minimum media YNB containing 1% of the different carbon source. Specific fluorescence (SFU, arbitrary unit).

Figure 10:
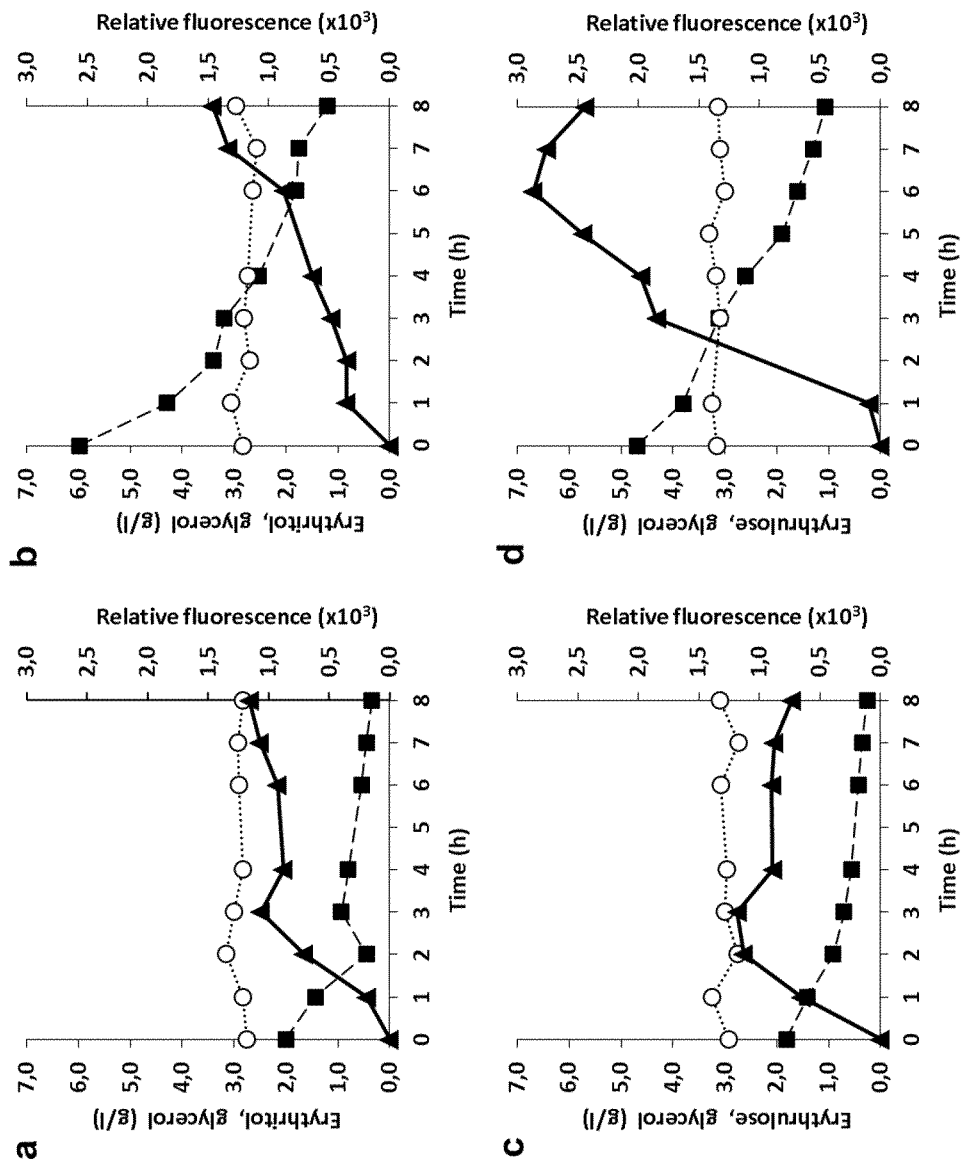

FIG. 10 represents the induction of hybrid EYK1 promoter pHU4EYK300 in continuous culture by erythritol (a, b) and by erythrulose (c, d). Erythritol or erythrulose and glycerol concentrations in the culture medium, and relative fluorescence of the cells during chemostat of JMY6380 (pHU4EYK300) on YNB-glycerol medium (1% glycerol). a) Induction with a pulse of 0.2% of erythritol. b) Induction with a pulse of 0.6% of erythritol. c) Induction with a pulse of 0.2% of erythrulose. d) Induction with a pulse of 0.6% of erythrulose. Time 0 corresponds to the time of the pulse. Symbols are: ■: erythritol or erythrulose; ○: glycerol; ▲: relative fluorescence (×10³).

Figure 11:
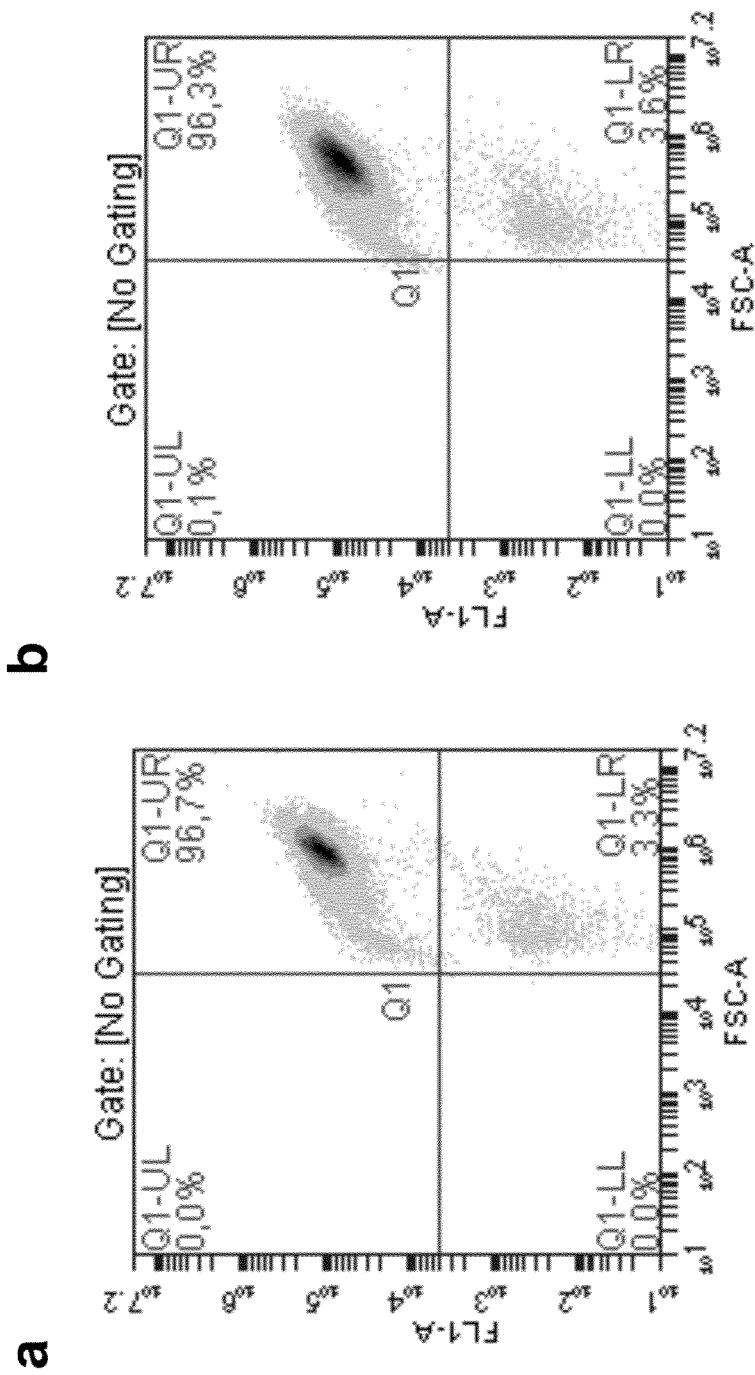

FIG. 11 represents the influence of dilution rate on the induction of hybrid EYK1 promoter pHU4EYK300 in continuous culture by erythritol. FL1-A/FSC-A cytograms corresponding to the chemostat of JMY6380 (pHU4EYK300) on YNB-erythritol medium (1% erythritol). The horizontal line at 4×10³ FU represents the limit between induced cells (quadrant Q1-UR of the cytogram) and non-induced cells (quadrant Q1-LR of the cytogram). Cytograms are representative of two independent cultures, and are the result of the analysis of 40,000 cells. a) Cytogram of the equilibrium cell population cultivated at a dilution rate of D=0.16 h⁻¹. b) Cytogram of the equilibrium cell population cultivated at a dilution rate of D=0.08⁻¹.

Figure 12:
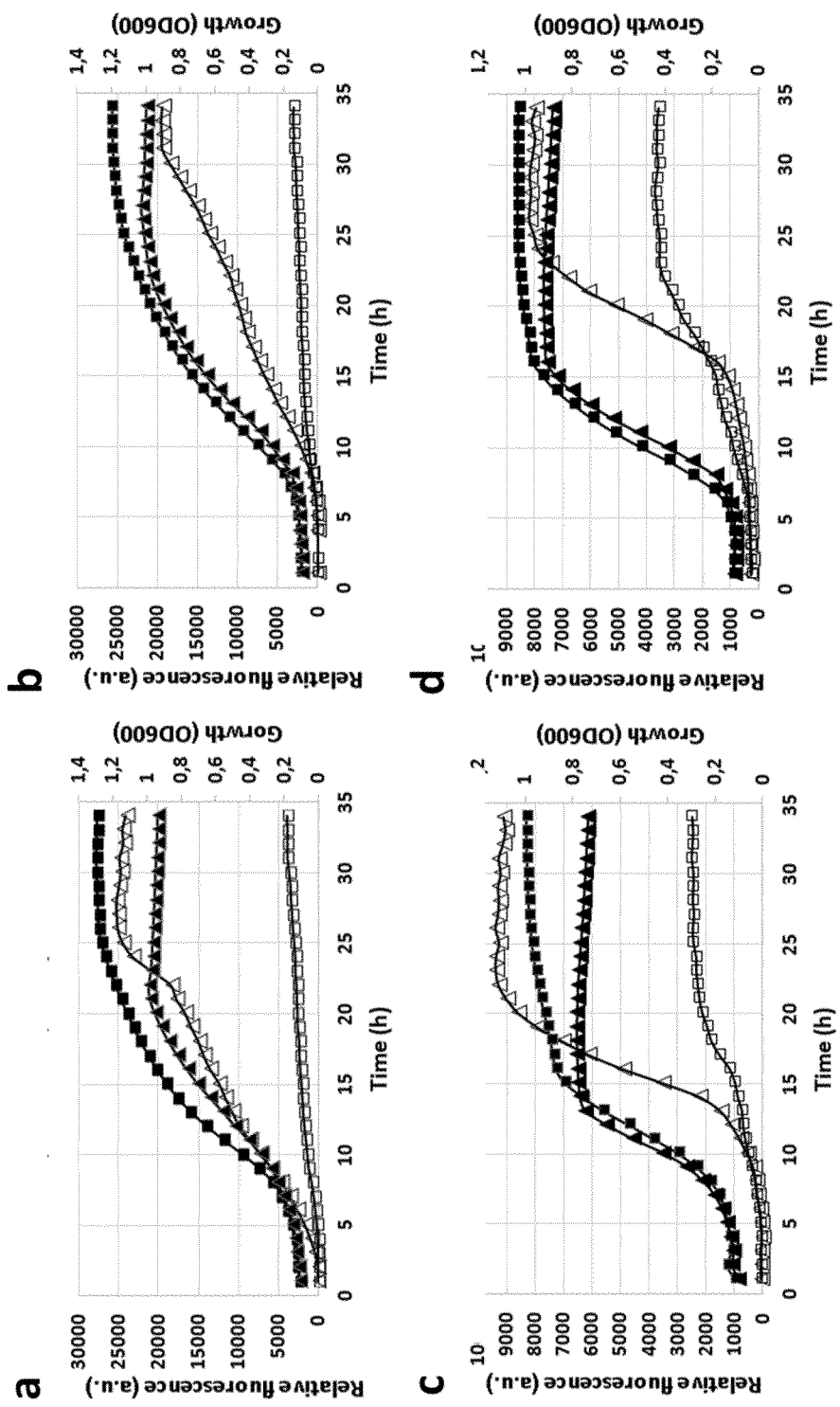

FIG. 12 represents the time course of YFP fluorescence during time in wild-type and Δeyk1 strain under pEYK300. YFP fluorescence under pEYK300 in wild-type and Δeyk1 mutant, JMY6245 and JMY6638, respectively. Growth in minimum media YNB containing 0.25% of carbon source and 0.25% of inducer. a) Glucose and erythritol. b) Glycerol and erythritol. c) Glucose and erythrulose. d) Glycerol and erythrulose. Symbols are wild-type (square) and mutant (triangle). Growth (full symbols) and fluorescence (empty symbols).

Figure 13:
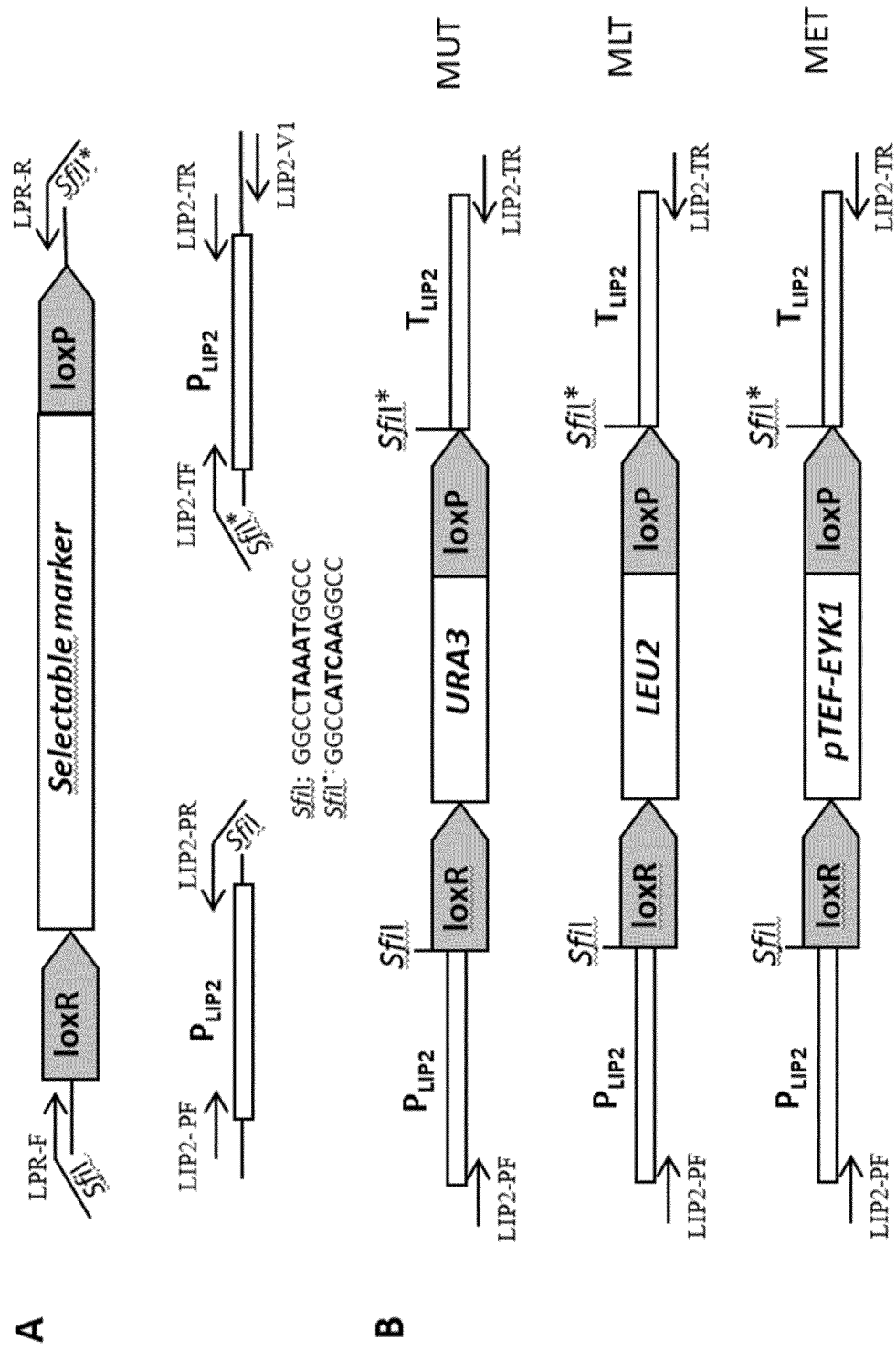

FIG. 13 is a schematic representation of the construction of disruption cassettes by directed fragment assembly based on SfiI recognition sequence (SRS) and PCR amplification. (A) Amplification of the selectable marker, $P_{LIP2}$ and $T_{LIP2}$ fragments, in order to introduce compatible SRS. The selectable markers flanked by loxP-loxR sequences were amplified with primer pair LPR-F/LPR-R, $P_{LIP2}$ fragment was amplified with primer pair LIP2-PF/LIP2-PR, and $T_{LIP2}$ fragment was amplified with primer pair LIP2-TF/LIP2-TR. The sequences of inner nucleotides of SRS (SfiI—SEQ ID NO: 57 and SfiI*—SEQ ID NO: 58, respectively) are highlighted in bold. (B) Schematic representation of the MUT, MLT and MET cassettes. SfiI-URA3-SfiI*, SfiI-LEU2-SfiI* and SfiI-pTEF-EYK1-SfiI* fragments were ligated with $P_{LIP2}$-SfiI and SfiI*-$T_{LIP2}$ fragments to generate the MUT, MLT and MHT cassettes, respectively. The final disruption cassettes were amplified by PCR using primer pair LIP2-PF/LIP2-TR.

Figure 14:
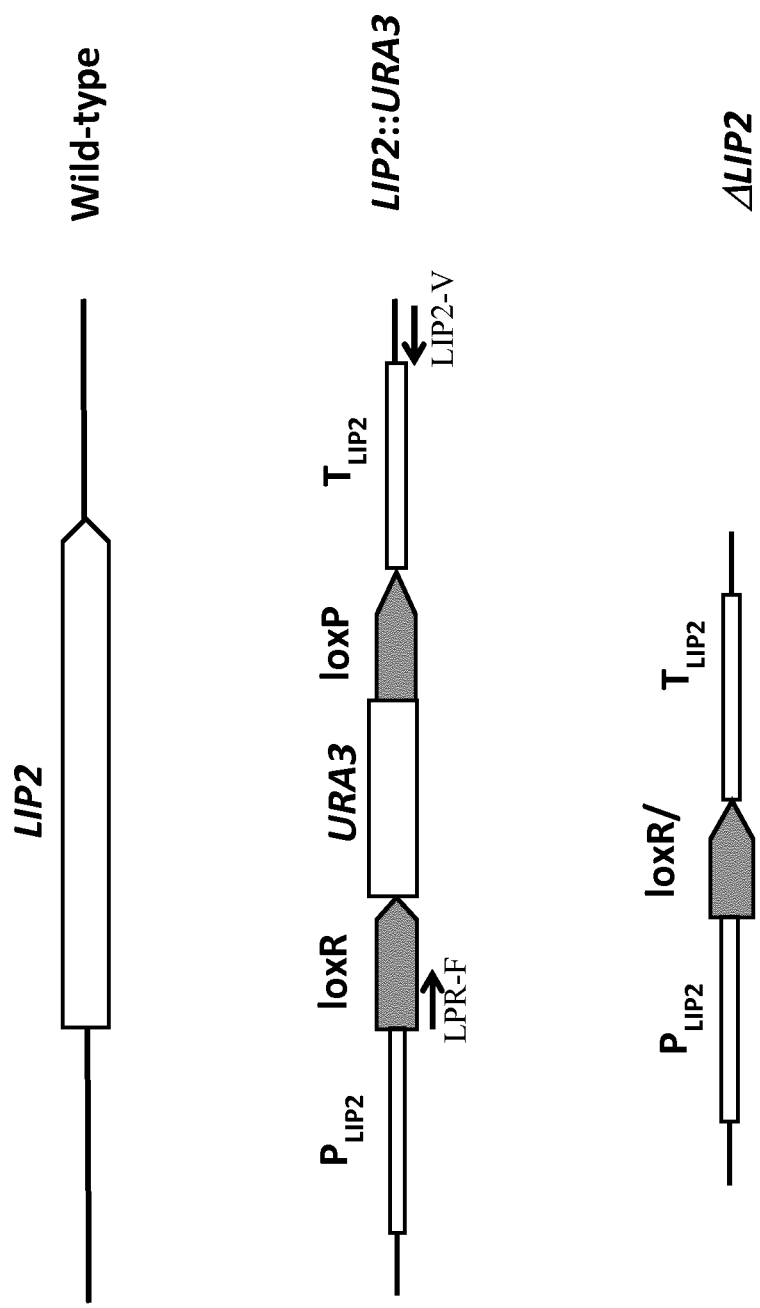
Figure 14:
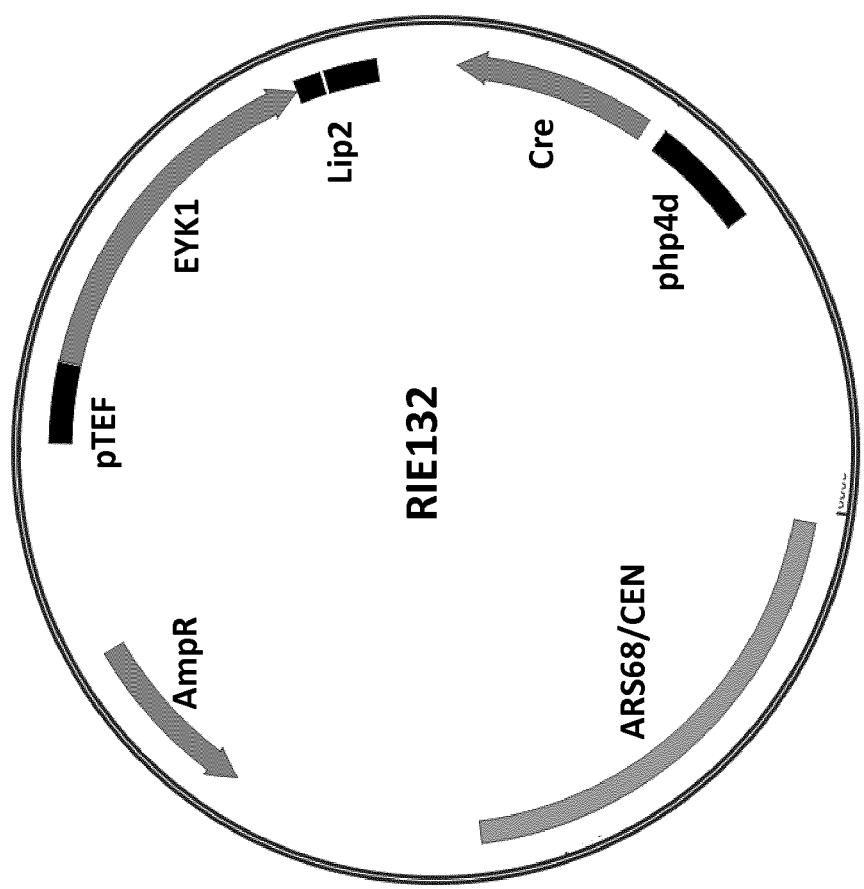

FIG. 14 is the verification of URA3 marker excision in strain RIY201 (lip2::URA3). (A) Schematic representation of the LIP2 locus in strain RIY201 (Po1d lip2::URA3) and RIY203 (Δlip2). (B) The replicative RIY132 plasmid containing the cre gene under the hp4d promoter and the catabolic selectable marker pTEF-EYK1.

Figure 15:
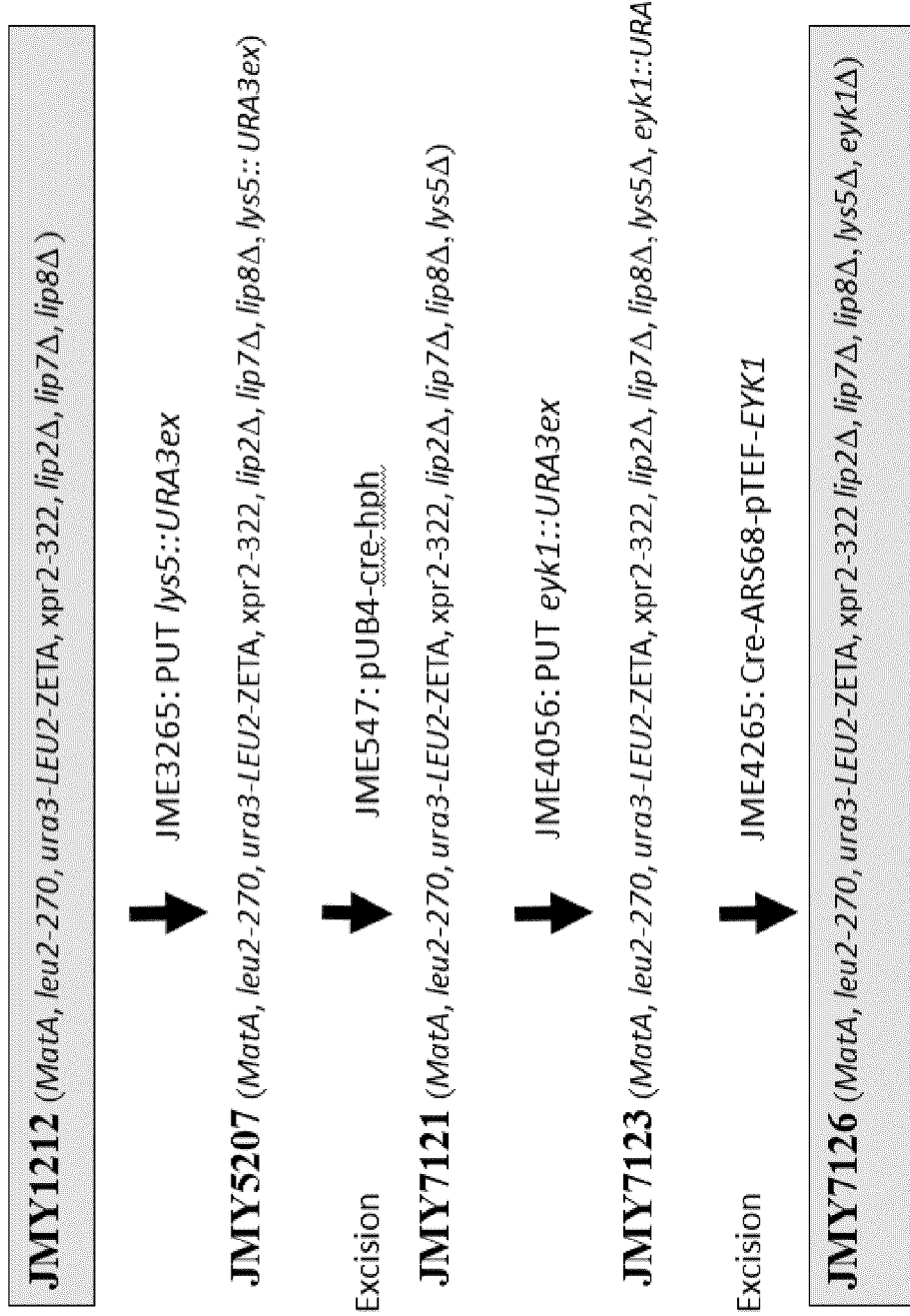

FIG. 15 is a schematic representation of Y. lipolytica strain JMY7126 construction. The auxotrophic strain JMY1212 (Bordes et al., 2007) was used as parental strain. LYS5 and EYK1 genes were successively disrupted with the corresponding disruption cassette from JMP3265 and JMP4056, respectively. In turn to recover URA3 and EYK1 auxotrophies, strains were transformed with replicative plasmids containing the CreLox recombinase with either the hygromycin marker (pUB4-CRE) or the catabolic selectable EYK1 marker (pTEF-EYK1_hp4d-Cre).

Figure 16:
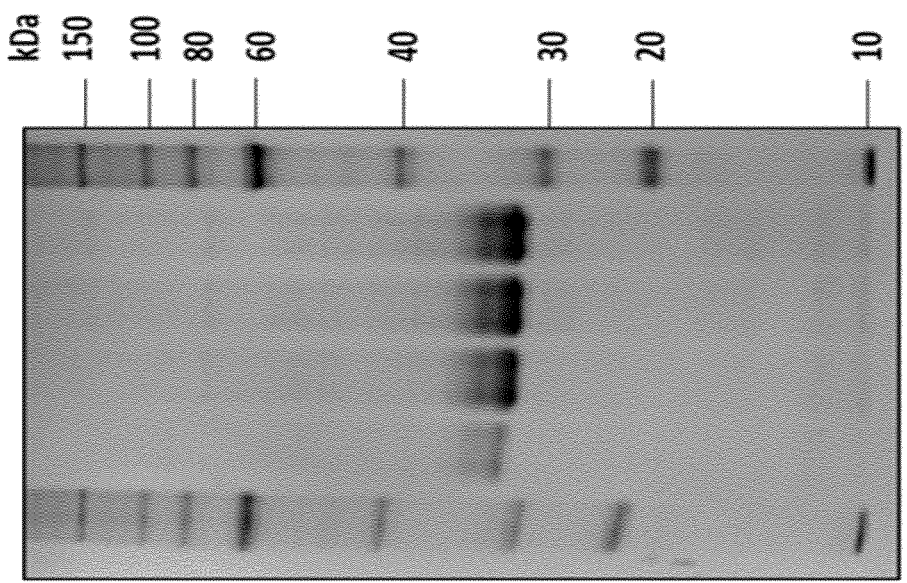
Figure 16:
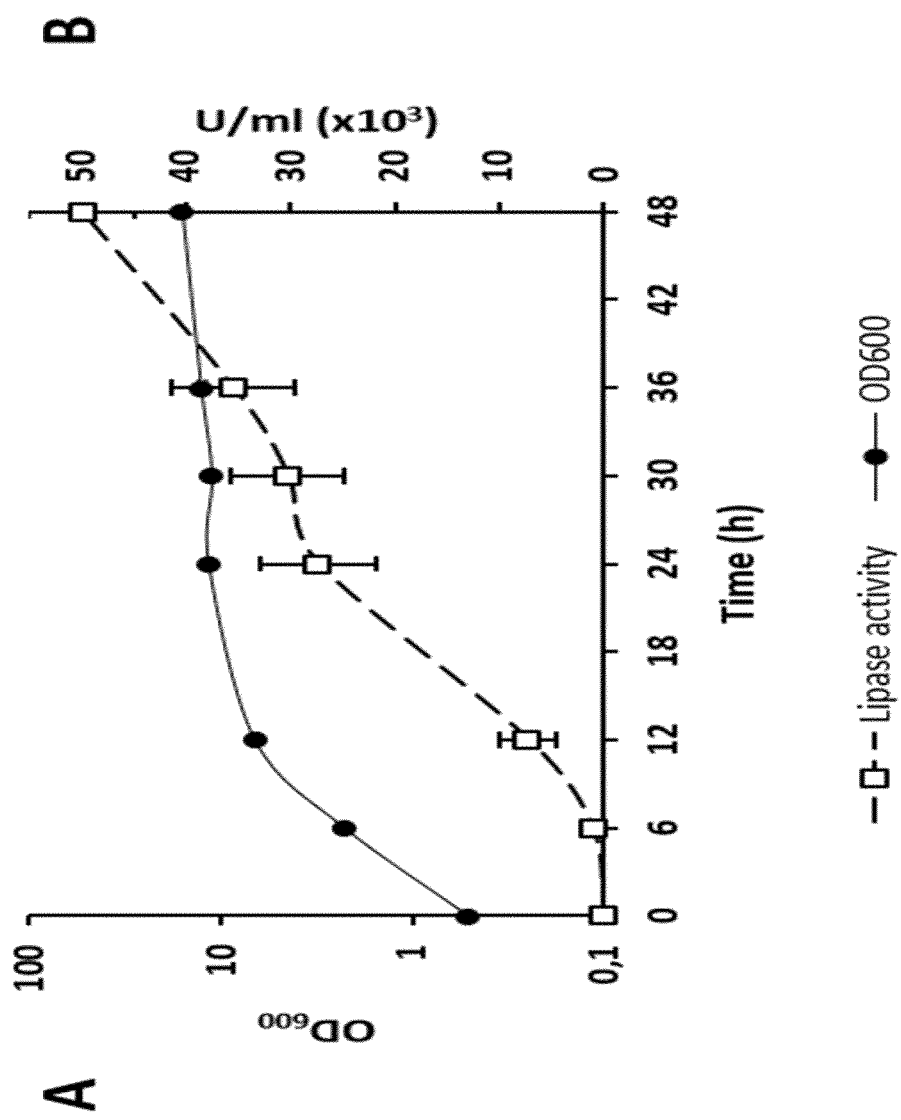

FIG. 16 represents the production of the lipase CalB during fed-batch fermentation of strain JMY7240 cultivated for 48 h in a 2 L bioreactor (YNBE medium and glycerol feed). Panel A: Growth curve and lipase activity of strain JMY7240. Panel B: Extracellular lipase accumulation in the culture medium. Samples (5 μl of crude supernatant) were resolved by SDS-PAGE. Lanes 2 to 5 correspond to samples collected after 12, 24, 36 and 48 h of culture, respectively. Lanes 1 to 6 correspond to pre-stained protein marker IV. Protein sizes are indicated on the right-hand side.

Figure 17:
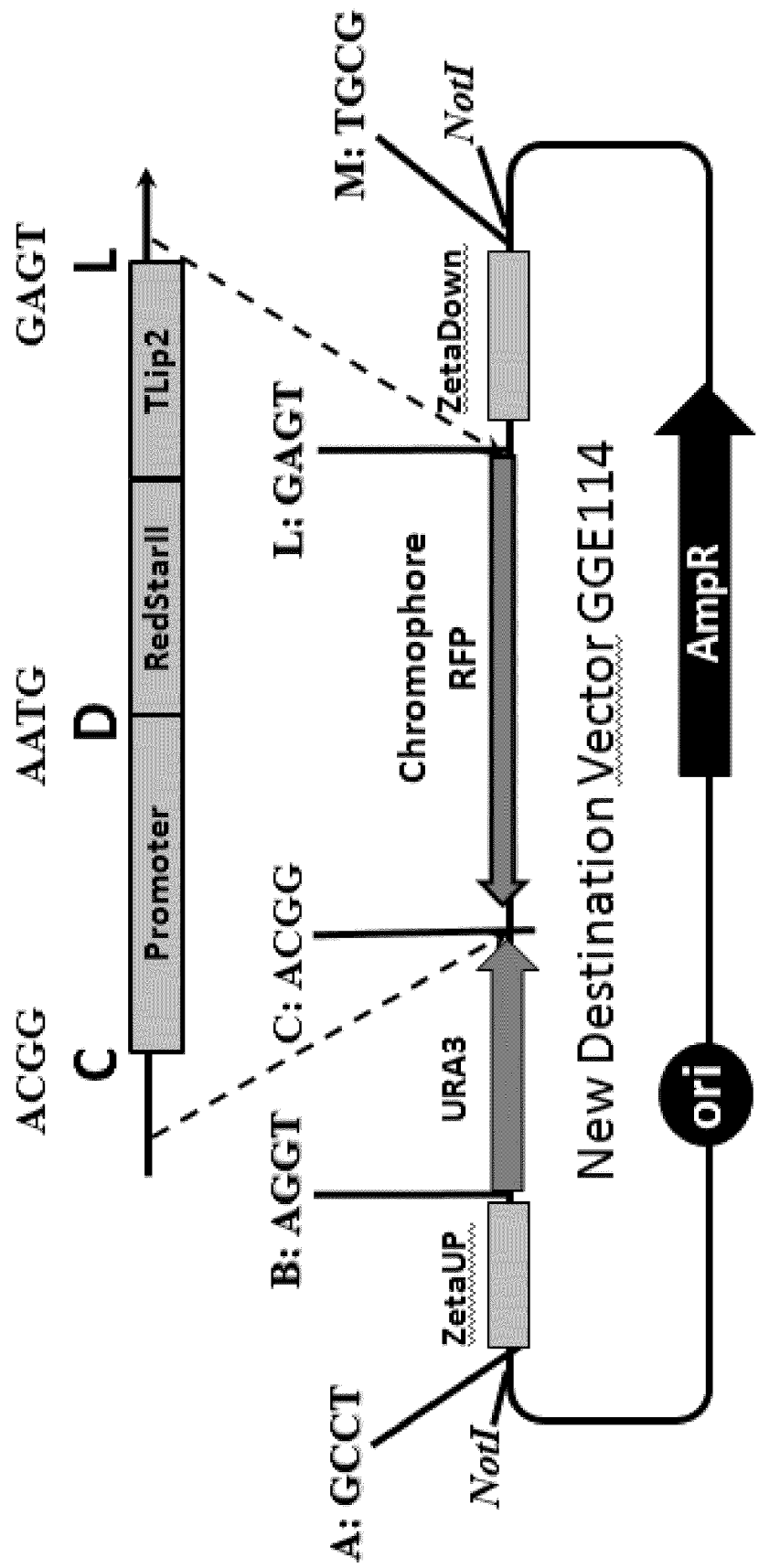

FIG. 17 is a schematic representation of Golden Gate assembly strategy for promoter study. The Golden Gate bio-bricks containing the promoter with the overhang C and D were assembled together with the fragment carrying the RedStarII with the Lip2 terminator with the overhangs D and L into the new destination vector GGE114. The assembled vector contains the zeta region for expression cassette integration, the URA3 marker for Y. lipolytica selection and the RedStarII as reporter gene in Y. lipolytica. The chromophore red fluorescent protein RFP is excised upon successful cloning of the Biobricks. The expression cassette is released upon NotI digestion.

Figure 18:
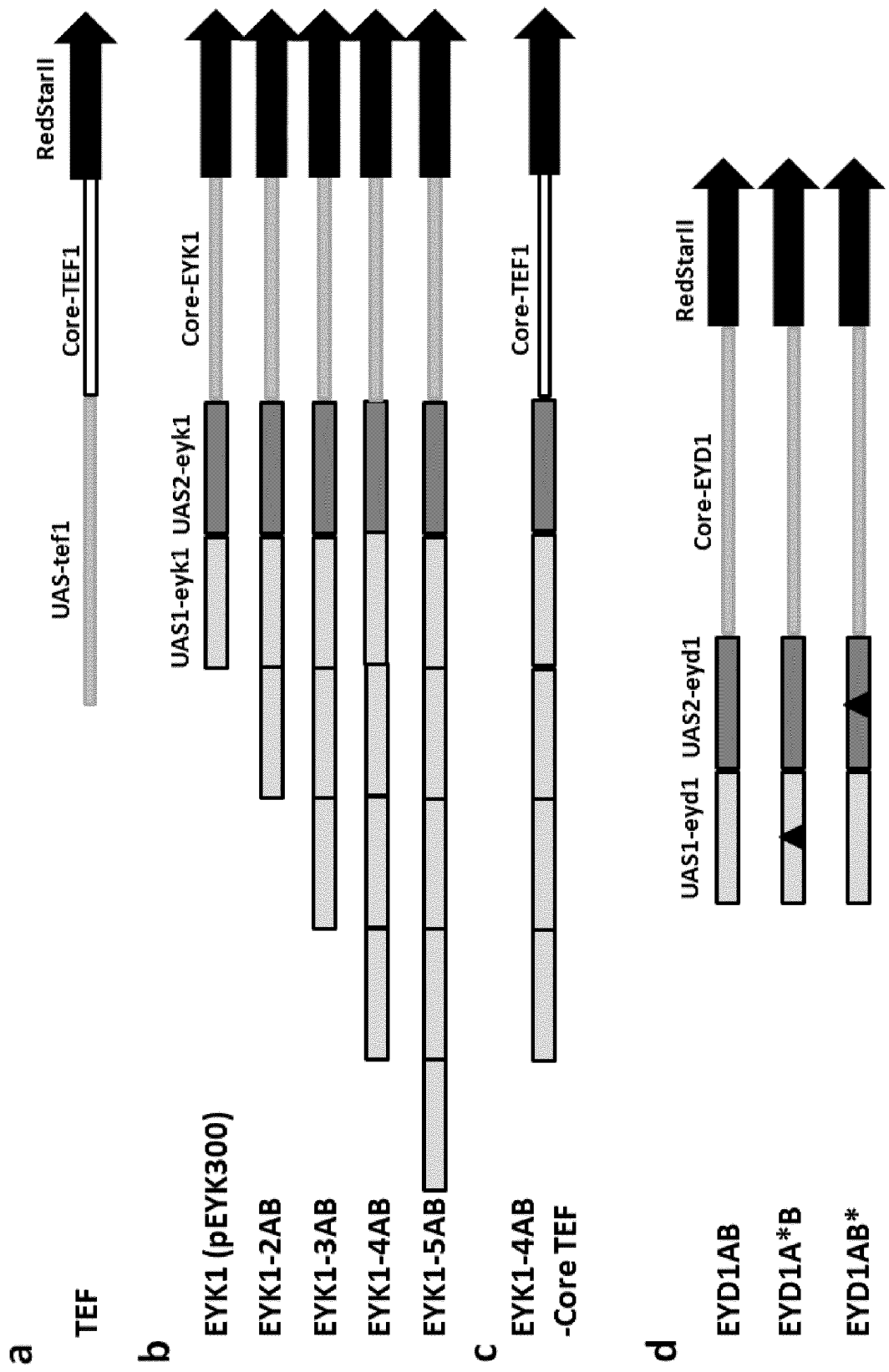

FIG. 18 is a schematic representation of plasmids constructed for studying the promoter. a) the native 361 bp pTEF promoter carrying the UAS tef1 and the 93 bp Core TEF controlling the expression of RedStarII, b) the native 303 bp EYK1 (pEYK300) promoter (UAS1-eyk1 containing the native Box A+UAS2-eyk1 containing the native Box B+Core EYK1) and the hybrid promoters pEYK1 promoters carrying from 2 to 5 tandem repeats of UAS1-eyk1 ($UAS1_{EYK1}$); EYK1-2AB (2 UAS1-eyk1+UAS2-eyk1 ($UAS2_{EYK1}$)+Core EYK1), EYK1-3AB (3 UAS1-eyk1+UAS2-eyk1+Core EYK1), EYK1-4AB (4 UAS1-eyk1+UAS2-eyk1+Core EYK1), EYK1-5AB (5 UAS1-eyk1+UAS2-eyk1+Core EYK1) controlling the expression of RedStarII, c) the hybrid promoters EYK1-4AB-Core TEF (4 UAS1-eyk1+UAS2-eyk1+Core TEF1), controlling the expression of RedStarII, d) the wild type EYD1 promoter (EYD1AB) and mutated EYD1 promoters within the UAS1-eyd1 (EYD1A*B; including mutated Box A+native Box B) and the UAS2-eyd1 (EYD1AB*; including native Box A+mutated Box B) controlling the expression of RedStarII.

EXAMPLES—MATERIALS AND METHODS

Strain and Medium Composition

All the strains used in this study are listed in Table 1. The Y. lipolytica strains derived from the wild-type Y. lipolytica W29 strain (ATCC20460). The auxotrophic derivative Po1d (Leu⁻ Ura⁻) was previously described by Barth and Gaillardin (1996). Strain JMY1212 (MatA ura3-302 xpr2-322, LEU2, zeta platform, derived from Po1d) was used as the basis for promoter study in this study, the derivative strain JMY7126 (MatA ura3-302 xpr2-322, Δlys5, Δeyk1, LEU2, zeta platform, derived from JMY1212) carrying a deletion of EYK1 was also used to see inducible expression of promoter in strain unable to use erythritol as a carbon source. Escherichia coli strain DH5α was used for hosting and amplification of recombinant plasmid DNA. The media and growth conditions for E. coli were as described in Sambrook et al. (1989). YPD and YNB medium together with growth conditions for Y. lipolytica have been previously described by Barth and Gaillardin (1996). To meet auxothrophic requirement, uracil (0.1 g/L), lysine (0.8 g/L), and leucine (0.1 g/L) were added in culture medium when necessary. Casamino acids, (0.2% Bacto Casamino Acids, Difco, Paris, France), were added for bioreactors culture for faster growth rate. Growth of Y. lipolytica were performed in baffled 250 mL flask and incubated at 28° C. at 160 rpm. YNB medium was supplemented with carbon source as follows: 10 g/L glucose (YNBD); 10 g/L glycerol (YNBG); 10 g/L erythritol (YNBOL); 10 g/L erythrulose (YNBOSE); 1 g/L glycerol, 10 g/L erythritol, 0.5 g/L yeast extract and 0.5 g/L peptone (YNBE). Growth of Δeyk1 strains in microplates were performed in YNB medium with 2.5 g/L glucose or 2.5 g/L glycerol as carbon source and 2.5 g/L erythritol or 2.5 g/L erythrulose as inducer. YNBDETo is an YNB medium with 10 g/L glucose, 10 g/L erythritol, 5 g/L tributyrin and 1.5% agar.

Culture in Fed-Batch Bioreactor

Bioreactor cultures were performed in duplicate in a 2-L Biostat B-Twin fermentor (Sartorius) containing 1 L of medium and kept at 28° C. Stirrer speed was set to 800 RPM, and the aeration rate was 1 L/min. The pH was set at 6.8 and automatically maintained by the addition of 20% (w/v) NaOH or 40% (w/v) $H_3PO_4$ when necessary. Glycerol (56.9 g/L solution) was fed for 24 h at a flow rate of 0.4 g/L·h, then at a flow rate of 0.8 g/L·h for an additional 24 h. Yeast cultures were inoculated at an initial optical density at 600 nm of 0.5. Cell growth was monitored by optical density at 600 nm (OD600). Cell dry weight (CDW) was determined by using the relation OD600=0.29 gCDW correlation.

TABLE 1

List of strains and plasmids used

| Strain or plasmid* | Genotype or other relevant characteristics | Source or reference |
|---|---|---|
| *E. coli* | | |
| DH5α | φ80dlacZΔm15, recA1, endA1, gyrA96, thi-1, hsdR17 ($r_k$−, $m_k$+), supE44, relA1, deoR, Δ(lacZYA-argF)U169 | Promega |
| pCR4Blunt-TOPO ® | Cloning vector, kanamycin | Invitrogen |
| pJET 1.2 | Cloning vector, ampiciline | Thermo scientific |
| pUC57 | GeneScript Biotech donor vector | GeneScript Biotech |
| GGE020 | pCR4Blunt-TOPO-T1-3Lip2 | (Celińska et al., 2017) |
| GGE077 | pCR4Blunt-TOPO-G1-RedstarII | (Celińska et al., 2017) |
| GGE085 | pCR4Blunt-TOPO-pTEF1 | (Celińska et al., 2017) |
| GGE104 | pCR4Blunt-TOPO-pEYK1-3AB | |
| GGE114 | pSB1A3-ZetaUP-URA3-RFP-ZetaDOWN | (Celińska et al., 2017) |
| GGE0130 | pCR4Blunt-TOPO-pEYK1-2AB | This work |
| GGE0132 | pCR4Blunt-TOPO-pEYK1-4AB | This work |
| GGE140 | pCR4Blunt-TOPO-pEYD1AB | This work |
| GGE172 | pCR4Blunt-TOPO-pEYD1A*B | This work |
| GGE174 | pCR4Blunt-TOPO-pEYD1AB* | This work |
| GGE238 | pCR4Blunt-TOPO-pEYK1 | This work |
| GGE250 | pCR4Blunt-TOPO-pEYK1-5AB | This work |
| RIE132 (RIP132) | Cre-EYK1 (2.2 kb pTEF-EYK1 fragment in pRRQ2) | This work |
| FCP007 | pJET 1.2-pEYK300; ClaI-BamHI | This work |
| JME461 | pRRQ2 (Cre ARS68 LEU2) | Richard et al. (2001) |
| JME507 | JMP113 (URA3ex marker) | Fickers et al. (2003) |
| JME508 | JMP114 (LEU2ex marker) | Fickers et al. (2003) |
| JME547 | pUB4-CRE | Fickers et al. (2003) |
| JME803 | JMP62-pPOX2-URA3ex | Haddouche et al. (2010) |
| JME1046 | pTEF-URA3; JMP62 type vector with pTEF promoter | This work |
| JME1427 | JMP62-pTEF-YFP-LEU2ex | B Treton, unpublished |
| | JMP62-php4d-YFP-URA3ex | B Treton, unpublished |
| JME2027 | pCR4Blunt-TOPO - ClaI-4UAS1xpr2-BstBI | Dulermo et al., (2017) |
| JME3265 | JMP62-LYS5ex | unpublished |
| JME3267 | PUT-lys5, PLYS5-UR43ex-TLYS5 | This work |
| JME3739 | pTEF-CalBop-URA3ex, CalB expressed under the pTEF promoter (15ACCYRP__1762990__pJME1046-CalB) | This work |
| JME3934 (FCP013) | JMP62-pEYK300-YFP-URA3ex | This work |
| JME3994 (JMP3994) | JMP62-pEYK450-YFR-UR43ex | This work |
| JME3988 (JMP3988) | JMP62-pEYK300aB-YFP-URA3ex | This work |
| JME3991 (JMP3991) | JMP62-pEYK300Ba-YFP-URA3ex | This work |
| JME3998 (JMP3998) | JMP62-pHU4-EYK300-YFP-URA3ex | This work |
| JME4056 | pGEM6-easy-cre-EYK1 | Vandermies et al., 2017 |
| JME4123 | PUC57-pEYK300A3B | GenScript, Hong-Kong |
| JME4124 | PUC57-pEYK300A3b | GenScript, Hong-Kong |
| JME4137 (JMP4137) | JMP62-pEYK300A3B-YFP-URA3ex | This work |
| JME4139 (JMP4139) | JMP62-pEYK300A3b-YFP-URA3ex | This work |
| JME4265 (RIE132) | Cre-ARS68-pTEF-EYK1 | Vandermies et al. 2017 |
| JME4266 | pEYK3AB-URA3ex; JMP62 type vector with pEYK3AB promoter | This work |

TABLE 1-continued

List of strains and plasmids used

| Strain or plasmid* | Genotype or other relevant characteristics | Source or reference |
|---|---|---|
| JME4230 | pHu8-URA3ex; JMP62 type vector with pHu8 promoter | This work |
| JME4365 | pEYK3AB-CalBop-URA3ex; JMP62 type vector with pEYK3AB promoter | This work |
| JME4384 | pEYK3AB-CalBop-LYS5ex; JMP62 type vector with pEYK3AB promoter | This work |
| JME4417 | pUC57-EYK1-4AB-coreTEF | This study |
| *Y. lipolytica* | | |
| W29 | MatA, CLIB89, ATCC20460, Wild-type French strain | Barth & Gaillardin (1996) |
| Po1d (JMY195) | MatA ura3-302 leu2-270 xpr2-322 URA3ex LEU2 deleted for the extracellular protease AEP encoded by XPR2 gene | Barth & Gaillardin (1996) |
| RIY146 | Po1d eyk1::LEU2, Ura+ | This work |
| RIY176 | Po1d Δeyk1, Ura+ Leu+ | This work |
| RIY180 (JMY6637) | RIY176 + pEYK300-YFP-LEU2ex (Ura+ Leu+) | This work |
| RIY201 | Po1d lip2::URA3, Leu+ | This work |
| RIY203 | Po1d Δlip2 | This work |
| RIY132 | ARS68/CEN php4d-Cre pTEF-EYK1 | This work |
| RIY212 | Po1d eyd1::URA3ex | This work |
| RIY225 | Po1d Δeyd1 | This work |
| JMY330 | Po1d, Ura+ | Haddouche et al, (2010) |
| JMY1212 | MatA, leu2-270, ura3-LEU2-ZETA, xpr2-322, Δlip2, Δlip7, Δlip8, deleted for the three lipases Lip2, Lip7 and Lip8 and the extracellular lipase AEP, zeta-LEU2 platform at the URA3 locus | Bordes et al., (2003) |
| JMY2101 | Po1d, Leu+ | Dulermo et al. (2017) |
| JMY2876 | JMY330 + pTEF-YFP-LEU2ex (Ura+ Leu+) | B. Treton unpublished |
| JMY2900 | Po1d, Ura+ Leu+ | Dulermo et al. (2017) |
| JMY5207 | JMY1212 lys5::URA3ex, | This work |
| JMY6245 (FCY003) | JMY2101 + pEYK300-YFP-URA3ex (Ura+ Leu+) | This work |
| JMY6369 | JMY2101 + pEYK300aB-YFP-URA3ex (Ura+ Leu+) | This work |
| JMY6372 | JMY2101 + pEYK300Ab-YFP-URA3ex (Ura+ Leu+) | This work |
| JMY6375 | JMY2101 + pEYK450-YFP-URA3ex (Ura+ Leu+) | This work |
| JMY6380 | JMY2101, + pHU4-EYK300-YFP-URA3ex (Ura+ Leu+) | This work |
| JMY6681 | JMY2101 + pEYK300A3B-YFP-URA3ex (Ura+ Leu+) | This work |
| JMY6684 | JMY2101 + pEYK300A3b-YFP-URA3ex (Ura+ Leu+) | This work |
| JMY7121 | JMY1212 Δlys5 | This work |
| JMY7123 | JMY1212 Δlys5, eyk1::URA3ex | This work |
| JMY7126 | JMY1212 Δlys5, Δeyk1 | This work |
| JMY7240 | JMY7126 + pEYK3AB-CalB-URA3ex + pEYK3AB-CalB-LYS5ex, (multicopie integration of CalB) | This work |

*JME for the *E. coli* strain, JMP for the plasmid.

Growth in Microplate and Fluorescence Analysis

*Y. lipolytica* precultures were grown overnight in YNBD, before being centrifuged, washed with an equal volume of YNB medium without carbon source and resuspended in 1 mL of the same medium. 96-well microplates containing 200 μL of the appropriated medium (final volume) were inoculated with washed cells at an $OD_{600\,nm}$ of 0.1. Growth was performed in a microtiter plate reader Synergy Mx (Biotek, Colmar, France), following the manufacturer's instructions at 28° C. and 110 rpm. $OD_{600\,nm}$ and fluorescence were measured every 20 min for 72 h. YFP fluorescence was analyzed with the wavelength settings ex: 505 nm/em: 530 nm. Fluorescence was expressed as specific fluorescence unit (SFU, normalized to biomass value) or mean specific fluorescence value (mSFU, mean value of SFU for the different sampling times). In all case, the SFU value of the wild-type strain JMY2900 (i.e. cell intrinsic fluorescence) was deduced from that of the YFP reporter strain in the same experimental conditions (sampling time and medium). Cultures were performed in replicates.

Growth and RedStarII Florescence Analysis

YNB medium supplemented with glucose (10 g/L) or erythritol (10 g/L) was used for growth and florescence analysis. Growth of Δeyk1 strains were performed in YNB Lysine medium with 0.25% glucose as carbon source and 0.25% erythritol as inducer as described previously (Trassaert et al. 2017). Each *Y. lipolytica* clone from the plate was grown in YNBD for 24 hours. Cells were then transferred to fresh medium (final volume 200 μL) in 96-well microplates. Growth was performed in a microtiter plate reader Synergy Mix (Biotek, Colmar, France) following the manufacturer's instructions at 28° C. and 110 rpm. OD600 nm and red fluorescence were measured every two hours for 60 hrs. Red fluorescence was analyzed with the wavelength settings ex: 558 nm/em: 586 nm. Fluorescence was expressed as mean specific fluorescence value per hour (SFU/h, mean value of SFU per hours). RedStarII fluorescence was expressed as specific fluorescence unit per hour. For RedStarII measurement, no intrinsic fluorescence was detected. Cultures were performed at least in duplicates.

Growth in Chemostat and Monitoring of Promoter Induction by Flow Cytometry

*Y. lipolytica* precultures were performed in YNBD for 12 h and washed cells were used for bioreactor inoculation at an $OD_{600\ nm}$ of 0.5. Chemostat were performed in 200 ml (150 ml working volume) DASGIP® DASbox Mini Bioreactors SR0250ODLS (Eppendorf, Hamburg, Germany). They were first run for 7 h in batch mode before being shifted in continuous mode with dilution rates as stipulated in the text. Feeding of fresh medium was ensured by a Watson Marlow 323S peristaltic pump (Watson Marlow, Falmouth Cornwall, UK), and removal of spent medium was ensured by a Watson Marlow 120 U/DM3 peristaltic pump (Watson Marlow, Falmouth Cornwall, UK). Culture parameters were set as follows: temperature, 30° C.; agitation rate, 800 rpm; aeration rate at 1 vvm. Carbon source pulses (CSP) in the reactors were at fixed volume (4.2 ml), regardless of the pulse concentration. After each CSP, biomass, YFP fluorescence and carbon source concentrations were monitored for 8 hours with a sampling frequency of one hour. CSP were performed at steady state. Chemostat cultures were performed in duplicate.

YFP fluorescence was monitored using a BD Accuri™ C6 Flow Cytometer (BD Biosciences, NJ, USA). Flow rate was fixed to 14 µl/min, and samples were diluted with phosphate saline buffer (PBS) to reach a cell density ranging between 500 and 2500 cells/µl. For each sample, 40,000 cells were analyzed using the FL1-A channel to identify fluorescence associated with the YFP (excitation was performed with a 20-mW, 488-nm solid-state blue laser; the emission wavelength was 533/30 nm). Additionally, data from the forward scatter channel (FSC-A) were collected to get information on the size dispersion among the cell population. The flow cytometry dotplots (FL1-A/FSC-A) were analyzed using CFlowPlus software (Accuri, BD Bioscience). For further processing, the raw data were exported as .fcs files and loaded in MatLab using the fca_readfsc function (downloaded from the MatLab File Exchange file server; http://www.mathworks.com). Background noise (cell intrinsic fluorescence) was fixed at 4,000 fluorescence units. This value encompasses the fluorescence level of at least 99.3% of the wild-type cells (strain JMY2900) grown in YNBG (glycerol), YNBOL (erythritol) and of JMY6245 (pEYK300-YFP) grown in YNBG (glycerol). Relative fluorescence (RFU) was defined as the sample median fluorescence value minus the intrinsic fluorescence value. Proportion of induced cells refers to the number of cells showing a fluorescence signal higher than 4,000 fluorescence units, relative to the total number of analyzed cells in the sample (i.e. 40,000). Gate Q1-UR of FSC-A/FL1-A cytograms encompasses induced cells.

Sequence Analysis

Genome sequences of *Yarrowia* species were assembled and annotated by Cécile Neuvéglise, Hugo Devillers and coworkers (to be published). Homologues of EYD1 and EYK1 genes in *Yarrowia* species were identified by Blast on the private site of GRYC (Genome Resources for Yeast Chromosomes; http://gryc.inra.fr) using EYD1 and EYK1 genes as template as described previously (Carly et al. 2017). Promoter regions were retrieved using the download functionality developed by H. Devillers. Multiple alignment of nucleotide sequence of EYK1 and EYD1 genes promoters among the *Yarrowia* clade: *Y. lipolytica* (YALI), *Yarrowia phangngensis* (YAPH), *Yarrowia yakushimensis* (YAYA), *Yarrowia alimentaria* (YAAL), and *Yarrowia galli* (YAGA) were then performed using the program Clustal Omega (Sievers, et al. 2011) available at http://www.ebi.ac.uk/Tools/msa/clustalo/. From those alignments, the motifs conserved through evolution and thus, more likely to carry a regulatory function, were identified. The conserved motifs were named Box A and Box B. To test their function as Upstream Activating Sequence or Upstream Activation Sequence (UAS), Region containing these conserved motifs+5 to 17 bases encompassing the conserved motifs were selected.

Plasmid and Yeast Strain Construction

Plasmid Construction

Restriction enzymes, DNA polymerases, and ligases were used in accordance with the manufacturer's recommendations. Restriction enzymes were obtained from OZYME (Saint-Quentin-en-Yvelines, France) except I-SceI that was obtained from New Englands Biolab. PCR amplifications were performed using an Eppendorf 2720 thermal cycler with PyroBest DNA polymerase (Takara) for cloning purpose and with GoTaq DNA polymerase (Promega) for deletion/overexpression verification. PCR fragments were purified using a QIAgen Purification Kit (Qiagen, Hilden, Germany), and DNA fragments were recovered from agarose gels using a QIAquick Gel Extraction Kit (Qiagen, Hilden, Germany). DNA sequencing was performed by GATC Biotech and primers were synthetized by Eurogentec (Seraing, Belgium). The Clone Manager software package (Sci-Ed Software) was used for gene sequence analysis and primer design. Disruption and expression cassettes were transformed with the lithium acetate method (Le Dall et al., 1994). Transformants were selected on YNBcasa, YNBura, or YNB depending on their genotype (Barth and Gaillardin, 1996). The genomic DNA from yeast transformants was prepared as described by Querol et al. (1992). The plasmids used in this study are summarized in Table 1 and primers are listed in Table 2. Primers MT-URA3-for, MT-YFP-rev, pTEF-start, 61stop were used to verify successful insertion of the expression cassette and the promoter sequences. For each transformation, at least three independent transformants carrying the correct integration were analysed. The representative clones were used for this study. The vectors carrying the yellow fluorescent protein (YFP) under the control of the pTEF and php4d have been previously described (Table 1). The pEYK1 promoters and its derivatives (mutated and hybrid promoters) were introduced by exchange of the ClaI-BamH1 region or the ClaI-SpeI region of YFP encoding plasmid as described below. *Y. lipolytica* strains were transformed by the lithium acetate method as described previously (Le Dall et al., 1994). Expression vectors (400 ng) were digested with NotI and subjected to electrophoresis. The bands corresponding to the expression cassettes were extracted from the gel and used for transformation. Cre-mediated marker rescue and curing of the replicative cre expression plasmid were performed as described previously (Fickers et al., 2003).

Plasmid Construction by Golden Gate Assembly

Most amplicons of promoters were cloned in the donor vectors (pCR Blunt II TOPO vectors; Thermo Fisher Scientific, Villebon sur Yvette, France), verified by BsaI digestions and sequencing. Some of the promoters were synthesized and cloned in the donor vector (pUC57) by GeneScript Biotech (New Jersey, US) (See Table 1). All the primers used to amplify the promoter were designed to have the upstream overhang "ACGG" and the downstream overhang "AATG" (See Table 3) to be applied to Golden Gate assembly. Other building blocks of Golden Gate assembly (destination vector, RedStarII, and Lip2 terminator) were prepared by purification of plasmids from our own GGE collection (Golden Gate E. coli collection). The destination vector GGE114, pSB1A3-ZetaUP-URA3-RFP-ZetaDOWN (Table 1) contains the following part: zeta UP, URA3, RFP (Red fluorescent protein giving red E. coli colony), and zeta DOWN. Promoter name, primer pairs, and template used for PCR are described in Table 4. The Golden Gate Assembly Strategy (GGAS) is presented in FIG. 17). The Golden Gate reaction conditions were performed following the previously published protocol (Celińska et al. 2017). The reaction mixture contained pre-calculated equimolar amount of each Golden Gate bio-bricks and the destination vector (50 pmoles of ends), 1 µl of T4 DNA ligase buffer (NEB), 5 U of BsaI, 200 U of T4 and ddH2O up to 10 µl. The following thermal profile was applied: [37° C. for 5 min, 16° C. for 5 min]*60 cycles, 55° C. for 5 min, 80° C. for 5 min, 15° C. ∞. Subsequently, the reaction mixture was used for E. coli DH5α transformation. White colonies were screened for identification of complete assemblies, afterwards PCR and restriction enzyme digestion of plasmids were conducted for verification. All bio-bricks were verified by sequencing.

TABLE 2

List of primers used

| SEQ ID NO: | Gene/name | Primers | Sequences * | |
|---|---|---|---|---|
| 14 | EYK1 | EYK-P-L | GTTGTGTGATGAGACCTTGGTGC | Deletion of EYK1 verification of EYK1 deletion |
| 15 | EYK1 | EYK-P-R-SfiI | AAAGGCCATTTAGGCCGCAGCTCCTCCGACAATCTTG | |
| 16 | EYK1 | EYK-T-L-SfiI | TAAGGCCTTGATGGCCACAAGTAGAGGGAGGAGAAGC | |
| 17 | EYK1 | EYK-T-R | GTTTAGGTGCCTGAAGACGGTG | |
| 18 | EYK1 | EYK-V1 | CGTACCCGAGATTGTACTGTTGTC | Verification of EYK1 deletion |
| 19 | EYK1 | EYK-V2 | CATAACCGCCTACCCTTGTAGC | |
| 20 | EYK1 | EYK1-AF | TTCTTGGGCCCGGCCTAAAT<u>GGCCCTGTTATCCCTAGATC</u>GATATAGAG | Catabolic marker EYK1. Sites SfiI; ApaI and |
| 21 | EYK1 | EYK1-KR | AATAAGGTACCGGCCATCAA<u>GGCCATTCGATTTGTCTTAG</u>AGGAACGC | SfiI*; KpnI |
| 22 | EYD1 | EYD-P-Fo | AAGCGTCCGAGACTGTCGGA | Deletion of EYD1 and verification of EYD1 deletion |
| 23 | EYD1 | EYD-P-sfi-Rev | AAAGGCCATTTAGGCCACTGACGTCTGTCTTGACGC | |
| 24 | EYD1 | EYD-T-Sfi-Fo | TATGGCCTTGATGGCCCAGCATTGAGTCCAACGAGC | |
| 25 | EYD1 | EYD-T-Rev | AGATCGAAGTTGGAATGAGA | |
| 26 | EYD1 | EYD-V | CGAGTTTCTAAGATGTACAT | |
| 27 | EYD1 | URA3-P-R1 | GTTGCCAATATCTGCGAACTTTCTG | |
| 28 | | LPR-F | ATAGGCCTAAATGGCCTGCATCGATCTAGGGATAACAGG | Markers amplification with SfiI and SfiI* |
| 29 | | LPR-R | ATAGGCCATCAAGGCCGCTAGATAGAGTCGAGAATTACCCTG | |
| 30 | LIP2 | LIP2-PF | CGGTCGGAATAATTACTGTGGACC | LIP2 deletion: amplification of promoter and terminator regions, SfiI and SfiI* and verification of LIP2 disruption |
| 31 | LIP2 | LIP2-PR | AAAGGCCATTTAGGCCACTTGGGTATCAATTGAGGGCTTTC | |
| 32 | LI P2 | LIP2-TF | TATGGCCTTGATGGCCTGTCTCGGAGGAGCTGCAGCCC | |
| 33 | LI P2 | LIP2-TR | TTGCTTAACACCAGTATCAGAACACAGAC | |
| 34 | LIP2 | LIP2-V | ACGGAAGCGAAGTACCTGTCAC | |
| 35 | ACT1 | ACT-F | GGCCAGCCATATCGAGTCGCA | for RT-qPCR of ACT1 gene |
| 36 | ACT1 | ACT-R | TCCAGGCCGTCCTCTCCC | |

TABLE 2-continued

List of primers used

| SEQ ID NO: | Gene/ name | Primers | Sequences * | |
|---|---|---|---|---|
| 37 | EYK1 | EYKq-F | CTTCTGCTGGACCCTCTGTC | for RT-qPCR of EYK1 gene |
| 38 | EYK1 | EYKq-R | ACTGCACGTAGGGGATCAAC | |
| 39 | EYD1 | EYD qper Fo | CATGACCTTTCGGAACCAGT | for RT-qPCR of EYD1 gene |
| 40 | EYD1 | EYD qper Rev | AACGCCTCTCTGGTCTTCAA | |
| 41 | P300 | pEYK300 F | GACATCGATGCATCTACTTT TCTCTATACTGT | Promoter ampli, ClaI |
| 42 | P300 | pEYK R | GACGGATCCAGTAGATGTGT AAGTGTGTAGAAG | Promoter ampli, BamHI |
| 43 | P450 | MT-TATAampli-F | ACGATCGATTTTGTGCAAGT GTGTGTGTGTG | Promoter ampli, ClaI |
| 44 | P450 | MT-TATAampli-R | ACGACTAGTCAGGTCATCGG ATTATGCAAGG | Promoter ampli, SpeI |
| 45 | | ST043pEYK-mut1 | CGATGCATCTACTTTTCTCTA TACTGTACGTTTCAATCTGG GGAAGCGGAATCCCAAAAG GGAAAGCCGCCGCATTAAG CTCCACAGCC | WT native Box A |
| 46 | | ST044pEYK-mut1BIS | CGATGCATCTACTTTTCTCTA TACTGTACGTTTCAATCTGG GGAAGCGGAATCCCAAAAG GACGCGTCGCCGCATTAAG CTCCACAGCC | Mutated Box A |
| 47 | | ST045pEYK-mut2 | TTGCATAATCCGATGACCTG A | WT native Box B |
| 48 | | ST046pEYK-mut2BIS | TTGTACGCGTAGATGACCTG A | Mutated Box B |
| 49 | | ST047pEYK-mutA | GGCGTAATTCGAGGTGTCG GAACGTATTAGGCTACTGGA CTGATC | WT native Box A complementary strand |
| 50 | | ST048p EYK-mutABIS | GGCGTAATTCGAGGTGTCG GAACATGCGCATCTACTGGA CTGATC | Mutated Box A complementary strand |
| 51 | | ST049pEYK-mutB | TACGTAGATGAAAAGAGATA TGACATGCAAAGTTAGACCC CTTCGCCTTAGGGTTTTCC TTTCGCG | WT native Box B complementary strand |
| 52 | | ST050pEYK-mutBbis | TACGTAGATGAAAAGAGATA TGACATGCAAAGTTAGACCC CTTCGCCTTAGGGTTTTCC TGCGCACG | Mutated Box B cornplementary strand |
| 53 | | MT-URA3-for | GCGTAGGTGAAGTCGTCAAT | For promoter sequence verification (forward) |
| 54 | | MT-YFP-rev | CAGATGAACTTCAGGGTCAG C | For promoter sequence verification (reverse) |
| 55 | | pTEF-start | GGGTATAAAAGACCACCGTC C | For gene verification (forward) |

TABLE 2 -continued

List of primers used

| SEQ ID NO: | Gene/name | Primers | Sequences * | |
|---|---|---|---|---|
| 56 | | 61stop | GTAGATAGTTGAGGTAGAAG TTG | For gene verification (reverse) |
| 57 | | SfiI | GGCCTAAATGGCC | |
| 58 | | SfiI* | GGCCATCAAGGCC | |

* Modified sequences are in bold, restriction sites introduced are underlined.

Construction of PEYK300

The promoter region of EYK1 gene (pEYK300) was amplified from genomic DNA of *Y. lipolytica* strain W29 with primer pair pEYK300 F/pEYK R, designed to introduce a ClaI and BamHI restriction sites, respectively, in the amplified fragment. The resulting amplicon was purified and cloned into pJET1.2, to yield plasmid FCP007. The pEYK300 fragment was then released from FCP007 and cloned at the corresponding site of JMP1427, yielding the plasmid JMP3934.

Construction of PEYK450, PEYK300Ab and PEYK300aB Promoters

Plasmid containing pEYK450 was obtained by PCR amplification of the intergenic region between genes YALI0F01628g and YALI0F01606g with primer pair MT-TATAampli-F/MT-TATAampli-R. This resulted in a 252 bp fragment carrying T, A and B boxes within a ClaI-SpeI fragment at the 5' and 3' ends, respectively. This fragment was ligated into FCP013 digested by ClaI-SpeI, to yield the plasmid JMP3994 (pEYK450). Plasmids containing pEYK300Ab and pEYK300aB were obtained by exchange of the ClaI-SpeI fragment of JMP3934 (pEYK300) by two ClaI-SpeI DNA fragments carrying the A (aB) or B (Ab) mutated regions, respectively. They were obtained by annealing oligonucleotides ST044/ST045/ST050/ST047 (fragment aB) and ST043/ST046/ST049/ST048 (fragment Ab) (Table 2). The oligonucleotides ST044 and ST046 contains a MluI site for the verification of the insertion of the mutation. The resulting plasmids were designated as JMP3988 (pEYK300aB) and JMP3991 (pEYK300Ab), respectively.

Construction of Hybrid PHU4EYK300 Promoter

The fragment carrying four tandem repeats of the UAS1$_{XPR2}$ (HU4 deriving from pHp4d) was obtained by ClaI-BstBI digestion from the JMP2027 vector (Dulermo et al., 2017). After gel purification, it was then ligated at the ClaI site of JMP3934 (previously digested by ClaI and dephosphorylated). Correct orientation of the HU4 region was verified by ClaI-BamHI restriction and DNA sequencing. The resulting plasmid was named JMP3998 (pHU4EYK300).

Construction of Hybrid EYK Promoter

Synthetic promoters carrying three repeated of UAS1-eyk1 upstream of the wild-type Box B (A3B, JMP4123) and the mutated Box B (A3b, JMP4124) were synthesised by GenScript (www.genscript.com/) with ClaI and SpeI sites at the 5' and 3' ends, respectively. The ClaI-SpeI fragment from JMP4123 and JMP4124 were ligated into JMP918 digested by ClaI-SpeI, yielding the plasmid JMP4137 (pEYK300A3B) and JMP4139 (pEYK300A3b), respectively.

Deletion of the EYK1 Gene

The EYK1 disruption cassette was generated by PCR amplification. First, the upstream (Up) and downstream (Dn) regions of the EYK1 gene were amplified using *Y. lipolytica* W29 genomic DNA as the template with the EYK-P-L/EYK-P-R-SfiI and EYK-T-L-SfiI/EYK-T-R as primer pairs. URA3ex marker was amplified from JMP113 with the primer pair LPR-L-SfiI/LPR-R-SfiI (Table 2). Amplicons were digested with SfiI before being purified and ligated, using T4 DNA ligase. The ligation product was amplified by PCR using the primer pair EYK-P-L/EYK-T-R. The eyk1::URA3ex disruption cassette was finally used to transform *Y. lipolytica* strain Po1d. The resulting strain was designated RIY147 (eyk1::URA3ex, Leu⁻). The auxotrophic derivative RIY176 was isolated after transformation with the replicative plasmid pRRQ2 according to Fickers et al. (2003) for marker rescue (Table 1). The primers EYK-V1 and EYK-V2 (Table 2) were used for gene disruption verification.

Deletion of the EYD1 Gene

The EYD1 disruption cassette was generated by PCR amplification. First, the upstream (Up) and downstream (Dn) regions of the EYD1 gene were amplified using *Y. lipolytica* W29 genomic DNA as the template with the EYD-P-Fo/EYD-P-sfi-Rev and EYD-T-Sfi-Fo/EYD-T-Rev as primer pairs. URA3ex marker was amplified from JMP113 with the primer pair LPR-F/LPR-R (Table 2). Amplicons were digested with SfiI before being purified and ligated, using T4 DNA ligase. The ligation product was amplified by PCR using the primer pair P1-EYD/T2-EYD. The eyd1::URA3ex disruption cassette was finally used to transform *Y. lipolytica* strain Po1d. The resulting strain was designated RIY212 (eyd1::URA3ex). The auxotrophic derivative RIY225 was isolated. The primers EYD-V and URA3-P-R1 (Table 2) were used for gene disruption verification.

Construction of Plasmid JMP3739

*Y. lipolytica* Lip2prepro-CalB protein was codon optimized using in house codon optimization software (Biocatalysts LTD), synthesized by Geneart (15ACCYPP_1762989_LIP2-CalB-YI-Opt) and cloned into JMP1046 giving rise to JMP3739 (15ACCYRP_1762990_pJME1046-CalB). The Lip2prepro-CalB sequence is provided as set forth in SEQ ID NO: 59:

<u>ATGAAGCTGCTGTCTCTGACCGGTGTGGCTGGTGTTCTGGCCACCTGTGT</u>

<u>CGCTGCCACCCCTCTGGTGAAGCGACTGCCTTCTGGATCTGACCCTGCCT</u>

<u>TCTCTCAGCCCAAGTCTGTTCTGGACGCTGGTCTGACCTGTCAGGGAGCT</u>

<u>TCTCCTTCTTCTGTGTCTAAGCCCATTCTCCTGGTGCCTGGAACCGGAAC</u>

CACCGGTCCTCAGTCTTTCGACTCGAACTGGATTCCTCTGTCTACCCAGC

```
-continued
TGGGATACACCCCCTGTTGGATTTCTCCTCCTCCTTTCATGCTGAACGAC

ACCCAGGTGAACACCGAGTACATGGTGAACGCCATTACCGCTCTGTACGC

TGGCTCTGGAAACAACAAGCTGCCCGTTCTGACCTGGTCTCAGGGAGGTC

TGGTGGCTCAGTGGGGTCTGACCTTCTTCCCTTCTATTCGATCTAAGGTG

GACCGACTGATGGCCTTCGCTCCCGACTACAAGGGAACCGTTCTGGCTGG

TCCTCTGGACGCTCTGGCTGTCTCTGCTCCTTCTGTGTGGCAGCAGACCA

CCGGCTCTGCTCTGACCACCGCTCTGCGAAACGCTGGAGGTCTGACCCAG

ATTGTCCCCACCACCAACCTGTACTCTGCCACCGACGAGATTGTCCAGCC

TCAGGTGTCTAACTCTCCTCTGGACTCTTCGTACCTGTTCAACGGAAAGA

ACATTCAGGCTCAGGCTGTCTGTGGACCTCTGTTCGACATTGACCACGCT

GGCTCTCTGACCTCTCAGTTCTCCTACGTGGTTGGACGATCTGCTCTGCG

ATCTACCACCGGTCAGGCTCGATCTGCTGACTACGGTATCACCGACTGTA

ACCCTCTGCCTGCCAACGACCTGACCCCTGAGCAGAAGGTGGCTGCTGCT

GCTCTGCTGGCTCCCGAGGCTGCTGCCATTGTCGCTGGTCCCAAGCAGAA

CTGCGAGCCCGACCTGATGCCTTACGCTCGACCCTTCGCTGTTGGAAAGC
GAACCTGTTCTGGTATTGTCACCCCTTAA
(Lip2 prepro sequence is in bold and underlined).
```

Plasmid JMP1046 containing the pTEF promoter present the typical structure of the expression vector JMP62 (Nicaud et al., 2002) carrying an excisable marker (I-scel fragment flanked by LoxP/LoxR, a promoter as a ClaI-BamHI fragment, BamHI and AvrII sites for cloning a gene of interest and zeta region for random or zeta platform expression cassette integration, flanked by NotI site for the release of the expression cassette prior transformation.

Construction of JMP4266.

Promoter exchange was performed by digestion of JMP1046 plasmid by ClaI-BamHI for insertion of the inducible promoter pEYK3AB ClaI-BamHI fragment from JMP4123 resulting in plasmid JMP4266.

Construction of CalB Expression Vectors

First, the BamHI-AvrII fragment carrying preproLip2-CalBop was isolated from BamHI-AvrII digested JMP3739 and cloned at the corresponding site into JMP4266, giving rise to JMP4365. In a second step, the derivative plasmid JMP4384 was constructed by exchange of the IScel-URA3ex fragment with the corresponding I-SceI-LYS5ex fragment carrying the LYS5ex marker from JMP3265.

Construction of JMY7126.

The construction has been realized by successive gene deletion and marker rescue according to Fickers et al. (2003) as described in FIG. 15 using lys5::URA3ex (JME3265) and eyk1::URA3ex (JME4056) disruption cassettes. Marker rescue was obtained after transformation with the replicative plasmid carrying the hygromycin-B resistance hph marker (pUB4-cre-hph; JME547) and the catabolic marker EYK1 marker (Cre-ARS68-pTEF-EYK1; JME4265) described in Table 1. To cure cells of the cre expression plasmid, cells were grown on YPD. The loss of the replicative plasmids was checked by replica plating on YPD, and YPDhyg for pUB-cre-hph and on YNBglucose and YNBerythritol for pGEM6-easy-cre-EYK1. Correctness of marker excision was verified on YNBA glucose and YNBA erythritol supplemented with lysine.

Construction JMY7240

Strain JMY7126 was co-transformed with the two expression cassettes URA3ex-pEYK3AB-CalB (JMP4365) and LYS5ex-pEYK3AB-ClaB (JMP4384) (Table 1). Transformants were selected on YNBD agar plate.

Construction of JMY7126

Strain JMY7126, deriving from JMY1212, has been obtained after successive gene deletion (LYS5 and EYK1) and marker rescue (FIG. 15). The PUT plasmids (Promoter-URA3ex marker-Terminator) were constructed for gene disruption according to Fickers et al 2003 for LYS5 and according to Vandermies et al., 2017 for EYK1. The disruption cassettes were prepared by digesting PUT plasmids followed by transformation into Y. lipolytica strain. Transformants were selected on YNB Leucine, YNB Leucine Lysine medium depending on their genotype. The replicative plasmids (JME547, RIE132-JME4265) harboring Cre recombinase gene were used for excising URA3ex marker.

Construction of Strain for Promoter Studies

Strains for promoter studies are described in Table 1. Plasmids for promoter analysis, assembled by Golden Gate assembly, were digested by NotI to allow the release of the expression cassette prior Y. lipolytica JMY1212 and JMY7126 transformation. After transformation with 100 ng DNA via the lithium acetate method (Le Dall et al., 1994), transformants were selected utilizing YNB or YNB Lysine medium depending on their genotype. After florescence test of twelve transformants of each construct, representative clone was selected (Table 1, Example 12).

Analytical Methods

Erythritol, erythrulose, glucose and glycerol concentrations in the culture supernatant were measured by HPLC (Agilent Technologies 1200 series) using a Aminex HPX-87H ion exclusion column, (Biorad 300×7.8 mm). Elution was performed using 15 mM trifluoroacetic acid as the mobile phase at a flow rate of 0.5 mL/min and a temperature of 65° C. Erythritol, glucose and glycerol were detected using a refractive index detector (RID, Agilent Technologies), while erythrulose was measured at 210 nm with a UV detector (Agilent Technologies).

Protein Analysis.

Protein concentration was determined as described by Bradford (Bradford, M. M. 1976). The standard curve was obtained by serial dilutions of Pierce™ Bovine Serum Albumin Standard Ampules (Thermo Fisher Scientific, Waltham, MA, USA). Proteins were subjected to sodium dodecyl sulfate (SDS)-polyacrylamide gel electrophoresis (PAGE) on a Novex™ 12% Tris-Glycine Mini Gel (Thermo Fisher Scientific) as described by Laemmli (Laemmli, U. K. 1970). Four µl of pre-stained Protein Marker IV (AppliChem GmbH, Darmstadt, Germany) were used as molecular mass standards. Cell culture protein amounts equivalent to 5 µl of cell supernatant were loaded per lane.

Lipase Activity.

Figure 1:
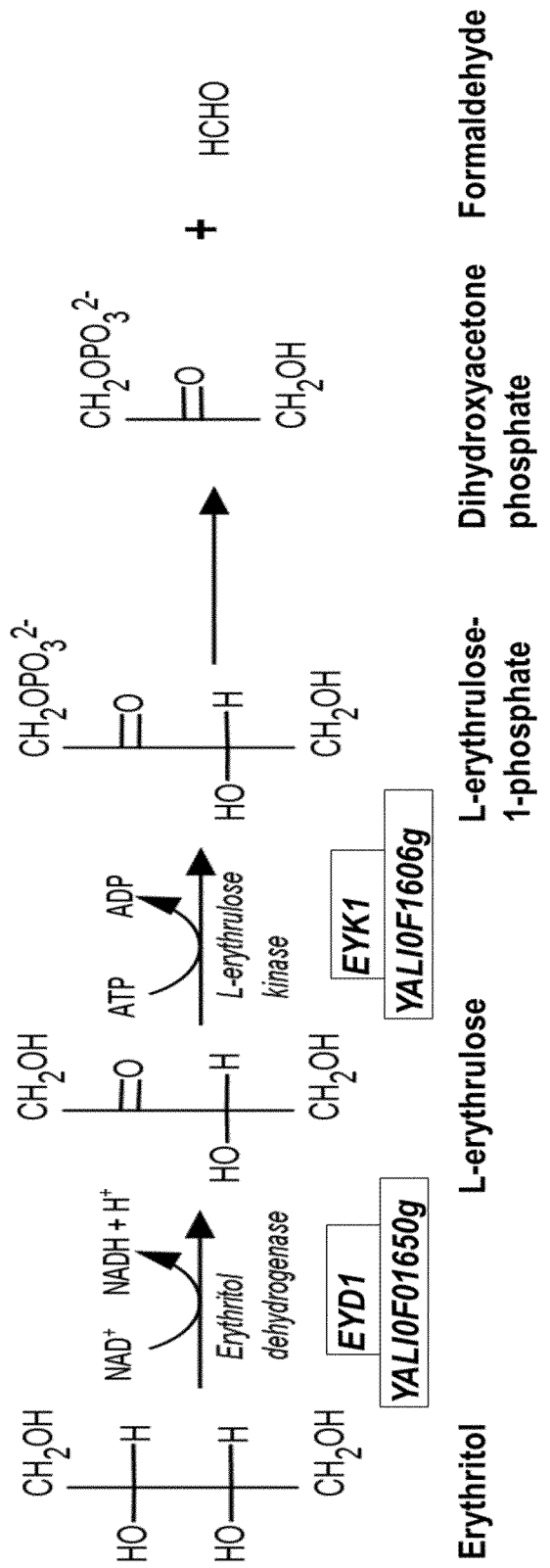
FIG. 1 is a schematic representation of erythritol catabolism in *Y. lipolytica*. Erythritol is converted into L-erythrulose by an erythritol dehydrogenase encode by EYD1 (YALI0F01650g), then L-erythrulose is phosphorylated by the L-erythrulose-1-phosphatase encoded by EYK1 (YALI0F01606g) in L-erythrulose-1-phosphate.

Lipase activity on solid media was monitored on tributyrin plates (YNBDETo medium) after 120 h of incubation as previously described (Pignede et al., 2000). Lipase activity in culture supernatants was determined by monitoring the hydrolysis of para-nitrophenyl butyrate (p-NPB), according to Fickers et al. 2003. Briefly, p-NPB dissolved in acetonitrile (20% v/v) was added dropwise into vigorously stirred 100 mM phosphate buffer, pH 7.2, containing 100 mM NaCl to a final concentration of 1 mM. The resulting solution was sonicated for 2 min on ice. The reaction was initiated by addition of 20 µl of culture supernatant (pure or diluted) to 1 mL of p-NPB solution. The release of para-nitrophenol (εPNP=0.0148 μM−1 cm−1) was monitored for three min at 405 nm (A405). Supernatant samples were diluted to obtain initial velocities below A405 of 0.3 U/min. All lipase activity assays were performed at least in duplicate from two independent cultures. One unit of lipase activity was defined as the amount of enzyme releasing 1 μmol p-NPB per minute at 25° C. and pH 7.2 (U/ml). Specific lipase activity was defined as lipase activity per gram of CDW (U/gCDW). Lipase volumetric production rate was defined as lipase activity per hour of culture (U/mL·h). Lipase specific production rate was defined as lipase activity per gram of CDW per hour of culture (U/gCDW·h).

that EYK1 encode an erythrulose kinase and that erythritol catabolism in *Y. lipolytica* follows the pathway depicted in FIG. 1.

Example 2. Expression Levels of EYK1 and EYD1 in Erythritol or Glucose Medium

In order to evaluate the expression level of genes EYK1 and EYD1 in erythritol or glucose medium, qPCR experiments were performed in the W29 wild-type strain. Shake-flask cultures were grown for 12 hours in YNB medium supplemented with either glucose or erythritol. Cells were then collected at an OD600 of 1.0 and stored at −80° C.

TABLE 3

List of primers used for promoter analysis using RedStarII reporter gene

| SEQ ID NO: | Primers | Sequences* | Use |
|---|---|---|---|
| 60 | P1 TEF FW | GGTCTCT*ACGG*GGGTTGGCGGCG | Amplification for building block construction |
| 61 | P1 TEF RV | GGTCTCT*CATT*CTTCGGGTGTGAGTTAC | |
| 62 | P1 EYK FW | GGTCTCT*ACGG*CCCATCGATGGAAACCTTAATAGGAGACTACTTCC | |
| 63 | P1 EYK RV | GGTCTCT*CATT*GGATCCAGTAGATGTGTAAGTG | |
| 64 | P1 EYD FW | GGGGGGTCTCT*ACGG*CCCATCGATGGAAACCTTAATAGGAGACTACTTCC | |
| 65 | P1 EYD RV | CCCGGTCTCT*CATT*TGTGTATGTGTGTGTGTGTGTG | |
| 66 | EYD UAS1 MluI Fw | CCTTAATAGGAGACTACTTCCGACGCGTAATTAGG | Addition of MluI site for EYD1 UAS mutation |
| 67 | EYD UAS1 MluI RV | CCTAATTACGCGTCGGAAGTAGTCTCCTATTAAGG | |
| 68 | EYD UAS2 MluI Fw | GAACTCGATACGCGTGCCGTACTCTGGAAA | |
| 69 | EYD UAS2 MluI RV | TTTCCAGAGTACGGCACGCGTATCGAGTTC | |
| 70 | ZetaUp-internal-FW | TATCTTCTGACGCATTGACCAC | Verification of Golden Gate assembly |
| 71 | URA3-internal-FW | CATCCAGAGAAGCACACAGG | |
| 72 | URA3-internal-RV | CAACTAACTCGTAACTATTACC | |
| 73 | Redstar-internal-FW | AAGACGGTGGCGTTGTTACT | |
| 74 | RedStar-internal-RV | GACTTGCTTCTTGGCCTTGT | |
| 75 | Tlip2-internal-FW | TGCGTTCCTCTAAGACAAATC | |
| 76 | Tlip2-internal-RV | GATTTGTCTTAGAGGAACGCATA | |
| 77 | ZetaDown-internal-RV | GGTAACGCCGATTCTCTCTG | |

*Bold-underlined correspond to the BsaI site with the overhang in italic.

Example 1. EYK1 Promoter is Induced by Erythritol and Erythrulose

Figure 2:
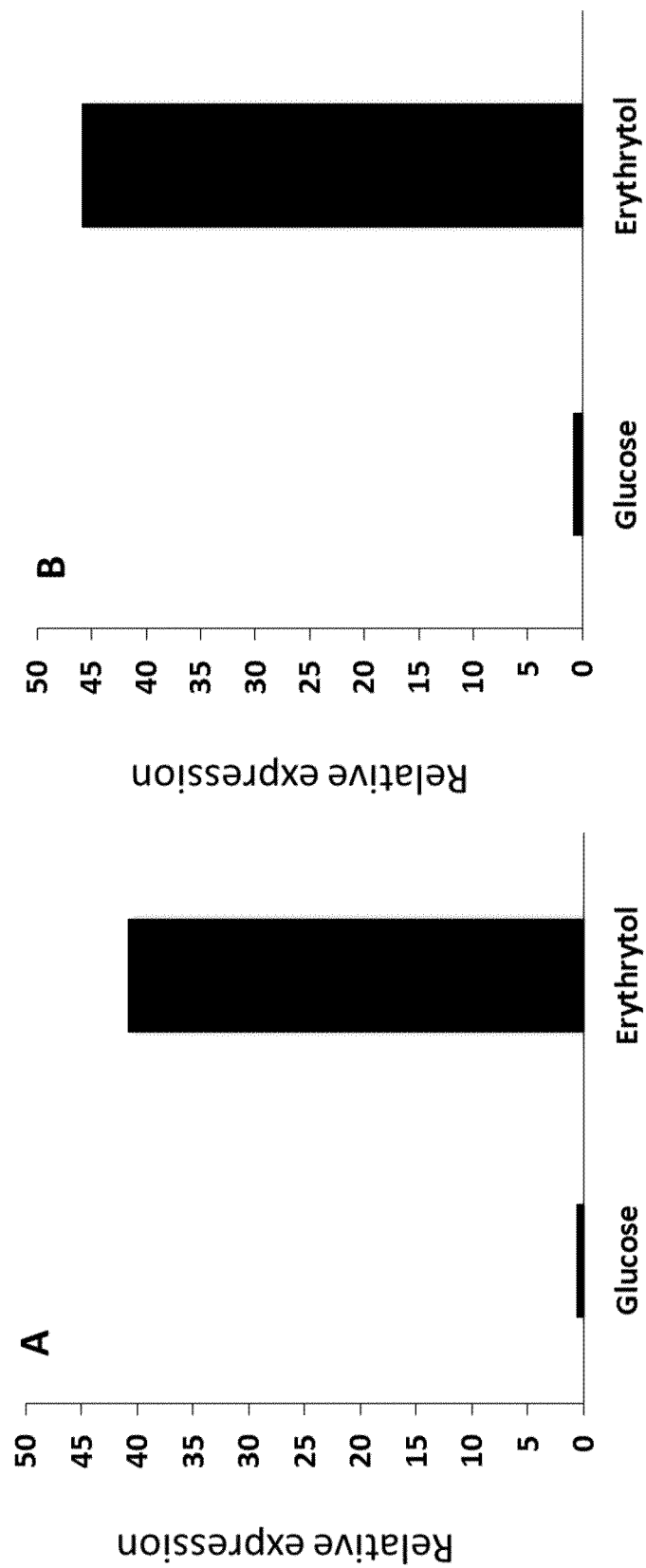
FIG. 2 is showing relative expression levels of EYK1 (A) and EYD1 (B) in erythritol or glucose medium. Gene expression levels were standardized using the expression level of actin as the reference (ACT method).

To date, two different pathways have been reported for erythritol catabolism. In a first one, erythritol is phosphorylated into erythritol-phosphate and then oxidized in erythrulose-phosphate (Barbier et al 2014). In a second one, erythritol is first converted into erythrulose before being phosphorylated into erythrulose-phosphate (Paradowska and Nikta, 2009). We have recently identified and characterized EYK1 gene (YALI0F1606g) in *Y. lipolytica*. Disruption of the latter abolished yeast growth on erythritol medium, showing that EYK1 gene is involved in erythritol catabolism. In addition, a Δeyk1 mutant was found to accumulate L-erythrulose. From this, it has been concluded RNA extraction and cDNA synthesis were performed as previously described (Sassi et al., 2016). Amplification was performed using primer couples ACT-F/ACT-R, EYKq-F/EYKq-R and EYDq-F/EYDq-R for actin, EYK1 and EYD1 respectively (Table 2). Gene expression levels were standardized using the expression level of actin as the reference (ΔCT method). The fold difference in EYK1 or EYD1 expression between YNB+glucose and YNB+erythritol medium was calculated as $2^{-\Delta\Delta CT}$ (Livak and Schmittgen, 2001). Samples were analyzed in duplicate. Results are on FIG. 2 and showed a 41-fold increase of EYK1 expression level and a 46-fold increase of EYD1 expression level when cells were grown on erythritol, indicating that this gene is induced by the presence of erythritol. (A) EYK1 value 0.8 (glucose) and 40.9 (erythritol); B) EYD1 value 0.8 (glucose) and 45.9 (erythritol)).

Example 3. Identification and Study of EYK1 and EYD1 Regulatory Elements

Gene EYK1

In order to identify the regulatory element (i.e. UAS) the EYK1 promoter region, we analysed the nucleotide sequence using the intergenic region between YALI0F01628g and YALI0F01606g (FIG. 3). Blast analysis of the EYK1 promoter did not evidenced any conserved motif within *Yarrowia lipolytica* genome (data not shown). Therefore, we compared the promoter region of the EYK1 gene to those present in species of the *Yarrowia* clade other than *Yarrowia lipolytica* (SEQ ID NO: 78) (namely, *Yarrowia phangngensis* (SEQ ID NO: 79), *Yarrowia yakushimensis* (SEQ ID NO: 80), *Yarrowia alimentaria* (SEQ ID NO: 81) and *Yarrowia galli* (SEQ ID NO: 82) that have been recently sequenced and annotated in our laboratory. Alignment of the EYK1 promoter sequences (FIG. 3) highlighted three putative conserved elements; a putative TATA box (Box TATA) and a conserved motif A (Box A) and a conserved motif B (Box B).

Gene EYD1

In order to identify the regulatory element (i.e. UAS) within the EYD1 promoter region, we analysed the intergenic region between YALI0F01650g and YALI0F01672g. Since that this intergenic region was greater than 5500 bp (5591 bp), we analysed the upstream region using the 800 bp nucleic acid sequence upstream of YALI0F01650g. Blast analysis of the EYD1 promoter did not evidenced any conserved hit within *Yarrowia lipolytica* genome (data not shown). Therefore, we compared the promoter region of the EYD1 gene to those present in other species of the *Yarrowia* clade (namely, *Yarrowia phangngensis, Yarrowia yakushimensis, Yarrowia alimentaria* and *Yarrowia galli*) that have been recently sequenced and annotated in our laboratory. Boxed ATG correspond to the start codon of the YALI0F01650g. Sequence are from *Y. lipolytica* E150 (YALI; YALI0F01606g (SEQ ID NO: 83)), *Yarrowia galli* (YAGA, gene YAGA0A02014g (SEQ ID NO: 84)), *Yarrowia phangngensis* (YAPH-pEYD1, (SEQ ID NO: 85)), *Yarrowia yakushimensis* (YAYA-pEYD1 (SEQ ID NO: 86)) and *Yarrowia alimentaria* (YAAL-pEYD1 (SEQ ID NO: 87)). Alignment of the EYD1 promoter sequences highlighted conserved motifs observed only within the 300 bp upstream region (FIG. 4) three putative conserved elements; a putative TATA box (Box TATA; GATATAWA) and a conserved motif (Box A) and a conserved motif (Box B) and a variable number of CA repeats just before the ATG.

In order to assess the regulation of the EYK1 promoter, two fragments of 450 bp and 300 bp, (EYK450 and EYK300, respectively), corresponding to the intergenic region of genes YALI0F01606g and YALI0F01628g were used to construct a reporter gene system based on a yellow fluorescent reporter protein (YFP) and the YFP fluorescence was used to quantify the promoter induction level (FIG. 5).

Fragments EYK450 and EYK300 that span over 438 bp and 291 bp upstream of the EYK1 start codon (FIG. 5a) were cloned JMP1427 as described in material and methods to yield plasmid JMP3934 (pEYK300) and JMP3994 (pEYK450), respectively (FIG. 6). They were then used to transform *Y. lipolytica* strain JMY2101. Several independent transformants (3 to 6) were randomly selected for each construct and the corresponding YFP fluorescence measured during cell growth on erythritol medium (YNBE). Since no differences in YFP fluorescence level, and thus promoter induction, could be observed (data not shown), one transformant of each construct was used for further studies, namely strains JMY6245 (pEYK300-YPF) and JMY6375 (pEYK450-YFP), respectively (Table 1).

Cell growth and YFP fluorescence were quantified over time during culture of strain JMY6245 in YNB minimal media supplemented with glucose (YNBD), glycerol (YNBG), erythritol (YNBOL) and erythrulose (YNBOSE).

In medium containing erythritol (YNBOL) and erythrulose (YNBOSE), YFP fluorescence, and therefore pEYK300 induction levels were significantly higher than in the presence of glucose (YNBD) and glycerol (YNBG) (3157 and 4844 mSFU as compared to 344 and 357 mSFU, respectively) (FIG. 7a). This clearly highlights that erythrulose and erythritol positively regulate pEYK300 induction by contrast to glucose and glycerol. However, the low fluorescence levels observed in YNBD and YNBG medium, suggest that pEYK300 is slightly induced by glucose and glycerol. After 60 h of culture, the fluorescence level in medium supplemented with erythrulose was 1.5-fold higher than in the presence of erythritol (3536 SFU and 5904 SFU, respectively). This suggests that erythrulose could be a better inducer than erythritol. Experiments performed with strain JMY6375 (pEYK450-YFP) in the same experimental conditions yielded to similar results (data not shown). Therefore, the pEYK300 promoter seems to encompass the different regulatory elements requested for gene expression (UAS and URS).

In order to assess the strength of pEYK300 induction by erythritol and erythrulose, it was compared to that of the strong constitutive pTEF promoter. YFP fluorescence of strain JMY2876 (pTEF-YFP) was measured in the same experimental conditions and compared to that of strain JMY6245. As shown in Figure. 7b, pTEF expression was similar in the four media tested, with fluorescence values being 1192, 1369, 1485 and 1016 mSFU in YNBOL, YNBOSE, YNBDD and YNBG, respectively. Expression level for pEYK300 in YNBOL and YNBOSE were in average 2.6- and 3.5-fold higher than the expression level of pTEF, respectively.

The comparison of YFP fluorescence under pEYK450 and pEYK300 indicates that the TATA box may be involved in the expression of gene YALIPF01628g rather than gene YALI0F01606g. Thus, in order to determine the role of Box A and Box B in pEYK regulation, two mutated promoters, namely pEYK300aB and pEYL300Ab, were constructed as described in material and method by exchange of the ClaI-SpeI fragment. Mutation of the conserved Box A and Box B were performed by introducing a MulI site. The sequence [GGAAAGCCGCC] was replaced by [GGAACGCGTCC] and named a. The sequence [CTTGCATAATCCGATGAC] was replaced by [CTTGTACGCGTAGATGAC] and named b. This yielded to pEYK300aB and pEYK300Ab, respectively (FIG. 5b). The mutated pEYK300aB and pEYK300Ab were introduced into strain JMY2101 (Po1d Leu+) to give rise to representative strains JMY6369 and JMY6372, respectively (Table 1). For strain JMY6369 carrying the pEYK300aB mutant promoter, YFP fluorescence was remarkably reduced in the presence of erythritol (YNBOL) and erythrulose (YNBOSE) (683 and 1481 mSFU, respectively) (FIG. 8a). This observation suggested that the Box A is part of the upstream activating sequence (UAS1$_{EYK1}$) required for the promoter induction by both erythritol and erythrulose.

On the opposite, the mean relative YFP fluorescence measured for strain JMY6372 carrying the pEYK300Ab mutated promoter (FIG. 8b), was 2.4-fold higher in the presence of erythritol (YNBOL medium) than for the non-mutated pEYK300 promoter in the same conditions (8389 and 3536 SFU after 60 h, respectively). In contrast, YFP fluorescence was in the same range in the presence of erythrulose (YNBOSE medium) than that of the non-mutated promoter. Furthermore, pEYK300Ab was less repressed on glucose media as compared to pEYK300 (with a mean specific fluorescence of 718 versus 279 mSFU) suggesting that the Box B may be involved in glucose repression. This clearly demonstrate that Box A is involved in erythritol and erythrulose induction and that Box B may be involved in glucose repression since expression of the pEYK300Ab increased at the end of the culture in glucose media, which is not the case in glycerol media.

Example 4. Tandem Repeats of $UAS1_{EYK1}$ Increase Promoter Strength

Multicopy repeats of UAS elements upstream of a promoter have been shown to increase promoter strength (Madzak et al. 2000; Blazeck et al. 2011; Blazeck et al. 2013; three repeats of the 48 bp $UAS1_{EYK1}$ fragment (GGGAAGCGGAATCCCAAAAGGGAAAGCCGCCGCATTAAGCTCCACAG

C; SEQ ID NO: 13)

encompassing the Box A (in bold and underlined), upstream of the wild-type pEYK300 promoter (FIG. 5c). The resulting construct was introduced into strain JMY2101 to give rise to strains JMY6681.

Promoter strength was monitored in the presence of glucose (YNBD), glycerol (YNBG), erythritol (YNBOL) and erythrulose (YNBOSE) and compared to that of pEYK300 (strain JMY6245). As shown in FIG. 9a, YFP fluorescence measured for pEYK300A3B was 3.4-fold higher in average in the presence of erythritol as compared to pEYK300 (10538 mSFU and 3157 mSFU, respectively). In contrast, induction of pEYK300A3B was found similar in average in the presence of erythrulose as compared to pEYK300 (5034 mSFU and 4844 mSFU, respectively). By contrast to previous observation with pEYK300 (FIG. 7a) pEYK300A3B induction level was 2.1 fold higher in average in the presence of erythritol than for erythrulose (10538 mSFU and 5034 mSFU, respectively). Similar experiments performed with strain JMY6684 (pEYK300A3b), showed that the induction profile on YNBOL were not significantly different from that of JMY6681 (pEYK300A3B) except that induction was significantly less repressed by glucose and glycerol, confirming thus previous observations (data not shown).

Since the insertion of several copies of the 48 bp $UAS1_{EYK1}$ encompassing the Box A resulted in a stronger promoter induction level, it could be assumed that increasing the copy number of $UAS1_{EYK1}$ would allow to fine tune the strength of promoter induction. Indeed, several strong synthetic hybrid promoters have been created by fusing tandem repeats of upstream activation sequence (UAS) upstream to a core promoter region. The first one (hp4d) was based on four tandem repeats of the 108 bp $UAS1_{XPR2}$ of the XPR2 gene upstream on the minimal LEU2 core promoter (Madzak et al, 2000). Later Blazek and coworker's constructed hybrid promoter containing up to 32 copies of $UAS1_{XPR2}$ of the XPR2 gene upstream on the minimal LEU2 core promoter and 16 copies of $UAS1_{XPR2}$ of the XPR2 gene upstream of TEF core promoters of different length (Blazek et al, 2011). Promoter strength increase with copy number of the UAS, and the best one showed a 10-fold increase expression compared to the pTEF promoter. Similar expression levels were obtained by inserting three tandem copies of the 230 bp $UAS1_{TEF}$ upstream of the pTEF promoter (Blazek et al, 2013) and its expression did not vary significantly with carbon source (glucose, sucrose, glycerol and oleic acid). The only strong inducible promoter is the POX2 one (Juretzek et al. 2000). Oleic acid inducible hybrid synthetic promoters were obtained comprising eight copies of $UAS1_{xpr2}$ upstream of the 100 bp proximal core POX2 promoter. This UAS-core promoter chimera showed a 4.2-fold higher expression level in oleic acid media than in glucose in contrast to a 2-fold higher expression level for the 8 copies of $UAS1_{xpr2}$ upstream of the 136 bp proximal core TEF promoter (Hussain et al. 2016). Here we showed that an hybrid promoter containing two additional tandem copies of the short 48 bp $UAS1_{EYK1}$ upstream of the EYK1 promoter results in a 3.3-fold stronger promoter, thus stronger erythritol/erythrulose inducible promoter may be constructed by introducing additional tandem repeats of the $UAS1_{EYK1}$.

Example 5. UAS1B from XPR2 Enhanced Promoter Strength without Affecting Erythritol and Erythrulose Induction Madzak and colleagues reported that the fusion of four tandems repeats of UAS1B of XPR2 gene upstream of a minimal promoter of the LEU2 gene (yielding the so-called hp4d hybrid promoter) allowed a significant transcriptional activity (Madzak et al. 2000). In the same line, we combined four copies of $UAS1_{XPR2}$ (UAS1B) with the pEYK300 promoter leading to promoters HU4EYK300 (JME3998) (FIG. 5c). The latter was introduced into JMY2101 giving rise to strain JMY6380. The regulation of the pHU4EYK300 was investigated by monitoring cell growth and YFP fluorescence levels during culture of strain JMY6380 in YNB medium supplemented with erythritol (YNBOL), erythrulose (YNBOSE), glucose (YNBD) and glycerol (YNBG). As shown in FIG. 9b, YFP fluorescence, and therefore promoter induction were 17.1- and 9.8-fold higher in the presence of erythritol (YNOL medium) and erythrulose (YNBOSE) than for pEYK300 promoter (54063 mSFU and 47487 mSFU as compared to 3157 mSFU and 4844 mSFU, respectively). pHU4EYK was induced in stationary phase (i.e. after 60 h of culture, 63380 SFU) on glucose media (YNBD) in contrast to pEYK300 (344 SFU). Nevertheless, pHU4EYK was not found highly expressed on glycerol media.

Example 6. Hybrid Promoter HU4EYK300 is Inducible by Erythritol and Erythrulose

The regulation of the hybrid promoter pHU4EYK300 was characterized in the presence of a mixture of glycerol/erythritol or glycerol/erythrulose. These experiments were performed at steady state in chemostat culture in YNBG medium with CSP of erythritol or erythrulose. The regulation of pHU4EYK300 was investigated in regards to the growth rate of strain JMY6380 and the composition of the culture medium, more specifically in the presence of a mixture of glycerol/erythritol or glycerol/erythrulose.
Erythritol and Erythrulose Concentration Modulate the Strength pHU4EYK300 Induction in the Presence of Glycerol To assess the influence of inducer concentration on the regulation of pHU4EYK300, chemostat cultures of JMY6380 were performed on YNBG medium at a dilution rate of 0.2 $h^{-1}$. At steady state, different amount of erythritol or erythrulose were injected in the bioreactor to reach a final concentration of 0.2 and 0.6% (hereafter 0.2 CSP and 0.6

CSP, respectively) Glycerol, erythritol, erythrulose and YFP fluorescence were monitored for 8 h after inducer addition. In all experimental conditions tested, glycerol concentration remained almost constant (i.e. 3 g/l) in the bioreactor, confirming that a steady state was maintained in those experimental conditions.

As shown in FIG. 10, pHU4EYK300 induction level seems to be modulated by the inducer concentration in those experimental conditions (i.e. in the presence of glycerol). For 0.2 CSP, induction increased during the three first hours after inducer (erythritol and erythrulose) addition (FIG. 10a, 10c). Then after, when inducer concentration was below 1 g/L, it remained almost constant for the next six hours. By contrast, for 0.6 CSP, induction increased almost linearly during 8 h after inducer addition (FIG. 10b, 10d). It is worth mentioning that the amplitude of induction also seems to be correlated to the inducer concentration. The maximal YFP fluorescence and thus pHU4EYK300 induction, obtained after 8 hours of erythritol addition was higher for the 0.6 CSP than for the 0.2 CSP ($1.4 \times 10^3$ and $1.1 \times 10^3$ RFU, respectively). Similar observations were made for erythrulose. The maximal YFP fluorescence obtained 8 hours after erythrulose addition was higher for the 0.6 CSP than for the 0.2 CSP ($2.5 \times 10^3$ and $1.1 \times 10^3$ RFU, respectively). It could also be deduced from FIG. 10, that erythrulose yield to higher induction level than erythritol, even in the presence of 3 g/l of glycerol. These results obtained from a chemostat experiment confirm the observation made in FIG. 9b, i.e. pHU4EYK300 is a strong inducible promoter, responding to erythritol and even more to erythrulose as an inducer.

Example 7. Deletion of EYK1 Enhanced pEYK Expression

A disruption cassette was constructed as described in material and methods. The disruption cassette, carrying a URA3 marker, was introduced into Po1d, yielding strain RIY147 (eyk1::URA3). The marker was then excised with pRRQ2 (Fickers et al 2003), yielding an Δeyk1 strain (RIY176, Table 1). The expression cassette carrying pEYK300-YFP-LEU2ex was then introduced into RIY176, giving rise to strain RIY180 (JMY6637). Since Δeyk1 could not grow on erythritol and erythrulose as sole carbon source, strain JMY6637 was grown in the presence of glucose or glycerol, used as energy source. Therefore, JMY6245 (pEYK300-WT) and JMY6637 (pEYK300-eyk1Δ) grown in YNBDOL (glucose, erythritol), YNBGOL (glycerol, erythritol), YNBDOSE (glucose, erythrulose), YNBGOSE (glycerol, erythrulose). Induction of the promoters was followed over time in microplates with glucose or glycerol for growth (0.25%) and with erythritol or erythrulose for induction (0.25%).

As shown in FIG. 12, YFP expression in wild-type and eykΔ in the presence of erythritol occurred during the growth phase in media containing 0.25% of glucose or 0.25% of glycerol (FIG. 12a, 12b, respectively). YFP fluorescence at 34 h of growth being 8.3-fold and 7.8-fold higher in the EYK1 deleted strain compared to the wild-type in glucose and glycerol, respectively (25672 SFU versus 3078 SFU with glucose and 19478 SFU versus 2500 SFU with glycerol). In contrast, in presence of erythrulose, YFP expression in wild-type and Δeyk was somewhat delayed from the growth phase in media containing 0.25% of glucose or 0.25% of glycerol (FIG. 12c, 12d, respectively). However, YFP fluorescence being 4.9-fold and 2.6-fold higher in the deleted strain compared to the wild-type in glucose and glycerol, respectively (9106 SFU versus 2993 SFU with glucose and 7934 SFU versus 3564 SFU with glycerol).

For strain JMY6245 (pEYK300-WT), the rates of the increase of the YFP fluorescence in presence of erythritol were 97 FU/h and 83 FU/h in glucose and glycerol, respectively. While, in the mutant Δeyk, the rates of the increase of the YFP fluorescence were 10.5-fold higher (1034 FU/h and 875 FU/h in glucose and glycerol, respectively).

Similarly, in the presence of erythrulose higher induction levels were obtained for the Δeyk mutant (pEYK300-Δeyk1) as compared to the non-disrupted mutant (pEYK300-EYK1) The rate of YFP production in the mutant strain was 6.1-fold higher in glucose as compared to the wild-type strain (4000 FU/h and 347 FU/h, respectively). In the presence of glycerol, this increase was equal to and was 7.3-fold (2527 FU/h and 875 FU/h, respectively).

These results demonstrate that expression level could be further improved by using a strain deleted for the EYK1 gene. In such strain erythritol or erythrulose could be used as inducer and could be used independently having induction either during the growth phase or delayed from the growth phase.

Similarly, a disruption cassette was constructed as described in material and methods for the deletion of EYD1 gene. The disruption cassette, carrying a URA3 marker, was introduced into JMY2101, yielding strain RIY212 (eyd1::URA3). The marker was then excised with pRRQ2 (Fickers et al 2003), yielding an Δeyk1 strain (RIY225, Table 1). Such strain could also be used as recipient for gene expression or metabolic engineering using either pEYK1 or pEYK1 derivative promoters and/or pEYD1 or pEYD1 derivatives promoters.

Growth Rate has No Effect on PHU4EYK300 Induction.

Yeast cell physiology is directly influenced by the growth rate. With the aim to evaluate the influence of cell growth rate on pHU4EYK300 induction by erythritol, chemostat cultures were performed in YNBOL medium at two distinct dilution rates (i.e. 0.16 $h^{-1}$ and 0.08 $h^{-1}$). The fluorescence levels of YFP were monitored by flow cytometry in order to assess the induction level at the single cell level. No significant difference in the promoter induction levels could be observed for the two dilution rates tested (data not shown). Indeed, the mean relative fluorescence of the cell population was equal to 8.86±0.62 0.104 RFU at D=0.16 $h^{-1}$, and to 9.47±0.31 0.104 RFU at D=0.08 $h^{-1}$. Moreover, cytograms showed that the cell population is homogenously induced in presence of erythritol (FIG. 11).

Example 8. EYK1 Encoding Erythrulose Kinase as a Catabolic Selectable Marker for Genome Editing in the Non-Conventional Yeast *Yarrowia lipolytica*

Selectable markers are a central component of genome edition technologies. In the yeast *Yarrowia lipolytica*, these markers are based on auxotrophy (leucine, uracil), antibiotic resistance (hygromycin B) or carbon source utilisation (SUC2) (Barth and Gaillardin, 1996). Multi-step genome editions imply the use of multi-auxotrophic strains, and as a drawback their final utilization requires to complement, at least partly, the culture medium accordingly or to render strains prototroph. Dominant markers, such as the *E. coli* hph gene, conferring resistance to hygromycin B, could also be used. However, they remain difficult to handle in practice due to a high level of spontaneous resistance in transformed cells. Genes related to the catabolism of carbon sources, hereafter "catabolic selectable markers" (CSM), present the advantage of not being involved in essential metabolic pathways. For instance, SUC2 from *Saccharomyces cerevisiae* encoding invertase and conferring the ability of the recombinant strains to grow on sucrose has been developed as a CSM (Nicaud et al., 1989). However, its utilization is impaired by residual growth on sucrose impurities.

Here, EYK1 (YALI0F01606g) encoding an erythrulose kinase is reported as a novel CSM. Therefore, a Δeyk1 strain transformed with a DNA fragment carrying EYK1 under the control of the strong constitutive pTEF promoter could be screened for Ery$^+$ (erythritol positive) phenotype on YNB medium supplemented with erythritol (10 g/L, YNBE medium). To assess the fidelity of this novel CSM, LIP2 encoding the extracellular lipase lip2 (Pignede et al., 2000) was disrupted using EYK1 as CSM and compared to URA3 and LEU2 selectable markers for its efficiency. The disruption cassettes (DC) were constructed using a cloning-free strategy derived from the previously reported Cre-lox method (Fickers et al., 2003). This update combines directed fragment assembly based on SfiI recognition sequence (SRS) and PCR amplification. Indeed, an appropriate design of the five inner-degenerated nucleotides of SRS (i.e. GGCCNNNN↓NGGCC) allows a directed assembly of the DC constitutive elements prior its final release by PCR amplification. In a first step, the 5' and 3' flanking regions of the gene to be disrupted (i.e. LIP2, $P_{LIP2}$ and $T_{LIP2}$ fragments, respectively) and a selectable marker (i.e. URA3, LEU2, EYK1; rescued from JMP113, JMP114, RIP131, respectively) were amplified by PCR using primers LPR-F/LPR-R in order to introduce compatible SRS as illustrated in FIG. 13A. In a second step, amplicons were purified, digested with SfiI and ligated for 10 min at 25° C. after endonuclease elimination in an equimolar ratio (0.4 µM) with T4 DNA ligase (1 U, 20 µl final volume). Then, one µl of ligation product was used as a template for PCR amplification using primer pair LIP2-PF/LIP2-TR. The final DCs (MUT, MLT, MET; FIG. 13B) were purified, and used to transform *Y. lipolytica* strain Po1d (ura3-302, leu2-270, xpr2-322) or RIY146 (ura3-302, leu2-270, xpr2-322, eyk1::LEU2) using the lithium acetate method (Le Dall et al., 1994). Transformants were plated on YNBG (10 g/L glucose, MUT, MLT transformants) or YNBE (MET transformants) supplemented to meet the requirements of auxotrophs (Barth and Gaillardin, 1996) and grown at 30° C. Transformants carrying MET DC appeared on plates after 16 h by contrast to those carrying the auxotrophic marker that appeared between 48 and 72 h. Correctness of the disruption in strains RIY148, RIY149 and RIY201 (Table 1) was verified by analytical PCR using primer pair LPR-F/LIP2-V (FIG. 13A, data not shown). Correct disruption of LIP2 was found in 50% of the transformants with Ery$^+$ phenotype while a significantly lower yield (17% and 20%, respectively) was obtained for transformants with Leu$^+$ and Ura$^+$ phenotype, respectively.

To extend the utilisation of EYK1 as a CSM, a replicative vector, allowing transient expression of the Cre recombinase for marker excision (Fickers et al., 2003), was constructed based on that selectable marker. Briefly, pTEF-EYK1 fragment was amplified from RIP131 with primer pair EYK1-AF/EYK1-KR, digested by Apa1 and Kpn1, before being cloned at the corresponding site of pRRQ2 to yield RIP132 (hosted in strain RIE132). In strain RIY147 (Po1d eyk1::URA3), URA3 marker was excised with an efficiency of 80% and 50%, respectively, by using RIP132 (Cre-EYK1) and pRRQ2 (Cre-LEU2). In strain RIY203, correctness of URA3 excision was verified by analytical PCR (FIG. 14).

Through these results, EYK1 has been demonstrated as a suitable catabolic selectable marker for both targeted gene disruption and vector transformation. Compared to URA3 and LEU2 auxotrophic markers, transformants harboring EYK1 marker grow faster and marker excision was found to occur at a higher rate. Moreover, the cloning free method reported here for the construction of disruption cassettes renders genome edition in *Y. lipolytica* more straightforward.

Similarly, EYD1 could be used as a catabolic marker in strain RIY225 (Δeyd1) or any strain bearing a deletion in EYD1 gene.

Example 9. Construction of the New Host Strain JMY7126 for Protein Expression and Secretion Carrying Deletion of EYK1 Gene The host strain JMY1212 is deleted for the main protease, the alkaline extracellular protease Aep encoded by the XPR2 gene and the main lipases encoded by the LIP2, LIP7 and LIP8 genes. It contains a single auxotrophy for uracil (deletion of URA3 gene) (see Table 1). Therefore, only a single expression cassette could be introduced using URA3 marker. To perform further modifications such as insertion of an additional expression cassette or to introduce a gene deletion to improve secretion, the URA3 marker must be rescued using a replicative cre-hph vector by select on YPD hygromycin plate (Fickers et al. 2003).

The new host strain JMY7126 was constructed as described in FIG. 15 in order to introduce two additional gene deletions.

First, in order to introduce additional auxotrophy, we deleted the LYS5 gene coding for the saccharopine dehydrogenase (Xuan et al., 1990) resulting in lysine auxotrophy. The resulting strain JMY5207 was then transformed with the pUB-cre-hph to rescue uracyl auxotrophy. Secondly, deletion of the EYK1 gene involved in the catabolism of erythritol was introduced in order to, on one hand be able to use the newly developed method of marker rescues using cre-EYK1 replicative vector (FIG. 14 B) recently described by Vandermies et al, (2017) and on the other hand, to use the inducible pEYK1 hybrid promoters according to Trassaert et al 2017.

The host strain JMY7126 could be therefore used for enzyme engineering as JMY1212 taking advantage of the zeta platform or used for the construction of overproducing enzymes by construction of multiple copy strains using the two auxotrophies available uracil and lysine. This new strain contains the deletion of the EYK1 gene which allows better expression and induction upon erythritol induction.

Example 10. Expression of CalB Lipase Using Erythritol Inducible Promoter pEYK3AB (Also Named pEYK300A3B in FIG. 9 and Equivalent to pEYK1-3AB in FIG. 18)

For the construction of CalB overexpressing strains, expression cassettes pEYK3AB-CalB-URA3ex and pEYK3AB-CalB-LYS5ex were co-transformed into JMY7126 and selected on minimal YNB glucose medium. The transformants were first screened for their growth and lipase production. The transformant JMY7240, having the highest specific lipase activity, was selected for fermentation studies.

In a previous study, Trassaert and colleagues (2017) showed that the induction levels of pEYK1-derived promoters were dependent of the erythritol concentration in the culture medium, hence of the erythritol uptake by the cells. Recently, it was demonstrated that a high glycerol concentration negatively affects erythritol uptake by the cells (Carly et al., 2018). Fed-batch culture was tested to minimize glycerol concentration in the culture medium (in order to increase pEYK300A3B induction level), while providing sufficient energy to the cells. Strain JMY7240 was cultivated for 48 h in a 2 L fed-batch bioreactor, in YNBE liquid medium initially supplemented with 1 g/L glycerol. Based on anterior results (Carly et al., 2018), additional glycerol was added to the reactor at a feeding rate of 0.41 g/L·h for 24 h of culture, and then of 0.82 g/L·h for the next 24 h. These feeding values are both lower than the glycerol uptake capacity of *Y. lipolytica* at the considered biomass concentration. As shown in FIG. 16 A, the first feeding phase (0.41 g/L·h) allowed to reach a biomass higher than 3.3 g CDW/L (OD600=11.46±0.24), while the second feeding phase (0.82 g/L·h) provided a supplement of energy to the cells in order to stimulate the production of lipase CalB. Thus, lipase CalB was efficiently accumulated in the culture medium over time (FIG. 16 B), and a final lipase activity of 50,012±5,123 U/mL was reached (FIG. 16 A). Due to the higher increase of culture medium volume through glycerol feeding during the second phase, a lower volumetric production rate than in the first phase was observed (944±448 U/mL·h versus 1,140±234 U/mL·h). Nevertheless, the specific production rate was improved from the first phase to the second phase (342.34±63.45 U/gCDW·h versus 456.63±34.23 U/gCDW·h), which proves the efficiency of the glycerol feeding strategy.

Example 11. Tandem Repeats of UAS1 EYK1 Increase Promoter Strength Both in EYK1 Wild-Type (JMY1212) and in Mutant eyk1A Strain (JMY7126) Background Promoter Bricks Construction The first step was to construct different bio-brick for promoter analysis that will be compatible with our Golden Gate Assembly method (Celińska et al. 2017). We used different strategies to construct promoters bricks compatible with the *Y. lipolytica* GGAS. Firstly, the presence of internal BsaI sites within the promoter sequence was analyzed. Depending on the number of BsaI site, either they were eliminated by PCR mutagenesis, either a synthetic DNA fragment was purchased at GeneScript Biotech. Secondly, we added BsaI sites at both end of the promoter by PCR with the overhang required for a specific position of the GGAS. We designed P1 Promoters with the upstream overhang C (ACGG) and the downstream overhang D (AATG). Third, we purified the PCR product by gel extraction, cloned them into a TOPO vector (Table 1), and selected the recombinant plasmids in *E. coli*. Promoter cloning in TOPO was first verified by PCR on *E. coli* colonies followed by a migration of the PCR product on agarose gel. Finally, DNA was extracted from positive clones and verified by sequencing. Alternatively, promoters were purchased from GeneScript Biotech as DNA fragment or cloned into GeneScript Biotech vector (See Table 1).

Creation of Expression Cassettes by Golden Gate Assemblies for Promoter Analysis.

We decided to create assemblies with the GGAS between promoters, the fluorescent protein RedStarII and the Lip2 terminator as described in FIG. 17 using the BsaI sites C, D and L overhang according to the protocol described previously (Celińska et al. 2017). First, an intermediate GGAS was performed using GG bio-bricks containing the promoter with the overhang C (ACGG) and D (AATG) together with the fragment carrying the RedStarII with the Lip2 terminator as a RedStarII-Tlip2 (G1-T3) fragment with the overhangs D (AATG) and L (GAGT). The destination vector GGE114 (Table 1) was used for the GGAS, it contains the chromophore RFP (red fluorescent protein) giving red *E. coli* colony. The three corresponding fragments were assembled by adding equimolar concentration of each fragment followed by a digestion/ligation PCR as described in Material and methods.

The description of promoter construction with the promoter name, the forward and reverse primer pair used for amplification, the template used for PCR amplification, the *E. coli* strain containing the corresponding Golden Gate assembly and the representative *Y. lipolytica* transformant used for promoter analysis are summarized in Table 4.

TABLE 4

| | Primer | | Template | *E. coli* | *Y. lipolytica* strain | |
|---|---|---|---|---|---|---|
| Promoter | Forward | Reverse | used | strain | JMY1212 | JMY7126 |
| TEF1 | P1 TEF FW | P1 TEF RV | JME2928 | GGE085 | GGY037 | GGY109 |
| EYK1 | P1 EYK FW | P1 EYK RV | JME3934 | GGE238 | JMY7382 | JMY7384 |
| EYK1-2AB | P1 EYK FW | P1 EYK RV | synthesized | GGE0130 | GGY027 | GGY056 |
| EYK1-3AB | P1 EYK FW | P1 EYK RV | synthesized | GGE0104 | JMY7345 | JMY7394 |
| EYK1-4AB | P1 EYK FW | P1 EYK RV | synthesized | GGE0132 | GGY033 | GGY068 |
| EYK1-5AB | P1 EYK FW | P1 EYK RV | Synthesized | GGE250 | JMY7390 | JMY7392 |
| EYK1-4AB-Core TEF | — | — | Synthesized | JME4417 | JMY7325 | JMY7400 |
| EYD1AB | P1 EYD FW | P1 EYD RV | *Y. lipolytica* genomic DNA | GGE140 | JMY7386 | JMY7388 |
| EYD1A*B | P1 EYD FW EYD UAS1 MluI FW | EYD UAS1 MluI RV P1 EYD RV | GGE140 | GGE172 | JMY7398 | JMY7349 |
| EYD1AB* | P1 EYD FW EYD UAS2 MluI FW | EYD UAS2 MluI RV P1 EYD RV | GGE140 | GGE174 | JMY7396 | JMY7351 |

The resulting sequences of promoters are summarized in Table 5.

TABLE 5

Promoter sequence

| SEQ ID NO: | Promoter | Sequence * |
|---|---|---|
| 88 | TEF | GGTCTCTACGGGGGTTGGCGGCGTATTTGTGTCCCAAAAAACAGCCCCAAT<br>TGCCCCAATTGACCCCAAATTGACCCAGTAGCGGGCCCAACCCCGGCGAG<br>AGCCCCCTTCACCCCACATATCAAACCTCCCCCGGTTCCCACACTTGCCGT<br>TAAGGGCGTAGGGTACTGCAGTCTGGAATCTACGCTTGTTCAGACTTTGTA<br>CTAGTTTCTTTGTCTGGCCATCCGGGTAACCCATGCCGGACGCAAAATAGA<br>CTACTGAAAATTTTTTGCTTTGTGGTTGGGACTTTAGCCAAGGGTATAAAA<br>GACCACCGTCCCCGAATTACCTTTCCTCTTCTTTTCTCTCTCTCCTTGTCAA<br>CTCACACCCGAAGAATGAGAGACC |
| 89 | Core-TEF | GGTTGGGACTTTAGCCAAGGGTATAAAAGACCACCGTCCCCGAATTACCTT<br>TCCTCTTCTTTTCTCTCTCCTTGTCAACTCACACCCGAAGgatcccacaAATG<br>AGAGACC |
| 90 | EYK1 | GGTCTCTACGGatcgatTGCATCTACTTTTCTCTATACTGTACGTTTCAATCTG<br>GGGAAGCGGAATCCCAAAAGGGAAAGCCGCCGCATTAAGCTCCACAGCCT<br>TGCATAATCCGATGACCTGACTAGTGCGGACAAAGACTATTATTTCGAGGC<br>AAGGCCACCACGTACCGCGGTCCCAAACTTTTGCAAAGCTGAAAACAGCGT<br>GGGGGTCAACGTGGATCAGAAAGAGGGGCAGATCAGCTTCTATAAGAAGC<br>TCCTTTCCCCACAATTGGCCCACACGACACTTCTACACACTTACACATCTAC<br>TggatccATGAGAGACC |
| 91 | EYK1-2AB | GGTCTCTACGGCGATACGCGTATCGATGCATCTACTTTTCTCTATACTGTAC<br>GTTTCAATCTGGGGAAGCGGAATCCCAAAAGGGAAAGCCGCCGCATTAAG<br>CTCCACAGCGGGAAGCGGAATCCCAAAAGGGAAAGCCGCCGCATTAAGCT<br>CCACAGCCTTGCATAATCCGATGACCTGACTAGTGCGGACAAAGACTATTA<br>TTTCGAGGCAAGGCCACCACGTACCGCGGTCCCAAACTTTTGCAAAGCTGA<br>AAACAGCGTGGGGGTCAACGTGGATCAGAAAGAGGGGCAGATCAGCTTCT<br>ATAAGAAGCTCCTTTCCCCACAATTGGCCCACACGACACTTCTACACACTTA<br>CACATCTACTggatccATGAGAGACC |
| 92 | EYK1-3AB | GGTCTCTACGGCGATACGCGTatcgatGCATCTACTTTTCTCTATACTGTACGT<br>TTCAATCTGGGGAAGCGGAATCCCAAAAGGGAAAGCCGCCGCATTAAGCT<br>CCACAGCGGGAAGCGGAATCCCAAAAGGGAAAGCCGCCGCATTAAGCTCC<br>ACAGCGGGAAGCGGAATCCCAAAAGGGAAAGCCGCCGCATTAAGCTCCAC<br>AGCCTTGCATAATCCGATGACCTGACTAGTGCGGACAAAGACTATTATTTCG<br>AGGCAAGGCCACCACGTACCGCGGTCCCAAACTTTTGCAAAGCTGAAAACA<br>GCGTGGGGGTCAACGTGGATCAGAAAGAGGGGCAGATCAGCTTCTATAAG<br>AAGCTCCTTTCCCCACAATTGGCCCACACGACACTTCTACACACTTACACAT<br>CTACTggatccATGAGAGACC |
| 93 | EYK1-4AB | GGTCTCTACGGCGATACGCGTatcgatGCATCTACTTTTCTCTATACTGTACGT<br>TTCAATCTGGGGAAGCGGAATCCCAAAAGGGAAAGCCGCCGCATTAAGCT<br>CCACAGCGGGAAGCGGAATCCCAAAAGGGAAAGCCGCCGCATTAAGCTCC<br>ACAGCGGGAAGCGGAATCCCAAAAGGGAAAGCCGCCGCATTAAGCTCCACAG<br>CCTTGCATAATCCGATGACCTGACTAGTGCGGACAAAGACTATTATTTCGAG<br>GCAAGGCCACCACGTACCGCGGTCCCAAACTTTTGCAAAGCTGAAAACAGC<br>GTGGGGGTCAACGTGGATCAGAAAGAGGGGCAGATCAGCTTCTATAAGAA<br>GCTCCTTTCCCCACAATTGGCCCACACGACACTTCTACACACTTACACATCT<br>ACTggatccATGAGAGACC |
| 94 | EYK1-5AB | GGTCTCTACGGCGATACGCGTatcgatGCATCTACTTTTCTCTATACTGTACGT<br>TTCAATCTGGGGAAGCGGAATCCCAAAAGGGAAAGCCGCCGCATTAAGCT<br>CCACAGCGGGAAGCGGAATCCCAAAAGGGAAAGCCGCCGCATTAAGCTCC<br>ACAGCGGGAAGCGGAATCCCAAAAGGGAAAGCCGCCGCATTAAGCTCCAC<br>AGCGGGAAGCGGAATCCCAAAAGGGAAAGCCGCCGCATTAAGCTCCACAG<br>CGGGAAGCGGAATCCCAAAAGGGAAAGCCGCCGCATTAAGCTCCACAGCC<br>TTGCATAATCCGATGACCTGACTAGTGCGGACAAAGACTATTATTTCGAGG<br>CAAGGCCACCACGTACCGCGGTCCCAAACTTTTGCAAAGCTGAAAACAGCG<br>TGGGGGTCAACGTGGATCAGAAAGAGGGGCAGATCAGCTTCTATAAGAAG<br>CTCCTTTCCCCACAATTGGCCCACACGACACTTCTACACACTTACACATCTA<br>CTggatccATGAGAGACC |
| 95 | Core-EYK1 | CTGACTAGTGCGGACAAAGACTATTATTTCGAGGCAAGGCCACCACGTACC<br>GCGGTCCCAAACTTTTGCAAAGCTGAAAACAGCGTGGGGGTCAACGTGGA<br>TCAGAAAGAGGGGCAGATCAGCTTCTATAAGAAGCTCCTTTCCCCACAATT<br>GGCCCACACGACACTTCTACACACTTACACATCTACTggatccATGAGAGACC |
| 96 | EYK1-4AB-Core TEF | GGTCTCTACGGCGATACGCGTatcgatGCATCTACTTTTCTCTATACTGTACGT<br>TTCAATCTGGGGAAGCGGAATCCCAAAAGGGAAAGCCGCCGCATTAAGCT<br>CCACAGCGGGAAGCGGAATCCCAAAAGGGAAAGCCGCCGCATTAAGCTCC |

TABLE 5 -continued

Promoter sequence

| SEQ ID NO: | Promoter | Sequence * |
|---|---|---|
| | | ACAGCGGGAAGCGGAATCCCAAAAGGGAAAGCCGCCGCATTAAGCTCCAC<br>AGCGGGAAGCGGAATCCCAAAAGGGAAAGCCGCCGCATTAAGCTCCACAG<br>CCTTGCATAATCCGATGACCTGACTAGTGCGGTTGGGACTTTAGCCAAGGG<br>TATAAAAGACCACCGTCCCCGAATTACCTTTCCTCTTCTTTTCTCTCTCTCCT<br>TGTCAACTCACACCCGAAggatccCACAATGAGAGACC |
| 97 | EYD1AB | GGTCTCTACGGCCCatcgatGGAAACCTTAATAGGAGACTACTTCCGTTTCCT<br>AATTAGGACTTCCGCGACCCCAGACAAAGCGGCTTGGAGTAGGCCTCGTG<br>TCCGGCCTAGGGCAGAAACAGCTCCGGAACTCGATTGAGAAGCCGTACTC<br>TGGAAAGTCTAGAGGAAGTTCCAAGGTCGAGTCTCTTCGATATAAAAGGAC<br>GCCATGGAAG CTCTGTAGTTCGATATCAAATACTGACAACAGTTTCCAAACA<br>CACAAACACACACACACACACACACACACATACACAATGAGAGACC |
| 98 | EYD1A*B | GGTCTCTACGGCCCatcgatGGAAACCTTAATAGGAGACTACTTCCGACGCGT<br>TAATTAGGACTTCCGCGACCCCAGACAAAGCGGCTTGGAGTAGGCCTCGT<br>GTCCGGCCTAGGGCAGAAACAGCTCCGGAACTCGATTGAGAAGCCGTACT<br>CTGGAAAGTCTAGAGGAAGTTCCAAGGTCGAGTCTCTTCGATATAAAAGGA<br>CGCCATGGAAGCTCTGTAGTTCGATATCAAATACTGACAACAGTTTCCAAAC<br>ACACAAACACACACACACACACACACACACATACACAATGAGAGACC |
| 99 | EYD1AB* | GGTCTCTACGGCCCatcgatGGAAACCTTAATAGGAGACTACTTCCGTTTCCT<br>AATTAGGACTTCCGCGACCCCAGACAAAGCGGCTTGGAGTAGGCCTCGTG<br>TCCGGCCTAGGGCAGAAACAGCTCCGGAACTCGATACGCGTGCCGTACTC<br>TGGAAAGTCTAGAGGAAGTTCCAAGGTCGAGTCTCTTCGATATAAAAGGAC<br>GCCATGGAAG CTCTGTAGTTCGATATCAAATACTGACAACAGTTTCCAAACA<br>CACAAACACACACACACACACACACACACATACACAATGAGAGACC |
| 100 | Core-EYD1 | TAGAGGAAGTTCCAAGGTCGAGTCTCTTCGATATAAAAGGACGCCATGGAA<br>GCTCTGTAGTTCGATATCAAATACTGACAACAGTTTCCAAACACACAAACAC<br>ACACACACACACACACACACATACACAATGAGAGACC |

* BsaI site are underlined with the 4 bp overhang bolded, MluI site is underlined for EYD1A*B et EYD1 AB*. The ClaI and BamHI are in lower case, introduced to be compatible for promoter exchange into JMP62 type vector.

Tandem Repeats of UAS1$_{EYK1}$ Increase Promoter Strength in Both JMY1212 and JMY7126.

We showed that promoter strength was increased with the hybrid promoter pEYK300A3B composed of three repeats of the 48 bp UAS1$_{eyk1}$. Four new hybrid promoters were generated by fusing two, three, four, or five UAS1$_{EYK1}$ tandem elements taken from EYK1 promoter, named EYK1-2AB, EYK1-3AB, EYK1-4AB, and EYK1-5AB, respectively (FIG. 18b). All these promoters were synthesized with BsaI recognition site and 4 nt overhang for Golden Gate assembly from Genescript and cloned to Genescript plasmid. Each plasmid with synthetic promoter was assembled with RedStarII and Terminator LIP2 as described above. Then, the expression cassettes with several synthetic promoters were transformed into *Y. lipolytica* strain with two different genetic backgrounds, JMY1212 (EYK1) and JMY7126 (Δeyk1), respectively. Hybrid EYK1 promoter expression and strength were determined by following RedStarII expression and measuring the mean specific fluorescence rate (SFU/h) using erythritol for JMY1212 or Glucose+erythritol for JMY7126 as carbon source compared to glucose as carbon source, the results of which are in Table 6.

In strain JMY1212, activity increased slightly concomitantly to UAS1eyk1 copy number ranging from 0.54 to 4.42 SFU/h (Table 6). While SFU rate increased more significantly on erythritol medium, increasing from 2.28 SFU/h for EYK1 (one copy) up to 48.12 SFU/h for EYK1-5AB (5 copies). The fold induction also increased from 4.3-fold up to 19.0-fold. The optimum been observed for EYK1-4AB. In this growth condition, on glucose media EYK1 present a low expression, 0.54 SFU/h compared to TEF promoter which as an activity of 67.16 SFU/h. While in erythritol medium TEF promoter as a similar strength than on glucose, 65.42 SFU/h and EYK1-4AB is 48.12 SFU/h. Thus, the EYK hybrid promoter has a similar activity in inducible condition than the TEF promoter and has the strong advantage to be inducible.

In strain JMY7126, activity also increased concomitantly to UAS1eyk1 copy number ranging from 0.76 up to 13.15 SFU/h (Table 6). While SFU rate increased more significantly on erythritol media increasing from 7.13 for EYK1 (one copy) up to 90.15 for EYK1-5AB (5 copies).

The fold induction also increased from 9.4-fold up to 45.8-fold. The optimum been observed for EYK1-2AB. In this growth condition, on glucose media EYK1 present a low expression, 0.76 SFU/h compared to TEF promoter which as an activity of 24.11 SFU/h. While in erythritol medium TEF promoter as a slightly reduced strength, 17.45 SFU/h and EYK1-5AB is 90.15 SFU/h. In this condition and this strain background (strain deleted for EYK1 gene), the EYK1 hybrid promoter surpasses the TEF promoter being 5.16-fold stronger.

Example 12. Both UAS1$_{EYD1}$ and UAS2$_{EYD1}$ Give Rise to Inducible Promoter in Both EYK1 Wild-Type (JMY1212) and in Mutant eyk1Δ Strain (JMY7126) Background Two putative regulatory elements for the expression and regulation of the EYD1 gene (YALI0F01650g) by erythritol have been found by comparing the upstream DNA sequences of EYD1 homologs of the *Yarrowia* clade. We thus identified two-conserved consensus sequences of

[ANTTNNNTTTCCNNATNNGG] (within UAS1$_{EYD1}$ of sequence SEQ ID NO: 101 AAACCTTAATAGGAGAC-TACTTCCGTTTCCTAATTAGGACTTCCGCGACCCC) and [CGGNNCTNNATTGAGAANNC] (within UAS2$_{EYD1}$ of sequence SEQ ID NO: 102=GGGCAGAAACAGCTCCGGAACTCGATT-GAGAAGCCGTACTCTGGAAAGTC) within a 0.3 kb promoter region (FIG. 4). We analyzed both the expression and induction fold of the WT and mutated promoters (FIG. 18d). Mutation of the conserved (UAS1$_{EYD1}$) and (UAS2$_{EYD1}$) were performed by introducing a MluI site. The Box A, [ACTTCCGTTTCCTAATTAGG] was replaced by [ACTTCCGACGCGTAATTAGG] and named A*. The Box B, [CGGAACTCGATTGAGAAGCC] was replaced by [CGGAACTCGATACGCGTGCC] and named motif B*. This yielded to EYD1A*B and EYD1AB* promoters, respectively. Promoter strength and induction level was compared with the EYK1 and EYD1 promoter in the EYK1 Wild-type (JMY1212) and in mutant Δeyk1 strain (JMY7126) background (Table 6).

In strain JMY1212, pEYD1 allowed similar level of expression of RedStarII on glucose medium, 0.85 SFU/h, compared with the 0.54 SFU/h for pEYK1 in the same media. This promoter is also induced by erythritol giving 11.5 SFU/h compared with the 2.28 SFU/h for EYK1 (Table 6). Mutation of Box A completely abolish the expression of RedStarII on glucose medium, while it remains slightly expressed on erythritol giving 0.16 SFU/h, thus indicating that UAS1$_{EYD1}$ was important for expression and induction. On the opposite, mutation of Box B resulted only in a 2-fold reduction of RedStarII expression on glucose medium (0.43 SFU/h), while it remains more expressed on erythritol giving 2.57 SFU/h, thus indicating that UAS2$_{EYD1}$ was less important for expression and induction (Table 6). In contrast, unexpected expression level and fold induction were observed in JMY7126 which contains a deletion of the EYK1 gene on glucose+erythritol medium (Table 6). While expression on glucose medium, expression level remains low, at about 0.54 SFU/h, EYD1 promoter displayed greater expression level ranging from 245.27 to 457.51 SFU/h on glucose+erythritol media showing a tremendous fold induction ranging from 357.6 to 896.1-fold. Thus, indicating that both UAS1$_{EYD1}$ and UAS2$_{EYD1}$ were important for expression and induction in this genetic background and growth condition.

CONCLUSIONS

Several groups have constructed hybrid promoters based on combination of tandem repeats of upstream activating sequence (UAS), TATA box and core promoter for gene expression in *Yarrowia lipolytica* (Madzak et al. 2000; Blazeck et al. 2011; Blazeck et al. 2013; Hussain et al. 2016). This gave rise to hybrid promoters with various strengths, up to 10-fold higher expression than the constitutive pTEF promoter (Muller et al, 1998). This later one being a constitutive strong promoter commonly used for gene expression and for promoter strength comparison. Among them they are few strong inducible promoters such as ICL1, LIP2, POX2 (Juretzek et al 2000, Pignede et al 2000, Sassi et al 2016). The LIP2 and POX2 promoters are inducible by oleic acid which has the drawback to require oil emulsion for induction. The inventors have identified a short nucleotide sequence acting as an upstream activating sequence may be conferring inducibility by erythritol or by erythrulose. The present invention provides new promoters allowing at least a 10-fold higher expression than the pTEF promoter. This open the path to the design of new synthetic promoters containing UAS$_{EYK}$ and/or URS$_{EYK}$ with higher tandem repeats number or with various core promoters to further wide the expression range and the induction profiles.

The promoters of the invention are poorly induced by glucose or glycerol. They could be induced by erythritol or by erythrulose with a tremendous advantage of being dose dependent thus allowing fine tuning of induction which will permit to modulate the degrees of expression that could be obtained. The inducible promoters and the nucleotide sequence according to the invention contained therein, expand the parts available for protein synthesis and for the development of tools for genetic engineering such as additional marker for gene deletion or marker rescue and for inducible expression of genes, in particular for genome editing. The present invention could be also a powerful tool for fundamental research.

REFERENCES

Barbier, T., Collard, F., Zúñiga-Ripa, A., Moriyón, I., Godard, T., Becker, J., Wittmann, C., Van Schaftingen, E., Letesson, J.-J., 2014. Erythritol feeds the pentose phosphate pathway via three new isomerases leading to D-erythrose-4-phosphate in *Brucella*. Proc Natl Acad Sci USA 111, 17815-17820. doi:10.1073/pnas.1414622111.

TABLE 6

Overall summary of promoter expression and induction level in the two strains.

| Promoter | JMY1212 | | | JMY7126 | | |
| --- | --- | --- | --- | --- | --- | --- |
| | Glucose | Erythritol | Fold change | Glucose | Glucose + Erythritol | Fold change |
| TEF | 67.16 ± 3.87 | 65.42 + 0.17 | 1.0 | 24.11 ± 1.88 | 17.45 ± 0.39 | 0.7 |
| EYK1 | 0.54 ± 0.23 | 2.28 ± 0.04 | 4.3 | 0.76 ± 0.13 | 7.13 ± 0.51 | 9.4 |
| EYK1-2AB | 2.63 ± 0.38 | 15.55 ± 0.55 | 5.9 | 1.41 ± 0.57 | 64.48 ± 0.49 | 45.8 |
| EYK1-3AB | 1.68 ± 1.44 | 26.76 ± 0.38 | 15.9 | 3.23 ± 1.39 | 84.41 ± 4.55 | 26.1 |
| EYK1-4AB | 2.39 ± 0.88 | 45.50 ± 2.70 | 19.0 | 8.18 ± 0.07 | 84.29 ± 5.21 | 10.3 |
| EYK1-5AB | 4.42 ± 0.09 | 48.12 ± 3.43 | 10.9 | 13.15 ± 0.81 | 90.15 ± 0.30 | 6.9 |
| EYK1-4AB-coreTEF | 23.57 ± 1.37 | 80.14 ± 7.06 | 3.4 | 35.53 ± 3.73 | 340.52 ± 16.45 | 9.6 |
| EYD1AB | 0.85 ± 0.54 | 11.50 ± 0.25 | 13.4 | 0.67 ± 1.52 | 457.51 ± 11.37 | 682.5 |
| EYD1A*B | — | 0.16 ± 0.32 | — | 0.54 ± 0.88 | 194.50 ± 11.50 | 357.6 |
| EYD1AB* | 0.43 ± 1.09 | 2.57 ± 0.66 | 5.9 | 0.27 ± 0.15 | 245.27 ± 14.56 | 896.1 |

Barth, G., Gaillardin, C., 1996. *Yarrowia lipolytica*, in: Nonconventional Yeasts in Biotechnology. Springer Berlin Heidelberg, pp. 313-388.

Beopoulos, A., Cescut, J., Haddouche, R., Uribelarrea, J.-L., Molina-Jouve, C., Nicaud, J.-M., 2009. *Yarrowia lipolytica* as a model for bio-oil production. Progress in Lipid Research 48, 375-387. doi:10.1016/j.plipres.2009.08.005.

Beopoulos, A., Nicaud, J.-M., Gaillardin, C., 2011. An overview of lipid metabolism in yeasts and its impact on biotechnological processes. Appl Microbiol Biotechnol 90, 1193-1206. doi:10.1007/s00253-011-3212-8.

Blazeck, J., Liu, L., Redden, H., Alper, H., 2011. Tuning Gene Expression in *Yarrowia lipolytica* by a Hybrid Promoter Approach [V]. Appl Environ Microbiol 77, 7905-7914. doi:10.1128/AEM.05763-11.

Blazeck, J., Reed, B., Garg, R., Gerstner, R., Pan, A., Agarwala, V., Alper, H. S., 2013. Generalizing a hybrid synthetic promoter approach in *Yarrowia lipolytica*. Appl Microbiol Biotechnol 97, 3037-3052. doi:10.1007/s00253-012-4421-5.

Blazeck, J., Hill, A., Liu, L., Knight, R., Miller, J., Pan, A., Otoupal, P., Alper, H. S., 2014. Harnessing *Yarrowia lipolytica* lipogenesis to create a platform for lipid and biofuel production. Nature Communications 5, 3131. doi: 10.1038/ncomms4131.

Bordes, F., Fudalej F., Dossat V., Nicaud J. M., and Marty. A., 2007. A new recombinant protein expression system for high-throughput screening in the yeast *Yarrowia lipolytica*. J Microbiol Methods 70:493-502.

Carly, F., Gamboa-Melendez, H., Vandermies M., Damblon C., Nicaud J. M., Fickers, P., 2017. Identification and characterization of EYK1, a key gene for erythritol catabolism in *Yarrowia lipolytica*. Applied Appl Microbiol Biotechnol. September; 101(17):6587-6596. doi: 10.1007/s00253-017-8361-y. Epub 2017 Jun. 12.

Carly, F., Steels, S., Telek, S., Vandermies, M., Nicaud, J. M., Fickers, P. 2018. Identification and characterization of EYD1, encoding an erythritol dehydrogenase in *Yarrowia lipolytica* and its application to bioconvert erythritol into erythrulose. Bioresource technology, 247: 963-969. doi/10.1016/j.biortech.2017.09.168.

Celińska, E., Ledesma Amaro, R., Larroudé, M., Rossignol, T., Pauthenier, C., Nicaud, J.-M., 2017. Golden Gate Assembly system dedicated to complex pathway manipulation in *Yarrowia lipolytica*. Microbial Biotechnology, 10 (2), 450-455. DOI: 10.1111/1751-7915.12605.

Dulermo, R., Brunel, F., Dulermo, T., Ledesma-Amaro, R., Vion, J., Trassaert, M., Thomas, S., Nicaud, J.-M., Leplat, C., 2017. Using a vector pool containing variable-strength promoters to optimize protein production in *Yarrowia lipolytica*. Microb Cell Fact 16. doi:10.1186/s12934-017-0647-3.

Emond, S., Montanier, C., Nicaud, J. M., Marty, A., Monsan, P., Andre, I., Remaud-Simeon, M., 2010. New efficient recombinant expression system to engineer *Candida antarctica* lipase B. Appl Environ Microbiol 76:2684-2687.

Fickers, P., Le Dall, M., Gaillardin, C., Thonart, P., Nicaud, J., 2003. New disruption cassettes for rapid gene disruption and marker rescue in the yeast *Yarrowia lipolytica*. Journal of Microbiological Methods 55, 727-737. doi: 10.1016/j.mimet.2003.07.003.

Fickers, P., Benetti, P., Wache, Y., Marty, A., Mauersberger, S., Smit, M., Nicaud, J., 2005. Hydrophobic substrate utilisation by the yeast *Yarrowia lipolytica*, and its potential applications. FEMS Yeast Research 5, 527-543. doi: 10.1016/j.femsyr.2004.09.004.

Friedlander, J., Tsakraklides, V., Kamineni, A., Greenhagen, E. H., Consiglio, A. L., MacEwen, K., Crabtree, D. V., Afshar, J., Nugent, R. L., Hamilton, M. A., Joe Shaw, A., South, C. R., Stephanopoulos, G., Brevnova, E. E., 2016. Engineering of a high lipid producing *Yarrowia lipolytica* strain. Biotechnology for Biofuels 9, 77. doi:10.1186/s13068-016-0492-3.

Gajdoš, P., Ledesma-Amaro, R., Nicaud, J. M., Čertik, M., Rossignol, T., 2016. Overexpression of DGAT in *Yarrowia lipolytica* affects lipid body size, number, and distribution. FEMS Yeast Res. 2016 Aug. 8. pii: fow062. [Epub ahead of print], DOI: 10.1093/femsyr/fow062.

Groenewald, M., Boekhout, T., Neuvéglise, C., Gaillardin, C., van Dijck, P. W. M., Wyss, M., 2014. *Yarrowia lipolytica*: Safety assessment of an oleaginous yeast with a great industrial potential. Critical Reviews in Microbiology 40, 187-206. doi:10.3109/1040841X.2013.770386.

Haddouche R., Delessert S., Sabirova J., Neuvéglise C., Poirier Y., Nicaud J. M. 2010. Roles of multiple acyl-CoA oxidases in the routing of carbon flow towards ß-oxidation and polyhydroxyalkanoate biosynthesis in *Yarrowia lipolytica*. FEMS Yeast Res 10: 917-927.

Hong, S.-P., Seip, J., Walters-Pollak, D., Rupert, R., Jackson, R., Xue, Z., Zhu, Q., 2012. Engineering *Yarrowia lipolytica* to express secretory invertase with strong FBA1IN promoter. Yeast 29, 59-72. doi:10.1002/yea.1917.

Hussain, M. S., Gambill, L., Smith, S., Blenner, M. A., 2016. Engineering promoter architecture in oleaginous yeast *Yarrowia lipolytica*. ACS Synth Biol 5, 213-223. doi: 10.1021/acssynbio.5b00100.

Juretzek, T., Wang, H.-J., Nicaud, J.-M., Mauersberger, S., Barth, G., 2000. Comparison of promoters suitable for regulated overexpression of β-galactosidase in the alkane-utilizing yeast *Yarrowia lipolytica*. Biotechnol. Bioprocess Eng. 5, 320-326. doi:10.1007/BF02942206.

Juretzek T, Mauersberger S, Barth G, Le Dall M-T, Gaillardin C, Nicaud J-M (2001). Vectors for gene expression and amplification in the yeast *Yarrowia lipolytica*. Yeast 18:97-113.

Le Dall, M. T., Nicaud, J. M., Gaillardin, C., 1994. Multiple-copy integration in the yeast *Yarrowia lipolytica*. Curr. Genet. 26, 38-44.

Ledesma-Amaro, R., Nicaud, J.-M., 2016. *Yarrowia lipolytica* as a biotechnological chassis to produce usual and unusual fatty acids. Progress in Lipid Research 61, 40-50. doi:10.1016/j.plipres.2015.12.001.

Madzak, C., Tréton, B., Blanchin-Roland, S., 2000. Strong hybrid promoters and integrative expression/secretion vectors for quasi-constitutive expression of heterologous proteins in the yeast *Yarrowia lipolytica*. J. Mol. Microbiol. Biotechnol. 2, 207-216.

Livak, K. J., Schmittgen, T. D., 2001. Analysis of relative gene expression data using realtime quantitative PCR and the 2-ΔΔCT method. Methods 25, 402-408.

Madzak, C., Beckerich, J.-M., 2013. Heterologous Protein Expression and Secretion in *Yarrowia lipolytica*, in: Barth, G. (Ed.), *Yarrowia Lipolytica*, Microbiology Monographs. Springer Berlin Heidelberg, pp. 1-76.

Madzak, C., 2015. *Yarrowia lipolytica*: recent achievements in heterologous protein expression and pathway engineering. Appl. Microbiol. Biotechnol. 99, 4559-4577. doi: 10.1007/s00253-015-6624-z.

Muller, S., Sandal, T., Kamp-Hansen, P., Dalbøge, H., 1998. Comparison of expression systems in the yeasts *Saccharomyces cerevisiae, Hansenula polymorpha, Klyveromyces lactis, Schizosaccharomyces pombe* and *Yarrowia* lipolytica. Cloning of two novel promoters from *Yarrowia lipolytica*. Yeast 14, 1267-1283. doi:10.1002/(SICI)1097-0061(1998100)14:14<1267::AID-YEA327>3.0. CO; 2-2.

Nicaud J-M., Fabre E., Gaillardin C. 1989 Expression of invertase activity in *Yarrowia lipolytica* and its use as a selective marker. Cur. Genet. 16:253-260.

Nicaud, J-M, Madzak, C., van den Broek, P., Gysler, C., Duboc, P., Niederberger, P. Gaillardin, C., 2002. Protein expression and secretion in the yeast *Yarrowia lipolytica*. FEMS Yeast Research 2/3:371-379.

Nicaud, J.-M., 2012. *Yarrowia lipolytica*. Yeast 29, 409-418. doi:10.1002/yea.2921

Ogrydziak, D. M., Scharf, S. J., 1982. Alkaline extracellular protease produced by *Saccharomycopsis lipolytica* CX161-1B. J. Gen. Microbiol. 128, 1225-1234. doi: 10.1099/00221287-128-6-1225.

Paradowska, K., Nitka, D., 2009. Purification and characterization of erythritol dehydrogenase from *Mycobacterium smegmatis*. Annales UMCS, Pharmacia 22, 47-55. doi:10.2478/v10080-008-0177-8.

Pignède, G., Wang, H., Fudalej, F., Gaillardin, C., Seman, M., Nicaud, J.-M., 2000. Characterization of an Extracellular Lipase Encoded by LIP2 in *Yarrowia lipolytica*. J Bacteriol 182, 2802-2810.

Querol, A., Barrio, E., Huerta, T., Ramón, D., 1992. Molecular Monitoring of Wine Fermentations Conducted by Active Dry Yeast Strains. Appl Environ Microbiol 58, 2948-2953.

Richard, M., Quijano, R. R., Bezzate, S., Bordon-Pallier, F., Gaillardin, C., 2001. Tagging morphogenetic genes by insertional mutagenesis in the yeast *Yarrowia lipolytica*. J. Bacteriol. 183, 3098-3107.

Sambrook, J., Fritsch, E. F., Maniatis, T., 1989. Molecular cloning: a laboratory manual, 3rd ed. ed. Cold Spring Harbor Laboratory Press, NY, USA.

Sassi, H., Delvigne, F., Kar, T., Nicaud, J.-M., Coq, A.-M. C.-L., Steels, S., Fickers, P., 2016. Deciphering how LIP2 and POX2 promoters can optimally regulate recombinant protein production in the yeast *Yarrowia lipolytica*. Microb Cell Fact 15, 159. doi:10.1186/s12934-016-0558-8.

Schmid-Berger N., Schmid B., Barth G. 1994. Ylt1, a highly repetitive retrotransposon in the genome of the dimorphic fungus *Yarrowia lipolytica*. J Bacteriol 176: 2477-2482.

Sibirny, A. A., Madzak, C., Fickers, P., 2014. Genetic engineering of non-conventional yeast for the production of valuable compounds, in: Microbial Biotechnology Progress and Trends. CRC Press, USA, pp. 63-112.

Sievers, F., Wilm, A., Dineen, D., Gibson, T. J., Karplus, K., Li, W., Lopez, R., McWilliam, H., Remmert, M., Söding, J., Thompson, J. D., Higgins, D. G., 2011. Fast, scalable generation of high-quality protein multiple sequence alignments using Clustal Omega. Mol Syst Biol. October 11; 7:539. doi: 10.1038/msb.2011.75.

Tai, M., Stephanopoulos, G., 2013. Engineering the push and pull of lipid biosynthesis in oleaginous yeast *Yarrowia lipolytica* for biofuel production. Metabolic Engineering 15, 1-9. doi:10.1016/j.ymben.2012.08.007.

Thevenieau, F., Nicaud, J.-M., 2013. Microorganisms as sources of oils. OCL 20, D603. doi:10.1051/ocl/2013034.

Trassaert, M., Vandermies, M., Carly, F., Denies, O., Thomas, S., Fickers, P., Nicaud, J.-M. 2017. New inducible promoter for gene expression and synthetic biology in *Yarrowia lipolytica*. Microbial Cell Factories, 16., DOI: 10.1186/s12934-017-0755-0.

Vandermies, M., Denies, O., Nicaud, J.-M., Fickers, P., 2017. EYK1 encoding erythrulose kinase as a catabolic selectable marker for genome editing in the non-conventional yeast *Yarrowia lipolytica*. Journal of Microbiological Methods, 139, 161-164., DOI: 10.1016/j.mimet.2017.05.012.

Wang, X., Sun, Y., Ke, F., Zhao, H., Liu, T., Xu, L., Liu, Y., Yan, Y., 2012. Constitutive expression of *Yarrowia lipolytica* lipase LIP2 in *Pichia pastoris* using GAP as promoter. Appl Biochem Biotechnol 166, 1355-1367. doi:10.1007/s12010-011-9524-4

Xuan J W, Fournier P, Declerck N, Chasles M, Gaillardin C. 1990. Overlapping reading frames at the LYS5 locus in the yeast *Yarrowia lipolytica*. Mol Cell Biol. 10:4795-806.

Zinjarde, S. S., 2014. Food-related applications of *Yarrowia lipolytica*. Food Chemistry 152, 1-10. doi:10.1016/j.foodchem.2013.11.117.

The invention claimed is:

1. A method for expressing a gene or producing an encoded protein, comprising the steps of
   a) growing in vitro, in a culture medium, a host cell comprising
      an erythritol-inducible promoter sequence, an erythrulose-inducible promoter sequence or an erythritol- and erythrulose-inducible promoter sequence functional in yeast comprising a core promoter, and a nucleotide sequence comprising tandem repeats of a sequence according to formula (I) and/or tandem repeats of a sequence according to formula (II), wherein:
   formula (I) is $$CGGNNX_1CNNNANNX_2GNNAAGNCG \quad (I)$$

with N being any nucleotide
   with $X_1$ and $X_2$ being any nucleotide or no nucleotide,
   formula (II) is $$ANTTNNNTTTCCNNATNNGG \quad (II)$$

with N being any nucleotide,
   operably linked to a polynucleotide sequence encoding a gene product to be transcribed from said inducible promoter and
   b) adding erythritol and/or erythrulose to the culture medium.

2. The method according to claim 1, wherein the sequence according to formula (I) is selected in the group consisting of:

CGGVWYCYBVAWDGRRAAGSCG,  (SEQ ID NO: 6)

CGGVWCYBVAWDKGRRAAGSCG,  (SEQ ID NO: 7)

CGGVWYCYBVAWDKGRRAAGSCG, and  (SEQ ID NO: 8)

CGGVWCYBVAWDGRRAAGSCG.  (SEQ ID NO: 9)

3. The method according to claim 1, wherein the sequence according to formula (I) is selected in the group consisting of SEQ ID NO: 1, SEQ ID NO: 2, SEQ ID NO: 4, SEQ ID NO: 6, SEQ ID NO: 7 and SEQ ID NO: 9.

4. The method according to claim 1, wherein the sequence according to formula (II) is ABTTSYRTTTCCY-WATDHGG (SEQ ID NO: 10).

5. The method according to claim 1, wherein said nucleotide sequence contains from 2 to 32 copies of the sequence according to formula (I) and/or the sequence according to formula (II).

6. The method according to claim 1, wherein said nucleotide sequence comprises at least one sequence according to formula (I) and further comprises at least one sequence according to formula (III) which is $$CNTGCATNATCCGANGAC \quad (III)$$

with N being any nucleotide.

7. The method according to claim 6, wherein the sequence according to formula (III) is CDTGCATWATCCGAYGAC as set forth in SEQ ID NO: 12.

8. The method according to claim 1, wherein said nucleotide sequence comprises the sequence as set forth in SEQ ID NO: 13.

9. The method according to claim 1 wherein at least one sequence according to formula (I) and/or at least one sequence according to formula (II) is/are upstream to an ATG of the polynucleotide sequence.

10. The method according to claim 9, wherein said at least one sequence according to formula (I) and/or said at least one sequence according to formula (II) is/are from −800 to −50 of the ATG.

11. The method of claim 1 wherein said core promoter is selected from the group consisting of TEF core promoter, EYK1 core promoter, EYD1 core promoter, POX2 core promoter, LEU2 core promoter and PAT1 core promoter.

12. The method of claim 1, wherein said erythritol-inducible promoter sequence, erythrulose-inducible promoter sequence, or erythritol and erythrulose-inducible promoter sequence comprises at least one promoter regulatory sequence selected from the group consisting of UAS, TATA box and URS.

13. The method of claim 1, wherein an endogenous gene encoding L-erythrulose kinase is inhibited in the host cell.

14. The method of claim 1, an endogenous gene encoding erythritol dehydrogenase is inhibited in the host cell.

15. The method of claim 12, wherein said promoter regulatory sequence is a regulatory sequence of a promoter selected from the group consisting of XPR2, TEF, POX2, LEU2, PAT1 and LIP2.

16. The method of claim 1, wherein an endogenous gene encoding L-erythrulose kinase is deleted in the host cell.

17. The method of claim 1, wherein an endogenous gene encoding erythritol dehydrogenase is deleted in the host cell.

* * * * *

SEQUENCE LISTING

```
<160> NUMBER OF SEQ ID NOS: 102

<210> SEQ ID NO 1
<211> LENGTH: 22
<212> TYPE: DNA
<213> ORGANISM: Artificial
<220> FEATURE:
<223> OTHER INFORMATION: Formula (I) with X1 = N; X2 = nothing
<220> FEATURE:
<221> NAME/KEY: misc_feature
<222> LOCATION: (4)..(6)
<223> OTHER INFORMATION: n is a, c, g, or t
<220> FEATURE:
<221> NAME/KEY: misc_feature
<222> LOCATION: (8)..(10)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
```

```
<221> NAME/KEY: misc_feature
<222> LOCATION: (20)..(20)
<223> OTHER INFORMATION: n is a, c, g, or t

<400> SEQUENCE: 1
cggnnncnnn anngnnaagn cg                                              22

<210> SEQ ID NO 2
<211> LENGTH: 22
<212> TYPE: DNA
<213> ORGANISM: Artificial
<220> FEATURE:
<223> OTHER INFORMATION: Formula (I) with X1 = nothing; X2 = N
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(9)
<223> OTHER INFORMATION: n is a, c, g, or t
<220> FEATURE:
<221> NAME/KEY: misc_feature
<222> LOCATION: (11)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 2
cggnncnnna nnngnnaagn cg                                              22

<210> SEQ ID NO 3
<211> LENGTH: 23
<212> TYPE: DNA
<213> ORGANISM: Artificial
<220> FEATURE:
<223> OTHER INFORMATION: Formulat (I) with X1 = N; X2 = N
<220> FEATURE:
<221> NAME/KEY: misc_feature
<222> LOCATION: (4)..(6)
<223> OTHER INFORMATION: n is a, c, g, or t
<220> FEATURE:
<221> NAME/KEY: misc_feature
<222> LOCATION: (8)..(10)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 3
cggnnncnnn annngnnaag ncg                                             23

<210> SEQ ID NO 4
<211> LENGTH: 21
<212> TYPE: DNA
<213> ORGANISM: Artificial
<220> FEATURE:
<223> OTHER INFORMATION: Formula (I) with X1 = nothing; X2 = nothing
```

```
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(9)
<223> OTHER INFORMATION: n is a, c, g, or t
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 4
cggnncnnna nngnnaagnc g                                              21

<210> SEQ ID NO 5
<211> LENGTH: 20
<212> TYPE: DNA
<213> ORGANISM: Artificial
<220> FEATURE:
<223> OTHER INFORMATION: Formula (II)
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(7)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t

<400> SEQUENCE: 5
anttnnnttt ccnnatnngg                                                20

<210> SEQ ID NO 6
<211> LENGTH: 22
<212> TYPE: DNA
<213> ORGANISM: Artificial
<220> FEATURE:
<223> OTHER INFORMATION: Preferred formula (I) with X1 = N; X2 = nothing

<400> SEQUENCE: 6
cggvwycybv awdgrraags cg                                             22

<210> SEQ ID NO 7
<211> LENGTH: 22
<212> TYPE: DNA
<213> ORGANISM: Artificial
<220> FEATURE:
<223> OTHER INFORMATION: Preferred formula (II) with X1 = nothing; X2 =
      N

<400> SEQUENCE: 7
cggvwcybva wdkgrraags cg                                             22
```

```
<210> SEQ ID NO 8
<211> LENGTH: 23
<212> TYPE: DNA
<213> ORGANISM: Artificial
<220> FEATURE:
<223> OTHER INFORMATION: Preferrred formulat (I) with X1 = N; X2 = N

<400> SEQUENCE: 8
cggvwycybv awdkgrraag scg                                            23

<210> SEQ ID NO 9
<211> LENGTH: 21
<212> TYPE: DNA
<213> ORGANISM: Artificial
<220> FEATURE:
<223> OTHER INFORMATION: Preferrred formula (I) with X1 = nothing; X2 =
      nothing

<400> SEQUENCE: 9
cggvwcybva wdgrraagsc g                                              21

<210> SEQ ID NO 10
<211> LENGTH: 20
<212> TYPE: DNA
<213> ORGANISM: Artificial
<220> FEATURE:
<223> OTHER INFORMATION: Preferred formula (II)

<400> SEQUENCE: 10
abttsyrttt ccywatdhgg                                                20

<210> SEQ ID NO 11
<211> LENGTH: 18
<212> TYPE: DNA
<213> ORGANISM: Artificial
<220> FEATURE:
<223> OTHER INFORMATION: Formula (III)
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 11
cntgcatnat ccgangac                                                  18

<210> SEQ ID NO 12
<211> LENGTH: 18
<212> TYPE: DNA
<213> ORGANISM: Artificial
<220> FEATURE:
<223> OTHER INFORMATION: Preferred formula (III)

<400> SEQUENCE: 12
cdtgcatwat ccgaygac                                                  18

<210> SEQ ID NO 13
<211> LENGTH: 48
<212> TYPE: DNA
<213> ORGANISM: Artificial
<220> FEATURE:
<223> OTHER INFORMATION: 48bp UAS1EYK1 fragment encompassing the Box A
```

-continued

```
<400> SEQUENCE: 13
gggaagcgga atcccaaaag ggaaagccgc cgcattaagc tccacagc          48

<210> SEQ ID NO 14
<211> LENGTH: 23
<212> TYPE: DNA
<213> ORGANISM: Artificial
<220> FEATURE:
<223> OTHER INFORMATION: EYK-P-L

<400> SEQUENCE: 14
gttgtgtgat gagaccttgg tgc                                    23

<210> SEQ ID NO 15
<211> LENGTH: 37
<212> TYPE: DNA
<213> ORGANISM: Artificial
<220> FEATURE:
<223> OTHER INFORMATION: EYK-P-R-SfiI

<400> SEQUENCE: 15
aaaggccatt taggccgcag ctcctccgac aatcttg                     37

<210> SEQ ID NO 16
<211> LENGTH: 37
<212> TYPE: DNA
<213> ORGANISM: Artificial
<220> FEATURE:
<223> OTHER INFORMATION: EYK-T-L-SfiI

<400> SEQUENCE: 16
taaggccttg atggccacaa gtagagggag gagaagc                     37

<210> SEQ ID NO 17
<211> LENGTH: 22
<212> TYPE: DNA
<213> ORGANISM: Artificial
<220> FEATURE:
<223> OTHER INFORMATION: EYK-T-R

<400> SEQUENCE: 17
gtttaggtgc ctgaagacgg tg                                     22

<210> SEQ ID NO 18
<211> LENGTH: 24
<212> TYPE: DNA
<213> ORGANISM: Artificial
<220> FEATURE:
<223> OTHER INFORMATION: EYK-V1

<400> SEQUENCE: 18
cgtacccgag attgtactgt tgtc                                   24

<210> SEQ ID NO 19
<211> LENGTH: 22
<212> TYPE: DNA
<213> ORGANISM: Artificial
<220> FEATURE:
<223> OTHER INFORMATION: EYK-V2

<400> SEQUENCE: 19
cataaccgcc taccctttgta gc                                    22

<210> SEQ ID NO 20
```

```
<211> LENGTH: 49
<212> TYPE: DNA
<213> ORGANISM: Artificial
<220> FEATURE:
<223> OTHER INFORMATION: EYK1-AF

<400> SEQUENCE: 20
ttcttgggcc cggcctaaat ggccctgtta tccctagatc gatatagag            49

<210> SEQ ID NO 21
<211> LENGTH: 48
<212> TYPE: DNA
<213> ORGANISM: Artificial
<220> FEATURE:
<223> OTHER INFORMATION: EYK1-KR

<400> SEQUENCE: 21
aataaggtac cggccatcaa ggccattcga tttgtcttag aggaacgc             48

<210> SEQ ID NO 22
<211> LENGTH: 20
<212> TYPE: DNA
<213> ORGANISM: Artificial
<220> FEATURE:
<223> OTHER INFORMATION: EYD-P-Fo

<400> SEQUENCE: 22
aagcgtccga gactgtcgga                                            20

<210> SEQ ID NO 23
<211> LENGTH: 36
<212> TYPE: DNA
<213> ORGANISM: Artificial
<220> FEATURE:
<223> OTHER INFORMATION: EYD-P-sfi-Rev

<400> SEQUENCE: 23
aaaggccatt taggccactg acgtctgtct tgacgc                          36

<210> SEQ ID NO 24
<211> LENGTH: 36
<212> TYPE: DNA
<213> ORGANISM: Artificial
<220> FEATURE:
<223> OTHER INFORMATION: EYD-T-Sfi-Fo

<400> SEQUENCE: 24
tatggccttg atggcccagc attgagtcca acgagc                          36

<210> SEQ ID NO 25
<211> LENGTH: 20
<212> TYPE: DNA
<213> ORGANISM: Artificial
<220> FEATURE:
<223> OTHER INFORMATION: EYD-T-Rev

<400> SEQUENCE: 25
agatcgaagt tggaatgaga                                            20

<210> SEQ ID NO 26
<211> LENGTH: 20
<212> TYPE: DNA
<213> ORGANISM: Artificial
<220> FEATURE:
<223> OTHER INFORMATION: EYD-V

<400> SEQUENCE: 26
```

```
cgagtttcta agatgtacat                                            20

<210> SEQ ID NO 27
<211> LENGTH: 25
<212> TYPE: DNA
<213> ORGANISM: Artificial
<220> FEATURE:
<223> OTHER INFORMATION: URA3-P-R1

<400> SEQUENCE: 27
gttgccaata tctgcgaact ttctg                                      25

<210> SEQ ID NO 28
<211> LENGTH: 39
<212> TYPE: DNA
<213> ORGANISM: Artificial
<220> FEATURE:
<223> OTHER INFORMATION: LPR-F

<400> SEQUENCE: 28
ataggcctaa atggcctgca tcgatctagg gataacagg                       39

<210> SEQ ID NO 29
<211> LENGTH: 42
<212> TYPE: DNA
<213> ORGANISM: Artificial
<220> FEATURE:
<223> OTHER INFORMATION: LPR-R

<400> SEQUENCE: 29
ataggccatc aaggccgcta gatagagtcg agaattaccc tg                   42

<210> SEQ ID NO 30
<211> LENGTH: 24
<212> TYPE: DNA
<213> ORGANISM: Artificial
<220> FEATURE:
<223> OTHER INFORMATION: LIP2-PF

<400> SEQUENCE: 30
cggtcggaat aattactgtg gacc                                       24

<210> SEQ ID NO 31
<211> LENGTH: 41
<212> TYPE: DNA
<213> ORGANISM: Artificial
<220> FEATURE:
<223> OTHER INFORMATION: LIP2-PR

<400> SEQUENCE: 31
aaaggccatt taggccactt gggtatcaat tgagggcttt c                    41

<210> SEQ ID NO 32
<211> LENGTH: 38
<212> TYPE: DNA
<213> ORGANISM: Artificial
<220> FEATURE:
<223> OTHER INFORMATION: LIP2-TF

<400> SEQUENCE: 32
tatggccttg atggcctgtc tcggaggagc tgcagccc                        38

<210> SEQ ID NO 33
<211> LENGTH: 29
<212> TYPE: DNA
```

```
<213> ORGANISM: Artificial
<220> FEATURE:
<223> OTHER INFORMATION: LIP2-TR

<400> SEQUENCE: 33
ttgcttaaca ccagtatcag aacacagac                                    29

<210> SEQ ID NO 34
<211> LENGTH: 22
<212> TYPE: DNA
<213> ORGANISM: Artificial
<220> FEATURE:
<223> OTHER INFORMATION: LIP2-V

<400> SEQUENCE: 34
acggaagcga agtacctgtc ac                                           22

<210> SEQ ID NO 35
<211> LENGTH: 21
<212> TYPE: DNA
<213> ORGANISM: Artificial
<220> FEATURE:
<223> OTHER INFORMATION: ACT-F

<400> SEQUENCE: 35
ggccagccat atcgagtcgc a                                            21

<210> SEQ ID NO 36
<211> LENGTH: 18
<212> TYPE: DNA
<213> ORGANISM: Artificial
<220> FEATURE:
<223> OTHER INFORMATION: ACT-R

<400> SEQUENCE: 36
tccaggccgt cctctccc                                                18

<210> SEQ ID NO 37
<211> LENGTH: 20
<212> TYPE: DNA
<213> ORGANISM: Artificial
<220> FEATURE:
<223> OTHER INFORMATION: EYKq-F

<400> SEQUENCE: 37
cttctgctgg accctctgtc                                              20

<210> SEQ ID NO 38
<211> LENGTH: 20
<212> TYPE: DNA
<213> ORGANISM: Artificial
<220> FEATURE:
<223> OTHER INFORMATION: EYKq-R

<400> SEQUENCE: 38
actgcacgta ggggatcaac                                              20

<210> SEQ ID NO 39
<211> LENGTH: 20
<212> TYPE: DNA
<213> ORGANISM: Artificial
<220> FEATURE:
<223> OTHER INFORMATION: EYD qpcr Fo

<400> SEQUENCE: 39
catgaccttt cggaaccagt                                              20
```

<210> SEQ ID NO 40
<211> LENGTH: 20
<212> TYPE: DNA
<213> ORGANISM: Artificial
<220> FEATURE:
<223> OTHER INFORMATION: EYD qpcr Rev

<400> SEQUENCE: 40
aacgcctctc tggtcttcaa                                                     20

<210> SEQ ID NO 41
<211> LENGTH: 32
<212> TYPE: DNA
<213> ORGANISM: Artificial
<220> FEATURE:
<223> OTHER INFORMATION: pEYK300 F

<400> SEQUENCE: 41
gacatcgatg catctacttt tctctatact gt                                       32

<210> SEQ ID NO 42
<211> LENGTH: 33
<212> TYPE: DNA
<213> ORGANISM: Artificial
<220> FEATURE:
<223> OTHER INFORMATION: pEYK R

<400> SEQUENCE: 42
gacggatcca gtagatgtgt aagtgtgtag aag                                      33

<210> SEQ ID NO 43
<211> LENGTH: 31
<212> TYPE: DNA
<213> ORGANISM: Artificial
<220> FEATURE:
<223> OTHER INFORMATION: MT-TATAampli-F

<400> SEQUENCE: 43
acgatcgatt ttgtgcaagt gtgtgtgtgt g                                        31

<210> SEQ ID NO 44
<211> LENGTH: 31
<212> TYPE: DNA
<213> ORGANISM: Artificial
<220> FEATURE:
<223> OTHER INFORMATION: MT-TATAampli-R

<400> SEQUENCE: 44
acgactagtc aggtcatcgg attatgcaag g                                        31

<210> SEQ ID NO 45
<211> LENGTH: 89
<212> TYPE: DNA
<213> ORGANISM: Artificial
<220> FEATURE:
<223> OTHER INFORMATION: pEYK-mut1

<400> SEQUENCE: 45
cgatgcatct actttctct atactgtacg tttcaatctg gggaagcgga atcccaaaag          60
ggaaagccgc cgcattaagc tccacagcc                                           89

<210> SEQ ID NO 46
<211> LENGTH: 89
<212> TYPE: DNA

```
<213> ORGANISM: Artificial
<220> FEATURE:
<223> OTHER INFORMATION: pEYK-mut1BIS

<400> SEQUENCE: 46
cgatgcatct actttctct atactgtacg tttcaatctg gggaagcgga atcccaaaag    60
gacgcgtcgc cgcattaagc tccacagcc                                    89

<210> SEQ ID NO 47
<211> LENGTH: 21
<212> TYPE: DNA
<213> ORGANISM: Artificial
<220> FEATURE:
<223> OTHER INFORMATION: pEYK-mut2

<400> SEQUENCE: 47
ttgcataatc cgatgacctg a                                            21

<210> SEQ ID NO 48
<211> LENGTH: 21
<212> TYPE: DNA
<213> ORGANISM: Artificial
<220> FEATURE:
<223> OTHER INFORMATION: pEYK-mut2BIS

<400> SEQUENCE: 48
ttgtacgcgt agatgacctg a                                            21

<210> SEQ ID NO 49
<211> LENGTH: 45
<212> TYPE: DNA
<213> ORGANISM: Artificial
<220> FEATURE:
<223> OTHER INFORMATION: pEYK-mutA

<400> SEQUENCE: 49
ggcgtaattc gaggtgtcgg aacgtattag gctactggac tgatc                  45

<210> SEQ ID NO 50
<211> LENGTH: 45
<212> TYPE: DNA
<213> ORGANISM: Artificial
<220> FEATURE:
<223> OTHER INFORMATION: pEYK-mutABIS

<400> SEQUENCE: 50
ggcgtaattc gaggtgtcgg aacatgcgca tctactggac tgatc                  45

<210> SEQ ID NO 51
<211> LENGTH: 67
<212> TYPE: DNA
<213> ORGANISM: Artificial
<220> FEATURE:
<223> OTHER INFORMATION: pEYK-mutB

<400> SEQUENCE: 51
tacgtagatg aaaagagata tgacatgcaa agttagaccc cttcgcctta gggttttccc  60
tttcgcg                                                            67

<210> SEQ ID NO 52
<211> LENGTH: 67
<212> TYPE: DNA
<213> ORGANISM: Artificial
<220> FEATURE:
<223> OTHER INFORMATION: pEYK-mutBbis
```

```
<400> SEQUENCE: 52
tacgtagatg aaaagagata tgacatgcaa agttagaccc cttcgcctta gggttttcct    60
gcgcacg                                                              67

<210> SEQ ID NO 53
<211> LENGTH: 20
<212> TYPE: DNA
<213> ORGANISM: Artificial
<220> FEATURE:
<223> OTHER INFORMATION: MT-URA3-for

<400> SEQUENCE: 53
gcgtaggtga agtcgtcaat                                                20

<210> SEQ ID NO 54
<211> LENGTH: 21
<212> TYPE: DNA
<213> ORGANISM: Artificial
<220> FEATURE:
<223> OTHER INFORMATION: MT-YFP-rev

<400> SEQUENCE: 54
cagatgaact tcagggtcag c                                              21

<210> SEQ ID NO 55
<211> LENGTH: 21
<212> TYPE: DNA
<213> ORGANISM: Artificial
<220> FEATURE:
<223> OTHER INFORMATION: pTEF-start

<400> SEQUENCE: 55
gggtataaaa gaccaccgtc c                                              21

<210> SEQ ID NO 56
<211> LENGTH: 23
<212> TYPE: DNA
<213> ORGANISM: Artificial
<220> FEATURE:
<223> OTHER INFORMATION: 61stop

<400> SEQUENCE: 56
gtagatagtt gaggtagaag ttg                                            23

<210> SEQ ID NO 57
<211> LENGTH: 13
<212> TYPE: DNA
<213> ORGANISM: Artificial
<220> FEATURE:
<223> OTHER INFORMATION: Sfi1

<400> SEQUENCE: 57
ggcctaaatg gcc                                                       13

<210> SEQ ID NO 58
<211> LENGTH: 13
<212> TYPE: DNA
<213> ORGANISM: Artificial
<220> FEATURE:
<223> OTHER INFORMATION: Sfi1*

<400> SEQUENCE: 58
ggccatcaag gcc                                                       13
```

<210> SEQ ID NO 59
<211> LENGTH: 1029
<212> TYPE: DNA
<213> ORGANISM: Artificial Sequence
<220> FEATURE:
<223> OTHER INFORMATION: Lip2prepro-CalB sequence

<400> SEQUENCE: 59

```
atgaagctgc tgtctctgac cggtgtggct ggtgttctgg ccacctgtgt cgctgccacc      60
cctctggtga agcgactgcc ttctggatct gaccctgcct ctctcagcc caagtctgtt     120
ctggacgctg gtctgacctg tcagggagct tctccttctt ctgtgtctaa gcccattctc     180
ctggtgcctg aaccggaac caccggtcct cagtctttcg actcgaactg gattcctctg     240
tctacccagc tgggatacac ccctgttgg atttctcctc ctcctttcat gctgaacgac     300
acccaggtga acaccgagta catggtgaac gccattaccg ctctgtacgc tggctctgga     360
aacaacaagc tgcccgttct gacctggtct cagggaggtc tggtggctca gtggggtctg     420
accttcttcc cttctattcg atctaaggtg accgactga tggccttcgc tcccgactac     480
aagggaaccg ttctggctgg tcctctggac gctctggctg tctctgctcc ttctgtgtgg     540
cagcagacca ccggctctgc tctgaccacc gctctgcgaa cgctggagg tctgacccag     600
attgtcccca ccaccaacct gtactctgcc accgacgaga ttgtccagcc tcaggtgtct     660
aactctcctc tggactcttc gtacctgttc aacggaaaga cattcaggc tcaggctgtc     720
tgtggacctc tgttcgacat tgaccacgct ggctctctga cctctcagtt ctcctacgtg     780
gttgacgat ctgctctgcg atctaccacc ggtcaggctc gatctgctga ctacggtatc     840
accgactgta accctctgcc tgccaacgac ctgaccccctg agcagaaggt ggctgctgct     900
gctctgctgg ctcccgaggc tgctgccatt gtcgctggtc ccaagcagaa ctgcgagccc     960
gacctgatgc cttacgctcg acccttcgct gttggaaagc gaacctgttc tggtattgtc    1020
accccttaa                                                            1029
```

<210> SEQ ID NO 60
<211> LENGTH: 23
<212> TYPE: DNA
<213> ORGANISM: Artificial Sequence
<220> FEATURE:
<223> OTHER INFORMATION: Primer P1 TEF FW

<400> SEQUENCE: 60

```
ggtctctacg ggggttggcg gcg                                              23
```

<210> SEQ ID NO 61
<211> LENGTH: 28
<212> TYPE: DNA
<213> ORGANISM: Artificial Sequence
<220> FEATURE:
<223> OTHER INFORMATION: Primer P1 TEF RV

<400> SEQUENCE: 61

```
ggtctctcat tcttcgggtg tgagttac                                         28
```

<210> SEQ ID NO 62
<211> LENGTH: 46
<212> TYPE: DNA
<213> ORGANISM: Artificial Sequence
<220> FEATURE:
<223> OTHER INFORMATION: Primer P1 EYK FW

<400> SEQUENCE: 62

```
ggtctctacg gcccatcgat ggaaaccttz ataggagact acttcc          46
```

<210> SEQ ID NO 63
<211> LENGTH: 33
<212> TYPE: DNA
<213> ORGANISM: Artificial Sequence
<220> FEATURE:
<223> OTHER INFORMATION: Primer P1 EYK RV

<400> SEQUENCE: 63

```
ggtctctcat tggatccagt agatgtgtaa gtg                         33
```

<210> SEQ ID NO 64
<211> LENGTH: 50
<212> TYPE: DNA
<213> ORGANISM: Artificial Sequence
<220> FEATURE:
<223> OTHER INFORMATION: Primer P1 EYD FW

<400> SEQUENCE: 64

```
gggggtctc tacggcccat cgatggaaac cttaatagga gactacttcc       50
```

<210> SEQ ID NO 65
<211> LENGTH: 38
<212> TYPE: DNA
<213> ORGANISM: Artificial Sequence
<220> FEATURE:
<223> OTHER INFORMATION: Primer P1 EYD RV

<400> SEQUENCE: 65

```
cccggtctct catttgtgta tgtgtgtgtg tgtgtgtg                    38
```

<210> SEQ ID NO 66
<211> LENGTH: 35
<212> TYPE: DNA
<213> ORGANISM: Artificial Sequence
<220> FEATURE:
<223> OTHER INFORMATION: Primer EYD UAS1 MluI Fw

<400> SEQUENCE: 66

```
ccttaatagg agactacttc cgacgcgtaa ttagg                       35
```

<210> SEQ ID NO 67
<211> LENGTH: 35
<212> TYPE: DNA
<213> ORGANISM: Artificial Sequence
<220> FEATURE:
<223> OTHER INFORMATION: Primer EYD UAS1 MluI RV

<400> SEQUENCE: 67

```
cctaattacg cgtcggaagt agtctcctat taagg                       35
```

<210> SEQ ID NO 68
<211> LENGTH: 30
<212> TYPE: DNA
<213> ORGANISM: Artificial Sequence
<220> FEATURE:
<223> OTHER INFORMATION: Primer EYD UAS2 MluI Fw

<400> SEQUENCE: 68

```
gaactcgata cgcgtgccgt actctggaaa                             30
```

<210> SEQ ID NO 69
<211> LENGTH: 30
<212> TYPE: DNA

<213> ORGANISM: Artificial Sequence
<220> FEATURE:
<223> OTHER INFORMATION: Primer EYD UAS2 MluI RV

<400> SEQUENCE: 69
tttccagagt acggcacgcg tatcgagttc          30

<210> SEQ ID NO 70
<211> LENGTH: 22
<212> TYPE: DNA
<213> ORGANISM: Artificial Sequence
<220> FEATURE:
<223> OTHER INFORMATION: Primer ZetaUp-internal-FW

<400> SEQUENCE: 70
tatcttctga cgcattgacc ac          22

<210> SEQ ID NO 71
<211> LENGTH: 20
<212> TYPE: DNA
<213> ORGANISM: Artificial Sequence
<220> FEATURE:
<223> OTHER INFORMATION: Primer URA3-internal-FW

<400> SEQUENCE: 71
catccagaga agcacacagg          20

<210> SEQ ID NO 72
<211> LENGTH: 22
<212> TYPE: DNA
<213> ORGANISM: Artificial Sequence
<220> FEATURE:
<223> OTHER INFORMATION: Primer URA3-internal-RV

<400> SEQUENCE: 72
caactaactc gtaactatta cc          22

<210> SEQ ID NO 73
<211> LENGTH: 20
<212> TYPE: DNA
<213> ORGANISM: Artificial Sequence
<220> FEATURE:
<223> OTHER INFORMATION: Primer Redstar-internal-FW

<400> SEQUENCE: 73
aagacggtgg cgttgttact          20

<210> SEQ ID NO 74
<211> LENGTH: 20
<212> TYPE: DNA
<213> ORGANISM: Artificial Sequence
<220> FEATURE:
<223> OTHER INFORMATION: Primer RedStar-internal-RV

<400> SEQUENCE: 74
gacttgcttc ttggccttgt          20

<210> SEQ ID NO 75
<211> LENGTH: 21
<212> TYPE: DNA
<213> ORGANISM: Artificial Sequence
<220> FEATURE:
<223> OTHER INFORMATION: Primer Tlip2-internal-FW

<400> SEQUENCE: 75
tgcgttcctc taagacaaat c          21

<210> SEQ ID NO 76
<211> LENGTH: 23
<212> TYPE: DNA
<213> ORGANISM: Artificial Sequence
<220> FEATURE:
<223> OTHER INFORMATION: Primer Tlip2-internal-RV

<400> SEQUENCE: 76
gatttgtctt agaggaacgc ata                                         23

<210> SEQ ID NO 77
<211> LENGTH: 20
<212> TYPE: DNA
<213> ORGANISM: Artificial Sequence
<220> FEATURE:
<223> OTHER INFORMATION: Primer ZetaDown-internal-RV

<400> SEQUENCE: 77
ggtaacgccg attctctctg                                             20

<210> SEQ ID NO 78
<211> LENGTH: 488
<212> TYPE: DNA
<213> ORGANISM: Yarrowia lipolytica

<400> SEQUENCE: 78
tccaacaaca atagtgaatc ccatttgtgt caagtgtgtg tgtgtgtgtg tgtgtggtgt    60
gtttgtgtgt tagaacggat gttctggtga gtgtgagtgt gtagttgtgt gatgagacct   120
tggtgccacc ccaaggtata tatatataac acctccagga gctctaaaaa ggcatctact   180
tttctctata ctgtacgttt caatctgggg aagcggaatc ccaaaaggga aagccgccgc   240
attaagctcc acagccttgc ataatccgat gacctgacta gtgcggacaa agactattat   300
ttcgaggcaa ggccaccacg taccgcggtc ccaaactttt gcaaagctga aaacagcgtg   360
ggggtcaacg tggatcagaa agaggggcag atcagcttct ataagaagct cctttcccca   420
caattggccc acacgacact tctacacact tacacatcta ctatgtccac aaaacatctg   480
ttcaacga                                                           488

<210> SEQ ID NO 79
<211> LENGTH: 442
<212> TYPE: DNA
<213> ORGANISM: Yarrowia phangngensis

<400> SEQUENCE: 79
tccaacaaca attgtgaatc ccatttatt ttgtagtgtc tgataaagt tgagtgattg     60 gtttccagtg gggaagaggt tattcttgta gtcggagctt tttgatccca gcactatta  120 taacacaatt acaatctgtc tgtctctaaa ttcatacttt ccgtaaattc ctattacgat  180
ttattctagt ccctttcgcg gaacctcaaa gtggaaagcc gtggaattaa gctcataaag  240
cttgcattat ccgacgacaa tacaaacctt aactcgaaca aaggaattca tggggacatt  300
tacgtggggg ccggtctaac tgtgctattg agtgtcccgt cagaaaaaat gctataaagg  360
atgattctcc tctctttcct ttttgtctct catcaattct gattacggtt cacaacatgt  420
caacaaagca tctctttaac ga                                          442

<210> SEQ ID NO 80
<211> LENGTH: 384
<212> TYPE: DNA

-continued

<213> ORGANISM: Yarrowia yakushimensis

<400> SEQUENCE: 80

| tccaacaaca atgatgaatc ccatagtagt gtaaggtgtt ggcgtgtgtg tttgaagtga | 60 |
| ccagaccaca caaggtata tatatcaccg ctacgagctc ctcaaacagt ccttctttca | 120 |
| gtctacggaa tcctgaaatg gaaagccgtc acataaactt tttaatcatg cataatccga | 180 |
| tgacctgact ggtccgacgg agtctatttt tttttcagac aatgactttt cgatactaac | 240 |
| ccactcgtag cgtggatccg taaacagaga gtggggtca gggatcggaa agagggcac | 300 |
| attgttccta aagaccgtg tatccccaaa atctcaacct caacattcac ccaaagacat | 360 |
| gtctacaaaa cacctattca acga | 384 |

<210> SEQ ID NO 81
<211> LENGTH: 460
<212> TYPE: DNA
<213> ORGANISM: Yarrowia alimentaria

<400> SEQUENCE: 81

| accaacaaca attgtgaatc ccattttgaa taatgtcttg tgtgtagtga gtggtttgtg | 60 |
| agggaggttg tgttctgttg tacgttgtgt gctctatacg ggcggcctag tatatatata | 120 |
| taactcctaa ggcagaccca aaggcacccc cacagtcttt tcccacgtcc tgtcagtaac | 180 |
| aaggcccggg catgctctca ttttctgggg aagggtgcgg aatcccaaaa gggaaagccg | 240 |
| tcccaataaa ctcaataaac gtgcataatc cgatgacctg acaagcagac aaagactaat | 300 |
| tttccaagca agtgccgaaa gtgccaatac ccacgctatg tgtacgtggg ggcaccagaa | 360 |
| gacccaaaga ggacccgaca gatctataaa gactctctcg ccactcaccc ttctcatcca | 420 |
| ccaacacaca aacaatgtcc accaaacatc ttttcaacga | 460 |

<210> SEQ ID NO 82
<211> LENGTH: 526
<212> TYPE: DNA
<213> ORGANISM: Yarrowia galli

<400> SEQUENCE: 82

| tccaacaaca atagtgaatc ccatttgtgt gtgtgtgtgt gtgtaagagt ggttttgtgt | 60 |
| gtgttagaac ggttgttctg ttgtgtgtgt ttgtgtagtt tgtgtgtttg tgtcgttctg | 120 |
| gcctggccaa ggtatatata ccaccaactg tcttaccaag agctctaaag acctcctcag | 180 |
| ccattcagta tagtacgttt caatccgggg aagcggcatc ccaattggga agccgccgc | 240 |
| attaagctcc acagccttgc ataatccgat gacctgacta gtgcagacaa agactttaat | 300 |
| ttttcgaggc aagcacacta cacacaacaa ccacgtatcg tgccaaactt ttgcaaaaca | 360 |
| gaaaacgcca gagtgggggt caaattggct tggatcagga agggagaaag aggggctgtc | 420 |
| gggatcagct tctataagaa cctgtcttcc cccaattggt ccagatcaac caactacaca | 480 |
| caactacacc acaactacaa atgtccacca aacctgtt caacga | 526 |

<210> SEQ ID NO 83
<211> LENGTH: 316
<212> TYPE: DNA
<213> ORGANISM: Yarrowia lipolytica

<400> SEQUENCE: 83

| aaaccttaat aggagactac ttccgtttcc taattaggac ttccgcgacc ccagacaaag | 60 |
| cggcttggag taggcctcgt gtccggccta gggcagaaac agctccggaa ctcgattgag | 120 |

```
aagccgtact ctggaaagtc tagaggaagt tccaaggtcg agtctcttcg atataaaagg    180
acgccatgga agctctgtag ttcgatatca aatactgaca acagtttcca aacacacaaa    240
cacacacaca cacacacaca cacatacaca aatggtttct tcagccgcta cttctgctct    300
gcccatctcg gcaccc                                                    316

<210> SEQ ID NO 84
<211> LENGTH: 310
<212> TYPE: DNA
<213> ORGANISM: Yarrowia galli

<400> SEQUENCE: 84
ttacggaaac ctaaatggaa gactacttcc gtttcctaat atggacatcc gcgaccccca     60
gacaaagcgg cctggagtag acctcgtgtc cggcctaggg aagaaacagc tccgatctc    120 gattgagaag ccgttctatg gaaagtctag agacagagct gaggtgggtc tctttgatat    180
aaaagggtca ccactgtcgt cgtagtttcg acatcaatta actgacaaca ctcttctaac    240
acacacacac acaaacacac acacaatggt ttctacagcc gctacttctg ctctgcccat    300
ctcggcacct                                                           310

<210> SEQ ID NO 85
<211> LENGTH: 296
<212> TYPE: DNA
<213> ORGANISM: Yarrowia phangngensis

<400> SEQUENCE: 85
atgactgaac ctaaaagact atagatttct atttccctat taggttgccg ctctccccca     60
tattaaccta attcgtgtat gtgtcattag ctcccttgtg tgattacgga tcttcattga    120
gaaagccgga atgtccaaga atagcggagt ttcggagctt aggtatcatc tagatataaa    180
agggtcaaag gctgctctca ggattcaata cagtatctct acttacaaca ataacccaat    240
cttcacacac aatggtttcc atcactccta cttctgccct gcccctctct gctcct        296

<210> SEQ ID NO 86
<211> LENGTH: 250
<212> TYPE: DNA
<213> ORGANISM: Yarrowia yakushimensis

<400> SEQUENCE: 86
aaacccagac tctaaatgca atccagttgc gtttcctaat gcggacttcc gcgacgacac     60
ggcgccttac tagttgagaa aacagtcccg gatctcaatt gagaagccgt agtgaaaagt    120
gtagggaagc tacaagaccg tctgatatat ataggctggg gatttctcca gagttggtat    180
caatcaacag ttatctcttc acacaatggt ttctacaact tccacttctg ctctgccaat    240
ttcggccccc                                                           250

<210> SEQ ID NO 87
<211> LENGTH: 297
<212> TYPE: DNA
<213> ORGANISM: Yarrowia alimentaria

<400> SEQUENCE: 87
cggattataa ctttaaagct tgctacttcc gtttcctaat taggacatcc gcgacttcat     60
acaagcggct tgtcggaagg cctcgtgtct catgagcgca ctaatagtct cgggtctgga    120
ttgagaagcc gttcagcctt caaagtctag aatcaaagtg aagacggagg attcgatata    180
```
taagggcacc atgaccacct cttggtaggc atcaaaacac cctcacacac acacacacac    240
atacaaaaca caatggtttc ctctgctgct acctccgcac tccccatctc ggcacct       297

<210> SEQ ID NO 88
<211> LENGTH: 382
<212> TYPE: DNA
<213> ORGANISM: Artificial Sequence
<220> FEATURE:
<223> OTHER INFORMATION: TEF sequence for promoter construction

<400> SEQUENCE: 88
ggtctctacg ggggttggcg gcgtatttgt gtcccaaaaa acagccccaa ttgccccaat    60
tgaccccaaa ttgacccagt agcgggccca accccggcga gagccccctt caccccacat    120
atcaaacctc ccccggttcc cacacttgcc gttaagggcg tagggtactg cagtctggaa    180
tctacgcttg ttcagacttt gtactagttt ctttgtctgg ccatccgggt aacccatgcc    240
ggacgcaaaa tagactactg aaaattttt tgctttgtgg ttgggacttt agccaagggt     300
ataaaagacc accgtccccg aattaccttt cctcttcttt tctctctctc cttgtcaact    360
cacacccgaa gaatgagaga cc                                              382

<210> SEQ ID NO 89
<211> LENGTH: 113
<212> TYPE: DNA
<213> ORGANISM: Artificial Sequence
<220> FEATURE:
<223> OTHER INFORMATION: Core TEF sequence for promoter construction

<400> SEQUENCE: 89
ggttgggact ttagccaagg gtataaaaga ccaccgtccc cgaattacct ttcctcttct    60
tttctctctc tccttgtcaa ctcacacccg aaggatccca caaatgagag acc           113

<210> SEQ ID NO 90
<211> LENGTH: 325
<212> TYPE: DNA
<213> ORGANISM: Artificial Sequence
<220> FEATURE:
<223> OTHER INFORMATION: EYK1 sequence for promoter construction

<400> SEQUENCE: 90
ggtctctacg gatcgattgc atctactttt ctctatactg tacgtttcaa tctggggaag    60
cggaatccca aaagggaaag ccgccgcatt aagctccaca gccttgcata atccgatgac    120
ctgactagtg cggacaaaga ctattatttc gaggcaaggc caccacgtac cgcggtccca    180 aactttgca aagctgaaaa cagcgtgggg gtcaacgtgg atcagaaaga ggggcagatc     240
agcttctata agaagctcct ttccccacaa ttggcccaca cgacacttct acacacttac    300
acatctactg gatccatgag agacc                                           325

<210> SEQ ID NO 91
<211> LENGTH: 382
<212> TYPE: DNA
<213> ORGANISM: Artificial Sequence
<220> FEATURE:
<223> OTHER INFORMATION: EYK1-2AB sequence for promoter construction

<400> SEQUENCE: 91
ggtctctacg gcgatacgcg tatcgatgca tctactttc tctatactgt acgtttcaat     60
ctggggaagc ggaatcccaa aagggaaagc cgccgcatta agctccacag cgggaagcgg    120
aatcccaaaa gggaaagccg ccgcattaag ctccacagcc ttgcataatc cgatgacctg    180

```
actagtgcgg acaaagacta ttatttcgag gcaaggccac cacgtaccgc ggtcccaaac      240
ttttgcaaag ctgaaaacag cgtggggtc aacgtggatc agaaagaggg gcagatcagc      300
ttctataaga agctcctttc cccacaattg gcccacacga cacttctaca cacttacaca      360
tctactggat ccatgagaga cc                                               382

<210> SEQ ID NO 92
<211> LENGTH: 430
<212> TYPE: DNA
<213> ORGANISM: Artificial Sequence
<220> FEATURE:
<223> OTHER INFORMATION: EYK1-3AB sequence for promoter construction

<400> SEQUENCE: 92
ggtctctacg gcgatacgcg tatcgatgca tctactttc tctatactgt acgtttcaat       60
ctggggaagc ggaatcccaa aagggaaagc cgccgcatta agctccacag cgggaagcgg     120
aatcccaaaa gggaaagccg ccgcattaag ctccacagcg ggaagcggaa tcccaaaagg     180
gaaagccgcc gcattaagct ccacagcctt gcataatccg atgacctgac tagtgcggac     240
aaagactatt atttcgaggc aaggccacca cgtaccgcgg tcccaaactt ttgcaaagct     300
gaaaacagcg tggggtcaa cgtggatcag aaagaggggc agatcagctt ctataagaag     360
ctcctttccc cacaattggc ccacacgaca cttctacaca cttacacatc tactggatcc     420
atgagagacc                                                            430

<210> SEQ ID NO 93
<211> LENGTH: 478
<212> TYPE: DNA
<213> ORGANISM: Artificial Sequence
<220> FEATURE:
<223> OTHER INFORMATION: EYK1-4AB sequence for promoter construction

<400> SEQUENCE: 93
ggtctctacg gcgatacgcg tatcgatgca tctactttc tctatactgt acgtttcaat       60
ctggggaagc ggaatcccaa aagggaaagc cgccgcatta agctccacag cgggaagcgg     120
aatcccaaaa gggaaagccg ccgcattaag ctccacagcg ggaagcggaa tcccaaaagg     180
gaaagccgcc gcattaagct ccacagcggg aagcggaatc ccaaaaggga agccgccgc     240 attaagctcc acagccttgc ataatccgat gacctgacta gtgcggacaa agactattat     300
ttcgaggcaa ggccaccacg taccgcggtc ccaaactttt gcaaagctga aaacagcgtg     360
ggggtcaacg tggatcagaa agaggggcag atcagcttct ataagaagct cctttcccca     420
caattggccc acacgacact tctacacact tacacatcta ctggatccat gagagacc       478

<210> SEQ ID NO 94
<211> LENGTH: 526
<212> TYPE: DNA
<213> ORGANISM: Artificial Sequence
<220> FEATURE:
<223> OTHER INFORMATION: EYK1-5AB sequence for promoter construction

<400> SEQUENCE: 94
ggtctctacg gcgatacgcg tatcgatgca tctactttc tctatactgt acgtttcaat       60
ctggggaagc ggaatcccaa aagggaaagc cgccgcatta agctccacag cgggaagcgg     120
aatcccaaaa gggaaagccg ccgcattaag ctccacagcg ggaagcggaa tcccaaaagg     180
gaaagccgcc gcattaagct ccacagcggg aagcggaatc ccaaaaggga agccgccgc     240
```

```
attaagctcc acagcgggaa gcggaatccc aaaagggaaa gccgccgcat taagctccac    300
agccttgcat aatccgatga cctgactagt gcggacaaag actattattt cgaggcaagg    360
ccaccacgta ccgcggtccc aaactttgc aaagctgaaa acagcgtggg ggtcaacgtg     420
gatcagaaag aggggcagat cagcttctat aagaagctcc tttccccaca attggcccac    480
acgacacttc tacacactta cacatctact ggatccatga gagacc                   526
```

<210> SEQ ID NO 95
<211> LENGTH: 205
<212> TYPE: DNA
<213> ORGANISM: Artificial Sequence
<220> FEATURE:
<223> OTHER INFORMATION: Core-EYK1 sequence for promoter construction

<400> SEQUENCE: 95

```
ctgactagtg cggacaaaga ctattatttc gaggcaaggc caccacgtac cgcggtccca    60 aactttgca aagctgaaaa cagcgtgggg gtcaacgtgg atcagaaaga gggggcagatc   120 agcttctata agaagctcct ttccccacaa ttgcccaca cgacacttct acacacttac    180
acatctactg gatccatgag agacc                                          205
```

<210> SEQ ID NO 96
<211> LENGTH: 396
<212> TYPE: DNA
<213> ORGANISM: Artificial Sequence
<220> FEATURE:
<223> OTHER INFORMATION: EYK1-4AB-Core TEF sequence for promoter
      construction

<400> SEQUENCE: 96

```
ggtctctacg gcgatacgcg tatcgatgca tctactttc tctatactgt acgtttcaat     60
ctggggaagc ggaatcccaa aagggaaagc cgccgcatta agctccacag cgggaagcgg   120
aatcccaaaa gggaaagccg ccgcattaag ctccacagcg ggaagcggaa tcccaaaagg   180
gaaagccgcc gcattaagct ccacagcggg aagcggaatc ccaaaaggga agccgccgc    240 attaagctcc acagccttgc ataatccgat gacctgacta gtgcggttgg gactttagcc   300
aagggtataa aagaccaccg tccccgaatt acctttcctc ttctttttctc tctctccttg   360 tcaactcaca cccgaaggat cccacaatga gagacc                              396
```

<210> SEQ ID NO 97
<211> LENGTH: 303
<212> TYPE: DNA
<213> ORGANISM: Artificial Sequence
<220> FEATURE:
<223> OTHER INFORMATION: EYD1AB sequence for promoter construction

<400> SEQUENCE: 97

```
ggtctctacg gcccatcgat ggaaaccta ataggagact acttccgttt cctaattagg     60
acttccgcga cccagacaa agcggcttgg agtaggcctc gtgtccggcc tagggcagaa   120
acagctccgg aactcgattg agaagccgta ctctggaaag tctagaggaa gttccaaggt   180
cgagtctctt cgatataaaa ggacgccatg gaagctctgt agttcgatat caaatactga   240
caacagtttc caaacacaca aacacacaca cacacacaca cacacataca cacatgagag   300
acc                                                                  303
```

<210> SEQ ID NO 98
<211> LENGTH: 304
<212> TYPE: DNA

<213> ORGANISM: Artificial Sequence
<220> FEATURE:
<223> OTHER INFORMATION: EYD1A*B sequence for promoter construction

<400> SEQUENCE: 98

```
ggtctctacg gcccatcgat ggaaaccttaa ataggagact acttccgacg cgttaattag    60
gacttccgcg accccagaca aagcggcttg gagtaggcct cgtgtccggc ctagggcaga   120
aacagctccg gaactcgatt gagaagccgt actctggaaa gtctagagga agttccaagg   180
tcgagtctct tcgatataaa aggacgccat ggaagctctg tagttcgata tcaaatactg   240
acaacagttt ccaaacacac aaacacacac acacacacac acacatac   acacatgaga   300 gacc                                                                 304
```

<210> SEQ ID NO 99
<211> LENGTH: 303
<212> TYPE: DNA
<213> ORGANISM: Artificial Sequence
<220> FEATURE:
<223> OTHER INFORMATION: EYD1AB* sequence for promoter construction

<400> SEQUENCE: 99

```
ggtctctacg gcccatcgat ggaaaccttaa ataggagact acttccgttt cctaattagg    60
acttccgcga ccccagacaa agcggcttgg agtaggcctc gtgtccggcc tagggcagaa   120
acagctccgg aactcgatac gcgtgccgta ctctggaaag tctagaggaa gttccaaggt   180
cgagtctctt cgatataaaa ggacgccatg gaagctctgt agttcgatat caaatactga   240
caacagtttc caaacacaca aacacacaca cacacacaca cacatac a   cacatgagag   300 acc                                                                  303
```

<210> SEQ ID NO 100
<211> LENGTH: 141
<212> TYPE: DNA
<213> ORGANISM: Artificial Sequence
<220> FEATURE:
<223> OTHER INFORMATION: Core-EYD1 sequence for promoter construction

<400> SEQUENCE: 100

```
tagaggaagt tccaaggtcg agtctcttcg atataaaagg acgccatgga agctctgtag    60
ttcgatatca aatactgaca acagtttcca aacacacaaa cacacacaca cacacacaca   120
cacatacaca catgagagac c                                              141
```

<210> SEQ ID NO 101
<211> LENGTH: 52
<212> TYPE: DNA
<213> ORGANISM: Artificial Sequence
<220> FEATURE:
<223> OTHER INFORMATION: UAS1 EYD1

<400> SEQUENCE: 101

```
aaaccttaat aggagactac ttccgtttcc taattaggac ttccgcgacc cc            52
```

```
<210> SEQ ID NO 102
<211> LENGTH: 50
<212> TYPE: DNA
<213> ORGANISM: Artificial Sequence
<220> FEATURE:
<223> OTHER INFORMATION: UAS2 EYD1

<400> SEQUENCE: 102
gggcagaaac agctccggaa ctcgattgag aagccgtact ctggaaagtc            50
```